US008244474B2

(12) United States Patent
Matsuyama et al.

(10) Patent No.: US 8,244,474 B2
(45) Date of Patent: Aug. 14, 2012

(54) FEATURE PATTERN RECOGNITION SYSTEM, METHOD, AND PROGRAM

(75) Inventors: Yasuo Matsuyama, Tokyo (JP); Ryo Kawamura, Tokyo (JP); Keita Shimoda, Kawaguchi (JP)

(73) Assignee: Waseda University, Tokyo (JP)

( * ) Notice: Subject to any disclaimer, the term of this patent is extended or adjusted under 35 U.S.C. 154(b) by 1526 days.

(21) Appl. No.: 11/658,130

(22) PCT Filed: Aug. 2, 2005

(86) PCT No.: PCT/JP2005/014130
§ 371 (c)(1),
(2), (4) Date: Jan. 22, 2007

(87) PCT Pub. No.: WO2006/027913
PCT Pub. Date: Mar. 16, 2006

(65) Prior Publication Data
US 2007/0297676 A1    Dec. 27, 2007

(30) Foreign Application Priority Data

Aug. 10, 2004   (JP) ................................ 2004-233848

(51) Int. Cl.
*G01N 33/50* (2006.01)
*G01N 33/48* (2006.01)
(52) U.S. Cl. .......................................... 702/19; 702/20
(58) Field of Classification Search .................. None
See application file for complete search history.

(56) References Cited

U.S. PATENT DOCUMENTS
2003/0088384 A1    5/2003   Hori et al.

FOREIGN PATENT DOCUMENTS
JP    2003-141102    5/2003
JP    3976331    6/2007

OTHER PUBLICATIONS

Matsuyama et al. (Promoter Recognition for *E. coli* DNA Segments by Independent Component Analysis, 2004, Proceedings of the 2004 IEEE Computational Systems Bioinformatics Conference; 6 pages).*

Quantitative sequence-activity models (QSAM)—tools for sequence design, by J. Jonsson et al, Nucleic Acids Research, 1993, vol. 21, No. 3, pp. 733-739.
DNA Sequence Classification via an Expectation Maximization Algorithm and Neural Networks: A Case Study, by Q. Ma et al, IEEE Transactions on Systems, Man, and Cybernetics, Part C, vol. 31, No. 4, 2001, pp. 468-475.
PlantProm: a database of plant promoter sequences, by I. Shahmuradov et al, Nucleic Acids Research, vol. 31, No. 1, 2003, pp. 114-117.
Promoter Recognition for *E. coli* DNA Segments by Independent Component Analysis, by Y. Matsuyama et al, IEEE 2004 Computational Systems Bioinformatics Conference, pp. 686-691.
"Analysis of *E. coli* promoter structures using neural networks", by I. Mahadevan et al, Nucleic Acids Research, 1994, vol. 22, No. 11, pp. 2158-2165.
"*Escherichia coli* promoter sequences predict in vitro RNA polymerase selectivity", by M. Mulligan et al, Nucleic Acids Research, vol. 12, No. 1, 1984, pp. 789-800.
"Computational Approaches to Identify Promoters and cis-Regulatory Elements in Plant Genomes", by S. Rombauts et al, American Society of Plant Biologists, *Plant Physiology*, vol. 132, Jul. 2003, pp. 1162-1176.
"Decomposition of DNA Sequences into Hidden Components: Applications to Human Genome's Promoter Recognition", by Y. Matsuyama et al, Waseda University, Department of Computer Science, Tokyo, Japan, ismb 2006—Fortaleza, Brazil, 2 pages.

* cited by examiner

*Primary Examiner* — Jason Sims
(74) *Attorney, Agent, or Firm* — Flynn, Thiel, Boutell & Tanis, P.C.

(57) ABSTRACT

A feature pattern recognition system, method, and program capable of recognizing feature pattern with a high accuracy are provided. Discrete symbols (nucleotide symbols or the like) constituting a to-be-recognized sequence (a DNA sequence or the like) are converted to numerals by using symbol frequencies that are obtained according to sequence positions or types of the discrete symbols to generates test data or a test data matrix $X_{test}$, a matrix calculation ($Y_{test}=W_{prom}X_{test}$ or the like) of multiplying a separation matrix ($W_{prom}$ or the like) obtained by an independent component analysis or a principal component analysis with the test data or the test data matrix $X_{test}$ is performed, separation data or a separation data matrix $Y_{test}$ is obtained, and it is decided in which side of a threshold exists a feature decision element (elements of first row or the like) of the $Y_{test}$, so that it is decided whether or not the feature pattern (a promoter or the like) exists in the sequence by using a feature decision element (multiple rows of elements may be used).

24 Claims, 36 Drawing Sheets

F I G. 2
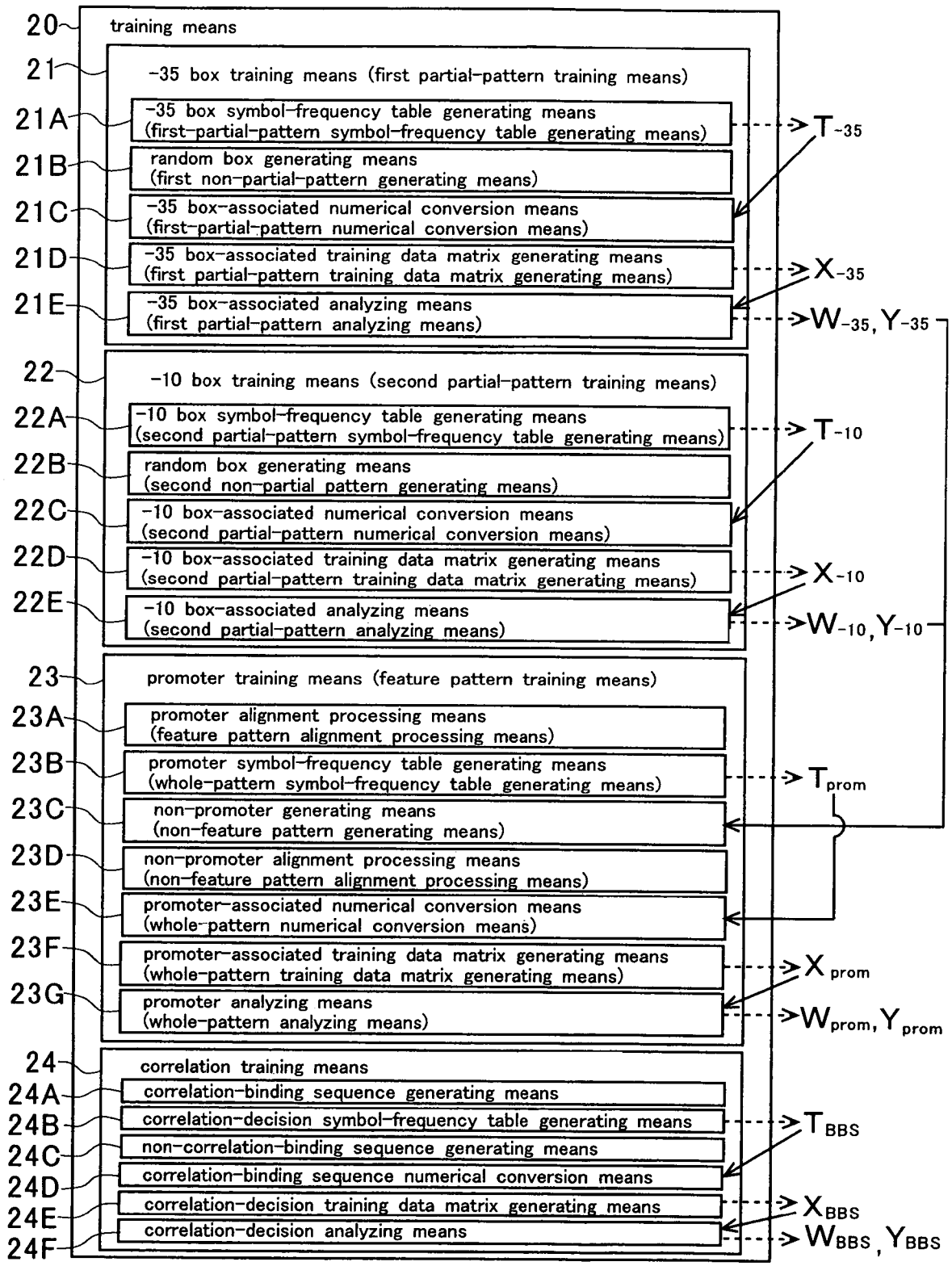

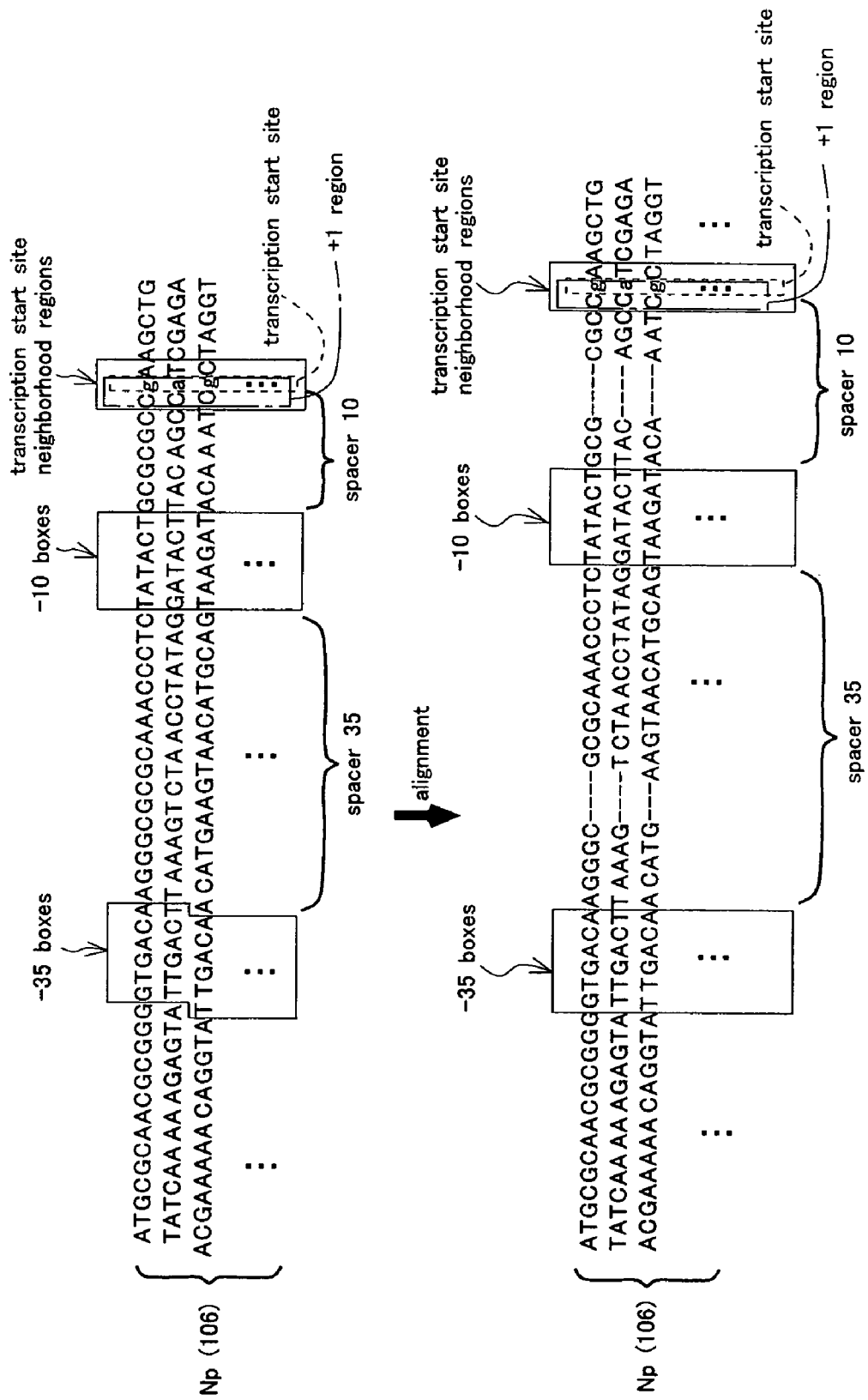

FIG. 6

$T_{-35}$ : -35 box symbol-frequency table

| sequence position in box / type of nucleotide | 1 | 2 | 3 | 4 | 5 | 6 |
|---|---|---|---|---|---|---|
| A | $f_{A,-35}(1)$ | $f_{A,-35}(2)$ | $f_{A,-35}(3)$ | $f_{A,-35}(4)$ | $f_{A,-35}(5)$ | $f_{A,-35}(6)$ |
| T | $f_{T,-35}(1)$ | $f_{T,-35}(2)$ | $f_{T,-35}(3)$ | $f_{T,-35}(4)$ | $f_{T,-35}(5)$ | $f_{T,-35}(6)$ |
| G | $f_{G,-35}(1)$ | $f_{G,-35}(2)$ | $f_{G,-35}(3)$ | $f_{G,-35}(4)$ | $f_{G,-35}(5)$ | $f_{G,-35}(6)$ |
| C | $f_{C,-35}(1)$ | $f_{C,-35}(2)$ | $f_{C,-35}(3)$ | $f_{C,-35}(4)$ | $f_{C,-35}(5)$ | $f_{C,-35}(6)$ |

FIG. 7

-35 box (6 mer)

$N_{-35}$ (72):

| G | T | G | A | C | A |
|---|---|---|---|---|---|
| T | T | G | A | C | T |
| T | T | G | A | C | A |
| ⋮ | ⋮ | ⋮ | ⋮ | ⋮ | ⋮ |

↓ Numerical conversion using $T_{-35}$ 6 columns $N_{-35}$ rows (72 rows):

| $f_{G,-35}(1)$ | $f_{T,-35}(2)$ | $f_{G,-35}(3)$ | $f_{A,-35}(4)$ | $f_{C,-35}(5)$ | $f_{A,-35}(6)$ |
|---|---|---|---|---|---|
| $f_{T,-35}(1)$ | $f_{T,-35}(2)$ | $f_{G,-35}(3)$ | $f_{A,-35}(4)$ | $f_{C,-35}(5)$ | $f_{T,-35}(6)$ |
| $f_{T,-35}(1)$ | $f_{T,-35}(2)$ | $f_{G,-35}(3)$ | $f_{A,-35}(4)$ | $f_{C,-35}(5)$ | $f_{A,-35}(6)$ |
| ⋮ | ⋮ | $B_{-35}$ | | ⋮ | ⋮ |

↓ transpose $N_{-35}$ columns (72 columns)

6 rows: $B_{-35}^T$

Flow of pre-process

FIG. 12

T₋₁₀ : -10 box symbol-frequency table

| type of nucleotide \ sequence position in box | 1 | 2 | 3 | 4 | 5 | 6 |
|---|---|---|---|---|---|---|
| A | $f_{A,-10}(1)$ | $f_{A,-10}(2)$ | $f_{A,-10}(3)$ | $f_{A,-10}(4)$ | $f_{A,-10}(5)$ | $f_{A,-10}(6)$ |
| T | $f_{T,-10}(1)$ | $f_{T,-10}(2)$ | $f_{T,-10}(3)$ | $f_{T,-10}(4)$ | $f_{T,-10}(5)$ | $f_{T,-10}(6)$ |
| G | $f_{G,-10}(1)$ | $f_{G,-10}(2)$ | $f_{G,-10}(3)$ | $f_{G,-10}(4)$ | $f_{G,-10}(5)$ | $f_{G,-10}(6)$ |
| C | $f_{C,-10}(1)$ | $f_{C,-10}(2)$ | $f_{C,-10}(3)$ | $f_{C,-10}(4)$ | $f_{C,-10}(5)$ | $f_{C,-10}(6)$ |

FIG. 13

-10 box (6 mer)

$N_{-10}$ (58)

| T | A | T | A | C | T |
|---|---|---|---|---|---|
| G | A | T | A | C | T |
| T | A | A | G | A | T |
| ⋮ | ⋮ | ⋮ | ⋮ | ⋮ | ⋮ |

↓ numerical conversion using $T_{-10}$ 6 columns $N_{-10}$ rows (58 rows)

| $f_{T,-10}(1)$ | $f_{A,-10}(2)$ | $f_{T,-10}(3)$ | $f_{A,-10}(4)$ | $f_{C,-10}(5)$ | $f_{T,-10}(6)$ |
|---|---|---|---|---|---|
| $f_{G,-10}(1)$ | $f_{A,-10}(2)$ | $f_{T,-10}(3)$ | $f_{A,-10}(4)$ | $f_{C,-10}(5)$ | $f_{T,-10}(6)$ |
| $f_{T,-10}(1)$ | $f_{A,-10}(2)$ | $f_{A,-10}(3)$ | $f_{G,-10}(4)$ | $f_{A,-10}(5)$ | $f_{T,-10}(6)$ |
| ⋮ | ⋮ | ⋮ $B_{-10}$ ⋮ | ⋮ | ⋮ | ⋮ |

↓ transpose $N_{-10}$ columns (58 columns)

6 rows { $B_{-10}^T$ }

Flow (1) of generation of non-promoters and alignment process for generated non-promoters in promoter training Flow (2) of generation of non-promoters and alignment process for generated non-promoters in promoter training $T_{prom}$ : promoter symbol-frequency table

| sequence position in whole pattern / types of symbols including gaps | 1 | 2 | 3 | ... | 6 4 | 6 5 |
|---|---|---|---|---|---|---|
| A | f A,prom(1) | f A,prom(2) | f A,prom(3) | ... | f A,prom(64) | f A,prom(65) |
| T | f T,prom(1) | f T,prom(2) | f T,prom(3) | ... | f T,prom(64) | f T,prom(65) |
| G | f G,prom(1) | f G,prom(2) | f G,prom(3) | ... | f G,prom(64) | f G,prom(65) |
| C | f C,prom(1) | f C,prom(2) | f C,prom(3) | ... | f C,prom(64) | f C,prom(65) |
| — | f -,prom(1) | f -,prom(2) | f -,prom(3) | ... | f -,prom(64) | f -,prom(65) |

Flow of correlation training $T_{BBS}$ : correlation-decision symbol-frequency table

| type of nucleotide \ sequence position in correlation-binding sequence | 1 | 2 | 3 | ... | 1 4 | 1 5 |
|---|---|---|---|---|---|---|
| A | f A,BBS(1) | f A,BBS(2) | f A,BBS(3) | ... | f A,BBS(14) | f A,BBS(15) |
| T | f T,BBS(1) | f T,BBS(2) | f T,BBS(3) | ... | f T,BBS(14) | f T,BBS(15) |
| G | f G,BBS(1) | f G,BBS(2) | f G,BBS(3) | ... | f G,BBS(14) | f G,BBS(15) |
| C | f C,BBS(1) | f C,BBS(2) | f C,BBS(3) | ... | f C,BBS(14) | f C,BBS(15) |

F I G. 3 1
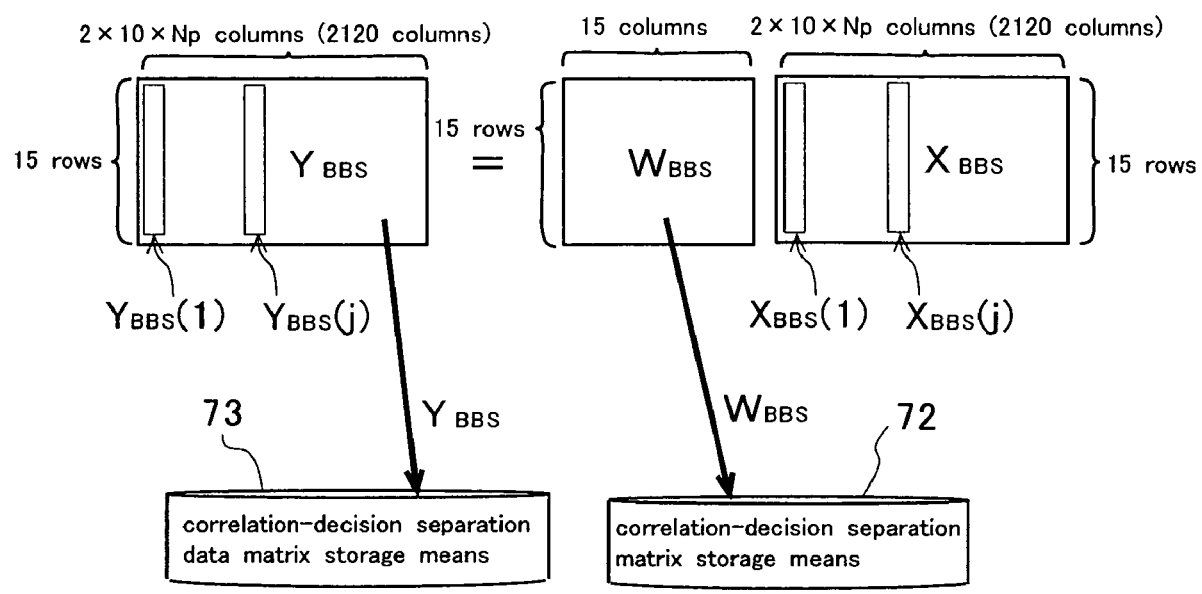

Value of each element (feature element) of first column of $W_{prom}^{-1}$

Value of each element (feature decision element) of first row of $Y_{prom}$

Escherichia coli promoter

FIG. 43

$T_{prom}$ : promoter symbol-frequency table

| type of symbol \ sequence positions in whole pattern | 1 | 2 | 3 | ... | 30 | 31 |
|---|---|---|---|---|---|---|
| A | f A,prom(1) | f A,prom(2) | f A,prom(3) | ... | f A,prom(30) | f A,prom(31) |
| T | f T,prom(1) | f T,prom(2) | f T,prom(3) | ... | f T,prom(30) | f T,prom(31) |
| G | f G,prom(1) | f G,prom(2) | f G,prom(3) | ... | f G,prom(30) | f G,prom(31) |
| C | f C,prom(1) | f C,prom(2) | f C,prom(3) | ... | f C,prom(30) | f C,prom(31) |

F I G. 4 5
Value of each element of first column of $W_{prom}^{-1}$
(example of employing feature element)
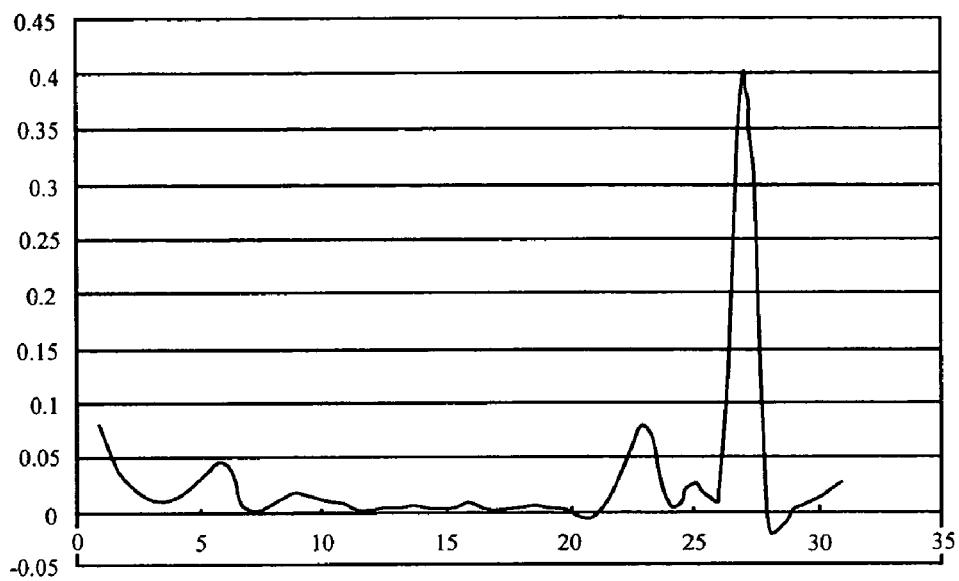
F I G. 4 6
Value of each element of first row of $Y_{prom}$
(example of employing feature decision element)
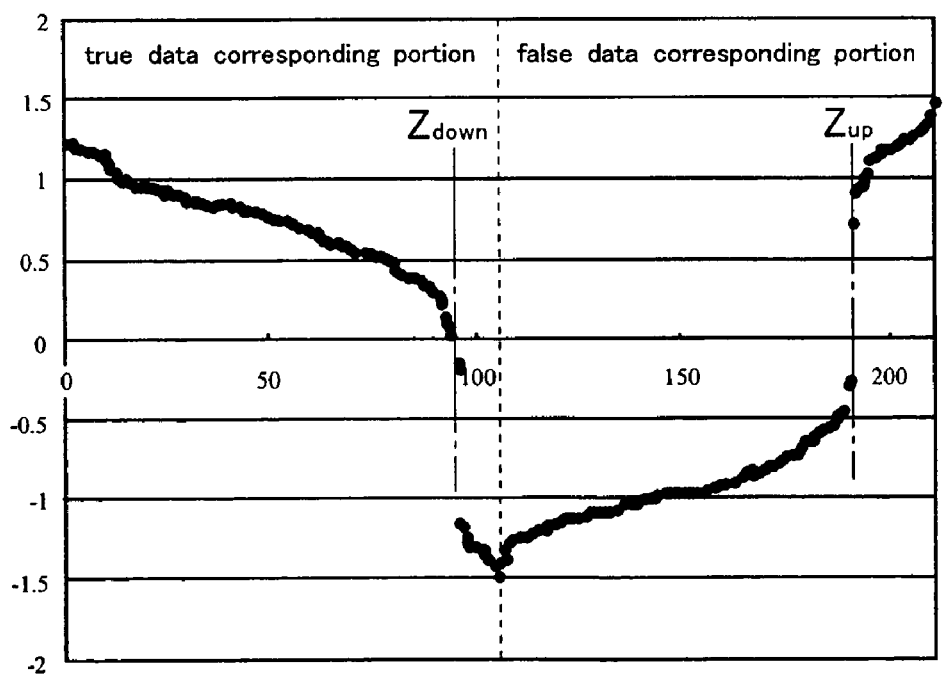

Value of each element of 27-th column of $W_{prom}^{-1}$
(example of not employing feature element)

Value of each element of 27-th row of $Y_{prom}$
(example of not employing feature decision element)

FEATURE PATTERN RECOGNITION SYSTEM, METHOD, AND PROGRAM

TECHNICAL FIELD

The present invention relates to a feature pattern recognition system, a method, and a program. This recognition system decides if one feature pattern among multiple types of pre-known features is included, or if the patterns are similar to each other, or if a new feature pattern similar to the pre-known pattern is included in a sequence constructed with a finite number of discrete symbols, a segment thereof, a test segment extracted from the sequence or the segment itself. The present invention can be used to recognize a promoter in a DNA sequence, a motif in an amino acid sequence, or the like.

BACKGROUND ART

In general, characteristic nucleic base sequences which are called promoters exist in the vicinity of gene coding region of a DNA segment (hereinafter simply referred to as a DNA segment). In the DNA sequence, the promoter is a gene transcription's control site possessing a specific pattern. Therefore, it is very important to decide whether or not the promoter is included in the DNA segment.

FIG. 41 shows an example of a state where an RNA polymerase (ribonucleic acid polymerase which is a kind of enzyme) searches for an *Escherichia coli* promoter in an *Escherichia coli* nucleic base sequence. Only a portion of the nucleic base sequences in the long DNA sequence is transcribed to an RNA sequence. Then, the RNA sequence is translated into an amino acid chain so that a protein is synthesized.

When the RNA polymerase meets a DNA sequence, the RNA polymerase is weakly bound and slides on the DNA. When the RNA polymerase meets the promoter, the RNA polymerase is strongly bound to start the transcription of the DNA sequence.

By performing a biological experiment in a test tube or an X-ray analysis, it can be decided whether or not the promoter is included in the DNA segment.
However, these methods have problems of an increase in testing time and cost. Particularly, the X-ray analysis requires a safety measure.

Therefore, instead of these methods, there is proposed a method of preparing DNA segments constructed with 4 nucleotide symbols A, T, G, and C as a discrete value data in a computer and performing a calculation process for deciding the existence of the promoters. Such a method is very important in order to process a large number of DNA segments at a high speed and low cost.

Such a method of deciding the existence of the promoter in a DNA segment constructed with a nucleic symbol sequence A, T, G, and C may be considered to be a good method, but this is not very simple in reality. This is because there is a large variation in the promoter patterns. For example, a portion of nucleotides constituting the promoters may be different from each other, or the whole lengths and positions of the promoters may be different from each other. Therefore, conventionally, such a method for transforming a discrete symbol sequence of A, T, G, and C into a continuous value and scrutinizing the resulting patterns has been employed.

For example, there are a method using neural networks (see Non-Patent Document 1), and a method using a combination of the neural networks and the expectation-maximization algorithm (EM algorithm) (see Non-Patent Document 2). These methods are described also in a well-known monograph (see Non-Patent Document 3) on bioinformatics.

Besides the referred non-patent methods, there is a class of chemical classification apparatus for classifying the information indicating a change in an amount of plural types of chemicals (including genes and by-products of genes) with a high accuracy. Such an apparatus includes the principal component analysis (PCA), and often the independent component analysis (ICA) is further used (see Patent Document 1). Unlike the present invention, however, these apparatuses are not applicable to the recognition or the prediction of discrete symbol patterns such as promoters.

A document about a homology score used for a process according to the second embodiment of the present invention is provided as a reference (see Non-Patent Document 4).

Patent Document 1 Japanese Patent Application Publication No. 2003-141102 (claim 1, Abstract)

Non-Patent Document 1 I. Mahadevan and I. Ghosh, "Analysis Of *E. Coli* Promoter Structures Using Neural Networks", Nucleic Acids Research, 1994, vol. 22, p. 2158-2165

Non-Patent Document 2 Q. Ma, T. L. Wang, D. Shasha, and C. H. Wu, "DNA Sequence Classification Via An Expectation Maximization Algorithm And Neural networks: A Case Study", IEEE Transactions on Systems, Man and Cybernetics, Part-C: Applications and Reviews, 2001, vol. 31, p. 468-475

Non-Patent Document 3 D. W. Mount, "Bioinformatics: Sequence And Genome Analysis", Cold Spring Harbor Laboratory Press, 2001 ("Bioinformatics" translated by Yasushi Okazaki and Hidemasa Bono, Medical Science International, 2002)

Non-Patent Document 4 Martin E. Mulligan, Diane K. Hawley, Robert Entriken, William R. McClure, "*Escherichia Coli* Promoter Sequences Predict In Vitro RNA Polymerase Selectivity", Nucleic Acids Research, 1984, vol. 12, p. 789-800

DISCLOSURE OF THE INVENTION

Problems to be Solved by the Invention

As described above, in such a promoter analysis using a biological experiment in a test tube or an X-ray analysis, it is difficult to process a large amount of data in terms of processing time and economic factors. Therefore, instead of these analyses, a computer-aided promoter analysis using a neural network method or an expectation-maximization algorithm (EM algorithm) has been provided. In such a computer-aided promoter analysis, however, a high recognition rate cannot always be obtained. Therefore, a high performance computer-aided promoter analysis has been required.

Although the difficulty of the computer-aided promoter analysis results from the diversity in pattern of a promoter in a DNA sequence, this obstacle is not limited to the analysis of the promoter in the DNA sequence. In general, when a feature pattern having variety is extracted from a sequence constructed with a finite number of discrete symbols, the same problem is caused from the diversity. Therefore, there is a need to recognize a feature pattern in a sequence constructed with a finite number of discrete symbols as well as a promoter in a DNA sequence with a high accuracy.

The present invention provides a feature pattern recognition system, method, and program capable of recognizing feature patterns in a sequence with a high accuracy.

Means for Solving the Problems

According to an aspect of the present invention, there is provided a feature pattern recognition system for deciding whether or not one of multiple types of known feature patterns that are found in advance and similar to each other or a new feature pattern that is similar to the known feature pattern is included in a sequence constructed with a finite number of discrete symbols, a segment thereof, or a test segment extracted from the sequence or the segment, comprising: symbol-frequency table storage means for storing a symbol-frequency table generated by obtaining a symbol frequency for each of multiple types of the discrete symbols reflecting sequence positions in the feature patterns by using the multiple types of known feature patterns and by corresponding the symbol frequencies to the sequence positions and the types of the discrete symbols in the feature patterns; separation matrix storage means for storing a separation matrix, as a matrix for performing inverse transformation of a basis matrix including feature elements representing the feature patterns, generated by converting to numerals the multiple types of known feature patterns and the multiple types of non-feature patterns that are different from the known feature patterns according to the sequence positions and the types of the discrete symbols by using the symbol-frequency table, by binding the numerals to generate a training data matrix, and by performing an independent component analysis or a principal component analysis by using the training data matrix; test data-generating means for generating test data by converting to numerals the to-be-decided sequence, the segment thereof, or the test segment extracted from the sequence or the segment according to the sequence positions and the types of the discrete symbols by using the symbol-frequency table stored in the symbol-frequency table storage means; separation processing means for obtaining separation data or a separation data matrix in which a plurality of the separation data are bound by performing a matrix calculation of multiplying the separation matrix stored in the separation matrix storage means with the test data or a test data matrix in which a plurality of the test data are bound; and decision means for deciding whether or not one of the multiple types of the known feature patterns or the new feature pattern similar to the known feature patterns is included in the to-be-decided sequence, the segment thereof, or the test segment extracted from the sequence or the segment or deciding a degree of existence thereof by using values of feature decision elements assigned according to internal-matrix positions of the feature elements included in the basis matrix among elements constituting the separation data or the separation data matrix obtained by the separation processing means. A set of sequences, each of which is constructed with a finite number of discrete symbols, a segment thereof, or a test segment extracted from the sequence or the segment, may be applied in batch to the feature pattern recognition system for the recognition of each sequence.

Here, the "feature pattern" includes, for example, a promoter or an enhancer in a DNA sequence, a motif in an amino acid sequence constituting a protein, a pattern in a mixed sequence of the DNA sequence and the amino acid sequence, or the like. Besides the feature pattern in such a biological sequence, the "feature pattern" may be various feature patterns in various sequences such as a linguistic sequence, an acoustic sequence, a geological sequence, a astronomical sequence, a physical sequence, or the like. In other words, the "feature pattern" in the present invention includes a feature pattern in a sequence constructed with a finite number of discrete symbols. The phrase "the feature patterns are similar" means that, in case of a biological sequence, the feature patterns are in a homologous group. In turn, a newly found feature pattern having a similarity can be added to in the homologous group.

The "discrete symbols" may be characters (alphabets, the Greek alphabets, Chinese characters, figures, Hiragana, Katakana, or the like), drawings, symbols, or a combination thereof. For example, "discrete symbols" constituting a DNA sequence are standard nucleotide symbols represented by four alphabets A (Adenine), T (Thymine), G, (Guanine), and C (Cytosine) (however, non-standard symbols may be used). In addition, a symbol ("−"; minus sign) representing gaps that are inserted in a length alignment process are included in the "discrete symbols". In addition, "discrete symbols" constituting an amino acid sequence are standard amino acid abbreviation symbols including twenty alphabet letters such as A (Alanine), R (Arginine), and N (Asparagine) (however, a group or non-standard symbols may be used) and minus sign representing the gaps.

The phrase "a sequence, a segment thereof, or a test segment extracted from the sequence or the segment" include a case where the sequence or the segment thereof may be directly processed to generate the test data used for the processes of the separation processing means and the decision means and a case where the "test segment extracted from the sequence or the segment" may be processed.

The "feature decision elements assigned according to internal-matrix positions of the feature elements included in the basis matrix" has the following meaning. In a case where the feature elements indicating a property of the feature pattern appear in the first column (actually, it can be verified from a predicted basis matrix) of the basis matrix (that is, a case where the first column is at an internal-matrix position of the feature element), the "feature decision elements assigned according to internal-matrix positions of the feature elements included in the basis matrix" are the elements (in case of a vector column, the first element) of the first row of the separation data (column vector) or the separation data matrix in which a plurality of the separation data are bound, that are strongly influenced by elements disposed in the first column of the basis matrix in a matrix calculation (see FIGS. 39 and 40 described later). For example, in a case where multiple columns (for example, the first column, the second column, the fifth column, . . . ) of feature elements appear in the basis matrix, the feature decision elements become multiple rows (for example, the first row, the second row, the fifth row, . . . ) of elements (see FIGS. 44 and 49 described later). In the specification, the case where the feature elements indicating a property of the feature pattern "appear" in the first column of the basis matrix (actually, a basis matrix predicted in a calculation process) includes a case where a system designer forcibly adds a training tool so that the feature element indicating a property of the feature pattern best can appear in the first column. Similarly, in a case where the feature elements appear in another column, the feature elements may be forced to appear. Accordingly, it may include a case where the feature decision elements in the separation data (column vector) or the separation data matrix corresponding to the feature elements in the basis matrix may be also forcibly set to the first row (in case of a column vector, the first element) or other specific positions.

The decision process of the "decision means" includes the hard limited decision of deciding whether or not the feature pattern exists and soft decision of deciding a degree (probability) of existence of the feature pattern. For example, in a case where the feature decision elements are elements included in only one row, the former hard limited decision is performed by deciding at which side of a predetermined threshold exists the value of the feature decision elements, and the latter soft decision is performed by deciding a degree of the magnitude of the values of the feature-decision element. In a case where the feature-decision elements are elements of multiple rows, a value indicating the similarity measure of the column vector constructed with multiple rows of feature-decision elements in the separation data or the separation data matrix obtained by the separation processing means to each of the vectors constructed with the values of the feature decision elements of true data corresponding portions in the separation data matrix obtained together with the separation matrix in the training step. Next, the former hard limited decision is performed by deciding at which side of a predetermined threshold exists the value indicating the calculated similarity measure, and the latter soft decision is performed by deciding a degree of magnitude of the value indicating the calculated similarity measure. In the latter soft decision, as the decision results, "very highly probable feature pattern", "highly probable feature pattern", "probable feature pattern", "very highly improbable feature pattern", "highly improbable feature pattern", "improbable feature pattern", "indeterminable", and the like may be output. The number of levels in the decision may be arbitrarily set. In addition, the decision results may be output in such a manner that "the probability of the feature pattern is so-and-so %". In the later-described correlation decision, the above-described construction may be used.

As described above, according to the present invention, each of the discrete symbols constituting a to-be-decided sequence is converted to numerals by using symbol frequencies according to sequence positions or types of the discrete symbols, and it is decided whether or not feature patterns exist in the sequence by using a separation matrix obtained by performing an independent component analysis (ICA) or a principal component analysis (PCA). Therefore, in comparison with a computer-aided promoter analysis using a conventional neural network method or an expectation-maximization algorithm (EM algorithm), it is possible to improve a feature pattern recognition accuracy for a promoter or like. In addition, in comparison with a promoter analysis using a biological experiment in a test tube or an X-ray analysis, it is possible to implement a feature pattern analysis having advantages in view of processing time and cost. Accordingly, the objects of the present invention can be achieved.

In the aforementioned feature pattern recognition system, allowably, the feature patterns are hierarchical feature patterns that includes a plurality of partial patterns located at different regions, and region positions of the partial patterns in the feature patterns and a whole length of the feature patterns include multiple types of region positions and multiple types of lengths according to a difference of the types of the feature patterns, wherein the symbol-frequency table storage means is whole-pattern symbol-frequency table storage means for storing a whole-pattern symbol-frequency table generated by equalizing whole pattern lengths of the multiple types of the known feature patterns to a constant length by inserting gaps or removing discrete symbols of regions other than the partial patterns, by obtaining the symbol frequency for each type of the discrete symbols including the gaps at each of the sequence positions in the feature patterns by using the multiple types of the known feature patterns of which whole pattern lengths are equalized, and by corresponding the symbol frequencies to the sequence positions in the feature patterns and the types of the discrete symbols including the gaps, wherein the separation matrix storage means is whole-pattern separation matrix storage means for storing a whole-pattern separation matrix obtained by performing the independent component analysis or the principal component analysis by using a whole-pattern training data matrix generated from the multiple types of the known feature patterns of which whole pattern lengths are equalized and the multiple types of non-feature patterns of which lengths are equalized to the lengths of the multiple types of the known feature patterns, wherein the feature pattern recognition system further comprises: partial-pattern symbol-frequency table storage means for storing a partial-pattern symbol-frequency table obtained for each partial pattern in each region; partial-pattern separation matrix storage means for storing a partial-pattern separation matrix obtained for each partial pattern in each region; and partial-pattern separation data matrix storage means for storing elements of at least true data corresponding portions of a partial-pattern separation data matrix that is obtained together with the partial-pattern separation matrix in a training step for each partial pattern in each region, wherein the partial-pattern symbol-frequency table storage means stores a partial-pattern symbol-frequency table generated by obtaining, for each partial pattern in each region included in the known feature patterns, the symbol frequencies for each of the types of the discrete symbols at each sequence position in the partial patterns by using the multiple types of the known partial patterns and by corresponding the symbol frequencies to the sequence positions in the partial patterns and the types of the discrete symbols, wherein the partial-pattern separation matrix storage means stores, for each partial pattern in each region included in the known feature patterns, a partial-pattern separation matrix as a matrix for performing inverse transformation of a partial-pattern basis matrix including feature elements representing the partial patterns generated by converting to numerals the multiple types of known partial patterns and multiple types of non-partial patterns that are different from the known partial patterns according to the sequence positions and the types of the discrete symbols by using the partial-pattern symbol-frequency table, by binding the numerals to generate a partial-pattern training data matrix, and performing an independent component analysis or a principal component analysis by using the partial-pattern training data matrix, wherein the partial-pattern separation data matrix storage means stores elements of at least true data corresponding portions of a partial-pattern separation data matrix obtained as a result of multiplication of the partial-pattern separation matrix with the partial-pattern training data matrix when the partial-pattern separation matrix is obtained by performing the independent component analysis or the principal component analysis, and wherein the test data-generating means comprises: partial pattern putative data-generating means for generating a plurality of partial pattern putative data by selecting, for each partial pattern in each region, a plurality of partial pattern putative sequences of which the lengths are the same as that of the partial pattern and of which positions are shifted from each other among the to-be-decided sequence, the segment thereof, or the test segment extracted from the sequence or the segment, and by converting to numerals a plurality of the partial pattern putative sequences according to the sequence positions and the types of the discrete symbols by using the partial-pattern symbol-frequency table stored in the partial-pattern symbol-frequency table storage means; partial pattern putative data-associated separation data generating means for generating a plurality of partial pattern putative data-associated separation data or a partial pattern putative data-associated separation data matrix in which a plurality of the partial pattern putative data-associated separation data are bound by performing a matrix calculation of multiplying the partial-pattern separation matrix stored in the partial-pattern separation matrix storage means with each of the partial pattern putative data generated by the partial pattern putative data-generating means or a partial pattern putative data matrix in which a plurality of the partial pattern putative data are bound; partial pattern-corresponding sequences selection means for obtaining partial pattern putative data-associated separation data that are closest to column vectors of true data corresponding portions of the partial-pattern separation data matrix among a plurality of the partial pattern putative data-associated separation data generated by the partial pattern putative data-associated separation data generating means and selecting the partial pattern putative sequences corresponding to the obtained partial pattern putative data-associated separation data as partial pattern-corresponding sequences included in feature pattern putative sequences that are candidates of the feature pattern; feature pattern putative sequence selection means for selecting the feature pattern putative sequence based on the partial pattern-corresponding sequences of the regions selected by the partial pattern-corresponding sequences selection means; alignment processing means for performing an alignment process for equalizing lengths of the feature pattern putative sequences selected by the feature pattern putative sequence selection means to a constant length by inserting gaps or removing the discrete symbols of regions other than the partial patterns while each of the partial pattern-corresponding sequences of each region selected by the partial pattern-corresponding sequences selection means is maintained to be in a one-body state; and feature pattern putative sequence numerical conversion means for generating the test data by converting to numerals the feature pattern putative sequences of which lengths are equalized by the alignment processing means according to the sequence positions and the types of the discrete symbols including the gaps by using the whole-pattern symbol-frequency table stored in the whole-pattern symbol-frequency table storage means.

Here, the "column vectors of true data corresponding portions of the partial-pattern separation matrix" are true data corresponding portions constituting the partial-pattern separation matrix and true data corresponding portions among false data corresponding portions (see FIG. 21 described later). The true data corresponding portions are the portions corresponding to portions where the partial-patterns (that is, true data) are disposed in the partial-pattern training matrix which is used to obtain the partial-pattern separation data matrix together with the partial-pattern separation matrix (see FIGS. 10 and 15 described later). The false data corresponding portions are the portions corresponding to portions where the non-partial patterns (that is, false data) are disposed in the partial-pattern training data matrix.

In addition, the meaning of "obtaining the symbol frequencies according to the types of the discrete symbols including the gaps" includes a case where, if the alignment process is performed by inserting the gaps, the inserted gaps are included in the discrete symbols to obtain the symbol frequencies (see FIG. 19 described later). In a case where the alignment process is performed by removing the discrete symbols in regions other than the partial patterns, since the gaps are not inserted, the symbol frequency of the gaps is not needed to be obtained.

In such a construction of generating the partial-pattern symbol-frequency table for each of the partial patterns included in the hierarchical feature pattern and performing a process using the partial-pattern separation matrix obtained by performing the independent component analysis (ICA) or the principal component analysis (PCA), the partial patterns are recognized from the sequence, so that the feature pattern including the partial patterns can be recognized. As a result, the hierarchical feature patterns in which there is a variation in the region positions of the partial patterns in the feature pattern and the whole length of the feature pattern also can be recognized. In addition, in a case where each of the partial patterns is recognized from the sequence, since each of the partial-pattern separation matrices obtained by performing the independent component analysis (ICA) or the principal component analysis (PCA) is used, the positions of the partial patterns can be specified with a high accuracy. Accordingly, it is possible to recognize the hierarchical feature pattern with a high accuracy.

In such a construction capable of recognizing the hierarchical feature pattern, when the multiple types of the non-feature patterns of which whole lengths are equalized in order to construct the whole-pattern training data matrix which is used to obtain the whole-pattern separation matrix stored in the whole-pattern separation matrix storage means, since random data or non-promoter segments extracted from known database can be used to generate the matrices, the process of finding the partial-pattern corresponding sequences by using the partial-pattern separation matrix and the partial-pattern separation data matrix may not be performed. Since the data which are subjected to the same process as the test step data is used as the training data, however, it is preferable that the process for finding the partial-pattern corresponding sequences by using the partial-pattern separation matrix and the partial-pattern separation data matrix is performed as follows. Namely, in the test step, the to-be-decided sequence cannot be identified as a feature pattern or a non-feature pattern. Therefore, all the to-be-decided sequences are equally subjected to a process including the partial pattern-corresponding sequence selection process using the partial-pattern separation matrix and the partial-pattern separation data matrix (see FIG. 36 described later) to generate the test data. Accordingly, in the training step, it is preferable that the partial pattern-corresponding sequence selection process (see FIGS. 20 to 23) using the partial-pattern separation matrix and the partial-pattern separation data matrix is performed as follows.

More specifically, as described above, in a construction capable of recognizing the hierarchical feature pattern, preferably, the multiple types of the non-feature patterns of which whole pattern lengths are equalized to constitute the whole-pattern training data matrix used to obtain the whole-pattern separation matrix stored in the whole-pattern separation matrix storage means are generated by: generating a plurality of partial pattern putative data by selecting, for each partial pattern in each region, a plurality of partial pattern putative sequences of which lengths are the same as that of the partial pattern and of which positions are shifted from each other among non-feature patterns-generating sequences prepared to generate the non-feature patterns, and by converting to numerals a plurality of the partial pattern putative sequences according to the sequence positions and the types of the discrete symbols by using the partial-pattern symbol-frequency table; generating a plurality of partial pattern putative data-associated separation data or a partial pattern putative data-associated separation data matrix in which a plurality of the partial pattern putative data-associated separation data are bound by performing a matrix calculation of multiplying the partial-pattern separation matrix with each of the partial pattern putative data or a partial pattern putative data matrix in which a plurality of the partial pattern putative data are bound; obtaining partial pattern putative data-associated separation data that are closest to column vectors of true data corresponding portions of the partial-pattern separation data matrix among the generated plurality of the partial pattern putative data-associated separation data and selecting the partial pattern putative sequences corresponding to the obtained partial pattern putative data-associated separation data as partial pattern-corresponding sequences included in the non-feature patterns; selecting the non-feature patterns based on the selected partial pattern-corresponding sequences of the regions; and performing an alignment process for equalizing lengths of the selected non-feature patterns to a constant length by inserting gaps or removing the discrete symbols of regions other than the partial patterns while each of the partial pattern-corresponding sequences of each region is maintained to be in a one-body state.

In this case, preferably, the multiple types of the non-feature patterns are generated by obtaining the partial pattern putative data-associated separation data in which a similarity measure of the partial pattern putative data-associated separation data to a set of the column vectors of true data-corresponding portions of the partial pattern separation data matrix is maximized, when obtaining the partial pattern putative data-associated separation data that are closest to column vectors of true data-corresponding portions of the partial-pattern separation data matrix among a plurality of the partial pattern putative data-associated separation data.

In addition, as described above, in a construction capable of recognizing the hierarchical feature pattern, preferably, the multiple types of the non-feature patterns are generated by obtaining the partial pattern putative data-associated separation data in which a similarity measure of the partial pattern's putative data-associated separation data to a set of the column vectors of true data's corresponding portions of the partial pattern separation data matrix is maximized, when obtaining the partial pattern's putative data-associated separation data that are closest to column vectors of true data's corresponding portions of the partial-pattern separation data matrix among a plurality of the partial pattern putative data-associated separation data.

The similarity measure may include a summation of inner products of the partial pattern's putative data-associated separation data to the column vectors of the true data-corresponding portions of the partial pattern separation data matrix, or like that which reflects the patterns' resemblance.

In such a construction of performing a process for selecting the partial pattern-corresponding sequence from a plurality of the partial pattern putative sequences by using the similarity measure, for example, a summation of inner products, when the partial pattern-corresponding sequence is selected from a plurality of the partial pattern putative sequences (see FIGS. 20 and 22 described later) selected from the non-feature pattern-generating sequences or from a plurality of the partial pattern putative sequences (see FIG. 36 described later) selected from test segment, a more probable partial pattern putative sequence can be selected as the partial pattern-corresponding sequences, it is possible to search for the partial pattern with a high accuracy. Moreover, it is possible to search for the feature pattern with a high accuracy.

In the aforementioned feature pattern recognition system, the decision means may be constructed with a decision process using only one (one row) feature decision element according to an appearance type of the feature element in the basis matrix. Alternatively, the decision process may be performed by using plurality (multiple rows) feature decision elements. Detailed constructions thereof are exemplified as follows.

In the aforementioned feature pattern recognition system, when one column of the feature elements appears in the basis matrix, the decision means may decide at which side of a predetermined threshold, values of the feature decision element of the separation data or the separation data matrix obtained by the separation processing means exist, or may decide the magnitudes of the values thereof, thereby deciding whether or not one of the multiple types of the known feature patterns or the new feature pattern similar to the known feature patterns is included in the to-be-decided sequence, the segment thereof, or the test segment extracted from the sequence or the segment or deciding a degree of existence thereof.

In the aforementioned feature pattern recognition system, when one column of the feature elements appears in the basis matrix and multiple columns of the feature elements appear in the basis matrix, and multiple rows of elements constituting the separated data or the separated data matrix obtained by the separation processing means may be used as the feature decision elements, the decision means decides whether or not one of the multiple types of the known feature patterns or the new feature pattern similar to the known feature patterns is included in the to-be-decided sequence, the segment thereof, or the test segment extracted from the sequence or the segment or decides a degree of existence thereof by using values of the feature decision elements of the multiple rows of the separated data or the separated data matrix obtained by the separation processing means.

Here, the phrase "by using the values of the multiple rows of the feature decision elements" intends to include a case where a decision process may be performed by using only the values of the feature decision elements in the separation data or the separation data matrix obtained by calculating the average value of the values of a plurality of the feature decision elements or a summation thereof in the separation processing means (that is, by using only the values of the feature decision elements obtained in the test step) and a case where a decision process may be performed by using the values of the feature decision elements in the separation data or the separation data matrix obtained by the separation processing means and the values of the feature decision elements of true data-corresponding portions in the separation data matrix that is obtained together with the separation matrix in the training step. Similarly to the latter case, in a case where the values of the feature decision elements of true data-corresponding portions in the separation data matrix is used, the following constructions may be used.

In the aforementioned feature pattern recognition system, the decision means may calculate a value indicating a similarity measure of a column vector constructed with the values of the feature decision elements of the multiple rows of the separation data or the separation data matrix obtained by the separation processing means to column vectors constructed with values of feature decision elements of true data-corresponding portions of a separation data matrix that is obtained together with the separation matrix in the training step and decide at which side of a predetermined threshold exists the calculated value indicating the similarity measure or decides a magnitude of the value thereof, thereby deciding whether or not one of the multiple types of the known feature patterns or the new feature pattern similar to the known feature patterns is included in the to-be-decided sequence, the segment thereof, or the test segment extracted from the sequence or the segment or deciding a degree of existence thereof.

In such a construction of calculating the value indicating the similarity measure, in order to avoid excessive concentration to a specific column vector (that is, closeness to a specific feature pattern) among the column vectors constructed with values of the feature decision elements of true data corresponding portions in the separation data matrix which is obtained together with the separation matrix in the training step, the following construction is preferred. Namely, preferably, the decision means calculates, as the value indicating the similarity measure, a value indicating a similarity measure of a column vector constructed with the values of the feature decision elements of the multiple rows of the separation data or the separation data matrix obtained by the separation processing means to a set of column vectors constructed with values of feature decision elements of true data corresponding portions of a separation data matrix that is obtained together with the separation matrix in the training step.

As an detailed example of the "process for calculating the value indicating the similarity measure to the set of the column vectors", there is a process for calculating a value of an inner product of the column vectors constructed with the values of the separation data obtained by the separation processing means or the multiple rows of the feature decision element in the separation data matrix to a centroid vector from each of the column vectors constructed with the values of the feature decision elements of true data-corresponding portions in the separation data matrix that is obtained together with the separation matrix in the training step.

Here, the process for calculating "the value of inner product to the centroid vector" and the "equivalent value" is a process for calculating and utilizing values of inner products of the column vector constructed with the values of the multiple rows of the feature decision elements in the separation data or the separation data matrix obtained by the separation processing means to the column vectors constructed with the values of the feature decision elements of true data-corresponding portions in the separation data matrix that is obtained together with the separation matrix in the training step, and calculating and utilizing an average of the inner products.

The process for calculating the value indicating the similarity measure is not limited to the aforementioned centroid calculation. For example, a more general process such as Mahalanobis distance and like that may be used.

In addition, as described above, in a construction capable of recognizing the hierarchical feature pattern, preferably, the test data-generating means generates a plurality of test data for an arbitrary one test segment by selecting the feature pattern putative sequences while shifting by one discrete symbol among the to-be-decided sequence, the segment thereof, or the test segment extracted from the sequence or the segment, performing an alignment process for equalizing lengths of the selected feature pattern putative sequences to a constant length by inserting gaps or removing discrete symbols of regions other than the partial patterns, and converting to numerals the feature pattern putative sequences of which lengths are equalized according to the sequence positions and the types of the discrete symbols including the gaps by using the whole-pattern symbol-frequency table stored in the whole-pattern symbol-frequency table storage means, wherein the separation processing means obtains, for each test segment, a plurality of separation data or a separation data matrix in which a plurality of the separation data are bound by performing a matrix calculation of multiplying the whole-pattern separation matrix with a plurality of the test data generated by the test data-generating means or a test data matrix in which a plurality of the test data are bound, and wherein the decision means decides at which side of a predetermined threshold exists a value of each of the feature decision elements assigned according to internal-matrix positions of the feature elements included in the basis matrix among elements constituting a plurality of the separation data or the separation data matrix for the arbitrary one test segment obtained by the separation processing means, obtains a value of the feature decision element of which absolute value of a difference from the threshold is largest or of which degree of feature pattern closeness is highest among the values of feature decision elements which are decided to represent the feature pattern or a degree of the feature pattern closeness, and recognizes that the feature pattern putative sequence corresponding to the test data assigned with the obtained value of the feature decision element is one of multiple types of the known feature patterns or a new feature pattern that similar to the known feature patterns.

In addition, as described above, in a construction capable of recognizing the hierarchical feature pattern, preferably (see FIG. 36 described later), the test data-generating means generates a plurality of test data for an arbitrary one test segment by selecting the feature pattern putative sequences while shifting by one discrete symbol among the to-be-decided sequence, the segment thereof, or the test segment extracted from the sequence or the segment, performing an alignment process for equalizing lengths of the selected feature pattern putative sequences to a constant length by inserting gaps or removing discrete symbols of regions other than the partial patterns, and converting to numerals the feature pattern putative sequences of which lengths are equalized according to the sequence positions and the types of the discrete symbols including the gaps by using the whole-pattern symbol-frequency table stored in the whole-pattern symbol-frequency table storage means, wherein the separation processing means obtains, for each test segment, a plurality of separation data or a separation data matrix in which a plurality of the separation data are bound by performing a matrix calculation of multiplying the whole-pattern separation matrix with a plurality of the test data generated by the test data-generating means or a test data matrix in which a plurality of the test data are bound, and wherein the decision means calculates a value indicating a similarity measure of each of column vectors constructed with the values of the feature decision elements of multiple rows assigned according to internal-matrix positions of the feature elements of multiple columns included in the basis matrix among elements constituting a plurality of the separation data or the separation data matrix for the arbitrary one test segment obtained by the separation processing means to column vectors constructed with values of feature decision elements of true data-corresponding portions of a separation data matrix that is obtained together with the whole-pattern separation matrix in the training step, decides in which side of a predetermined threshold exists a value indicating the similarity measure or decides a magnitude of the value thereof, obtains a value indicating the similarity measure of which the absolute value of a difference from the threshold is largest or of which degree of feature pattern closeness is highest among the values of the similarity measure which are decided to represent the feature pattern or a degree of the feature pattern closeness, and recognizes that the feature pattern putative sequence corresponding to the test data assigned with the obtained value indicating the similarity measure is one of multiple types of the known feature patterns or a new feature pattern that similar to the known feature patterns.

In such a case where the feature pattern putative sequences in the test sequence are selected while shifting by one discrete symbol (see FIG. 36 described later) and changing the length at each position, and a process of selecting one sequence that is recognized as a feature pattern from a plurality of the feature pattern putative sequences (however, any one feature pattern may not be recognized, which means that two or more feature pattern putative sequences are not recognized as the feature pattern) is performed, under the condition that the test segment are set to a suitable length, it is possible to recognize the feature pattern with a high accuracy.

In addition, as described above, in a construction capable of recognizing the hierarchical feature pattern, preferably, when the partial patterns of each region included in the hierarchical feature patterns have a correlation with specific-site neighborhood sequences including a specific site of the sequence, the feature pattern recognition system may further comprise correlation training result storage means for storing information including a correlation training result obtained by training in advance as information used to decide the correlation of the partial pattern of each region with the specific-site neighborhood sequences, wherein the partial pattern putative data-generating means of the test data-generating means selects a plurality of the partial pattern putative sequences for each of the partial patterns of each region based on a relative positional relation to the specific site or a relative positional relation to partial pattern putative sequences of other regions defined according to the relative positional relation to the specific site, and wherein the feature pattern putative sequence selection means of the test data-generating means decides the existence of a correlation or a degree of the correlation between the partial pattern-corresponding sequences of each region selected by the partial pattern-corresponding sequences selection means of the test data-generating means and the specific-site neighborhood sequences by using the information including the correlation training result stored in the correlation training result storage means and, if there is no correlation or if the degree of the correlation is low, does not perform a decision process for the feature pattern putative sequence based on the partial pattern-corresponding sequences of each region and the specific site in the specific-site neighborhood sequences.

The "specific site" is a discrete symbol which exists in a sequence and is disposed at a position that has a property or meaning. A transcription start site in the vicinity of a gene coding region in a DNA sequence can be exemplified.

In such a construction of performing the correlation-decision process for deciding a correlation between the partial pattern-corresponding sequences and the specific-site neighborhood sequences in each region, if there is no or low correlation between the partial pattern-corresponding sequences and the specific-site neighborhood sequences, the selected sequences based on the specific site in the partial pattern-corresponding sequences and the specific-site neighborhood sequences may be removed from the feature pattern putative sequence. As a result, it is possible to further improve the feature pattern recognition accuracy. In addition, when it is decided to be no or low correlation, since the sequences selected based on the specific site in the partial pattern-corresponding sequences and the specific-site neighborhood sequences are not used as the feature pattern putative sequence, there is no need to generate the test data for the sequences. In addition, since there is no need to perform the separation process of the separation processing means and decision process of the decision means, it is possible to reduce a processing time.

In addition, the "information including the correlation training result" stored in the "correlation training result storage means" may be information obtained in the pre-training using a neural network method. In terms of improvement of the correlation decision accuracy, however, it is preferable that the information is obtained in the pre-training using the independent component analysis (ICA) or the principal component analysis (PCA) as follows.

As described above, in a construction of performing the correlation-decision process for deciding a correlation between the partial pattern-corresponding sequences of each region and the specific-site neighborhood sequence, preferably, the correlation training result storage means comprises: correlation-decision symbol-frequency table storage means for storing a correlation-decision symbol-frequency table generated by binding the known partial patterns of at least one region among a plurality of regions included in the known feature patterns with known specific-site neighborhood sequences to generate multiple types of correlation-binding sequences, obtaining a symbol frequency for each type of the discrete symbols at each sequence position in the correlation-binding sequences by using multiple types of correlation-binding sequences, and corresponding the symbol frequencies to the sequence positions and the types of the discrete symbols in the correlation-binding sequences; and correlation-decision separation matrix storage means for storing a correlation-decision separation matrix used for a correlation-decision process for deciding the correlation between the partial patterns of each region and the specific-site neighborhood sequences, wherein the correlation-decision separation matrix storage means stores a correlation-decision separation matrix, as a matrix for performing inverse transformation of a correlation-decision basis matrix including feature elements representing correlation-binding sequences, generated by converting to numerals correlation-binding sequences generated by binding the known partial patterns of at least one region among a plurality of the regions with the known specific-site neighborhood sequences and non-correlation-binding sequences generated by binding the known partial patterns of at least one region among a plurality of the regions with non-specific-site neighborhood sequences different from the known specific-site neighborhood sequences according to the sequence positions and the types of the discrete symbols by using the correlation-decision symbol-frequency table, binding the numerals to generate a correlation-decision training data matrix, and performing an independent component analysis or a principal component analysis by using the correlation-decision training data matrix, and wherein the feature pattern putative sequence selection means of the test data-generating means, when deciding the existence of a correlation or a degree of the correlation between the partial pattern-corresponding sequences of each region and the specific-site neighborhood sequences, generates correlation-decision sequences by binding the partial pattern-corresponding sequences of at least one region among a plurality of the regions with the specific-site neighborhood sequences, converts to numerals the correlation-decision sequences according to the sequence positions and the types of the discrete symbols by using the correlation-decision symbol-frequency table stored in the correlation-decision symbol-frequency table storage means to generate correlation-decision data, performs a correlation-decision separation process for obtaining correlation-decision separation data or a correlation-decision separation data matrix in which a plurality of the correlation-decision separation data are bound by performing a matrix calculation of multiplying the correlation-decision separation matrix stored in the correlation-decision separation matrix storage means with the correlation-decision data or a correlation-decision data matrix in which a plurality of the correlation-decision data are bound, and decides the existence of the correlation or a degree of the correlation by using a value of the correlation-decision element assigned according to internal-matrix positions of the feature elements included in the correlation-decision basis matrix among the correlation-decision separation data obtained in the correlation-decision separation process or the elements constituting the correlation-decision separation data matrix.

Here, "the known partial patterns of at least one region among a plurality of regions" may denote a case where, at the time of generating the correlation-decision symbol-frequency table or at the time of obtaining the correlation-decision separation matrix in the training step, in all the regions, the known partial patterns and the known specific site neighborhood sequences are bound to generate the correlation-binding sequence and a case where in a portion of the region, the known partial patterns and the known specific site neighborhood sequences are bound to generate the correlation-binding sequence. Similarly, "the partial pattern-corresponding sequences of least one region among a plurality of regions" may denote a case where, in the test step, in all the region, the partial pattern-corresponding sequences and the specific site neighborhood sequences are bound to generate the correlation-decision sequences and a case where in a portion of the region, the partial pattern-corresponding sequences and the specific site neighborhood sequence are bound to generate the correlation-decision sequences. In view of an improvement in the correlation decision accuracy, it is preferable that the known partial pattern in all the regions or the partial pattern-corresponding sequences in all the regions are used to generate the correlation-binding sequence or the correlation-decision sequences.

In addition, the "correlation-decision training data matrix" is generated by converting to numerals the correlation-binding sequence generated by binding the known partial patterns with the known specific-site neighborhood sequences in at least one region among a plurality of regions and the non-correlation-binding sequence generated by binding the known partial patterns with the non-specific-site neighborhood sequences different from the known specific-site neighborhood sequence by using the correlation-decision symbol-frequency table according to sequence positions and types of the discrete symbols and binding the numerals (see FIG. 30). However, the "correlation-decision training data matrix" denotes a case where at least the numerical conversion of the correlation-binding sequence and the non-correlation-binding sequence is included in the correlation-decision training data matrix. For example, in addition to the numerical conversion of the correlation-binding sequence and the non-correlation-binding sequence, random sequences (sequences not including known partial patterns) may be converted to numerals and bound to generate the correlation-decision training data matrix.

In such a construction of performing the correlation-decision process using the correlation-decision separation matrix obtained in the pre-training using the independent component analysis (ICA) and the principal component analysis (PCA), it is possible to improve the correlation decision accuracy.

As described above, in a construction of performing a correlation-decision process by using a correlation-decision separation matrix obtained in the pre-training using an independent component analysis (ICA) or a principal component analysis (PCA), the feature pattern putative sequence selection means of the test data-generating means may decide the existence of a correlation or a degree of the correlation by deciding at which side of a predetermined correlation-decision threshold exists a value of the correlation-decision element. In addition, the correlation-decision process may be performed by using values of multiple rows of the correlation-decision elements.

The aforementioned feature pattern recognition systems may be suitably applied to a case where the sequence is a DNA sequence, the discrete symbols are symbols A, T, G, and C representing nucleotides constituting the DNA sequence or substitute symbols thereof, and the feature pattern is a promoter in the DNA sequence.

Among the aforementioned feature pattern recognition systems, a system having a construction capable of recognizing the hierarchical feature pattern may be suitably applied to a case where the sequence is a DNA sequence, the discrete symbols are symbols A, T, G, and C representing nucleotides constituting the DNA sequence or substitute symbols thereof, the feature pattern is a promoter in the DNA sequence, and the partial patterns are a "−35 box" and a "−10 box" included in the promoter.

Among the aforementioned feature pattern recognition systems, a system having a construction of performing a correlation-decision process for deciding a correlation between the partial pattern-corresponding sequences of each region and the specific-site neighborhood sequence may be suitably applied to a case where the sequence is a DNA sequence, the discrete symbols are symbols A, T, G, and C representing nucleotides constituting the DNA sequence or substitute symbols thereof, the feature pattern is a promoter in the DNA sequence, the partial patterns are a −35 box and a −10 box included in the promoter, the specific site is a transcription start site of the DNA sequence, and the specific-site neighborhood sequences is a transcription-start-site neighborhood sequence.

The aforementioned feature pattern recognition system may be suitably applied to a case where the sequence is an amino acid sequence constituting a protein, the discrete symbols are symbols representing the amino acids constituting the amino acid sequence, and the feature pattern is a motif of the amino acid sequence.

In a case where there are multiple types of lengths in the feature patterns, when non-hierarchical feature patterns are recognized or when hierarchical feature patterns are recognized by using the same scheme as the non-hierarchical case, the following systems may be used.

In the aforementioned feature pattern recognition system, the lengths of the feature pattern include multiple types of lengths according to the difference in the types of the feature patterns, wherein the symbol-frequency table storage means stores a symbol-frequency table generated by equalizing the lengths of the multiple types of the known feature patterns to a constant length by inserting gaps, by obtaining the symbol frequency for each type of the discrete symbols including the gaps at each of the sequence positions in the feature patterns by using the multiple types of the known feature patterns of which lengths are equalized, and by corresponding the symbol frequencies to the sequence positions in the feature patterns and the types of the discrete symbols including the gaps, wherein the separation matrix storage means stores a separation matrix obtained by performing the independent component analysis or the principal component analysis by using a training data matrix generated from the multiple types of the known feature patterns of which lengths are equalized and the multiple types of non-feature patterns of which the lengths are equalized to the lengths of the multiple types of the known feature patterns, and wherein the test data generating means generates the test data by selecting putative sequences that become candidates of the feature patterns among the to-be-decided sequence, the segment thereof, or the test segment extracted from the sequence or the segment, performing an alignment process for equalizing lengths of the selected putative sequences to a constant length by inserting gaps, and converting to numerals the putative sequences of which lengths are equalized according to the sequence positions and the types of the discrete symbols including the gaps by using the symbol-frequency table stored in the symbol-frequency table storage means.

In this case, the "alignment process for equalizing the lengths of the putative sequences to a constant by inserting the gaps" may be performed by using a conventional standard tool such as BLAST for executing a conventional algorithm such as Clustal W. In addition, the alignment process may be performed by using a newly established rule. In addition, such a tool or rule may be used for an alignment process for equalizing the lengths of the known feature patterns to a constant length by inserting the gaps.

In such a construction of performing the alignment process, although there are a plurality of lengths in the feature pattern (a non-hierarchical feature pattern or a hierarchical feature pattern that is processed by using the same scheme as the non-hierarchical case), it is possible to recognize the feature patterns with a high accuracy.

In the aforementioned feature pattern recognition system, preferably, the test data-generating means generates a plurality of test data for an arbitrary one test segment by selecting the putative sequences while shifting by one discrete symbol and changing a length at each position among the to-be-decided sequence, the segment thereof, or the test segment extracted from the sequence or the segment, performing an alignment process for equalizing the lengths of a plurality of the selected putative sequences to a constant length by inserting gaps, and converting to numerals the putative sequences of which lengths are equalized according to the sequence positions and the types of the discrete symbols including the gaps by using the symbol-frequency table stored in the symbol-frequency table storage means, wherein the separation processing means obtains, for each test segment, a plurality of separation data or a separation data matrix in which a plurality of the separation data are bound by performing a matrix calculation of multiplying the separation matrix with a plurality of the test data generated by the test data-generating means or a test data matrix in which a plurality of the test data are bound, and wherein the decision means decides in which side of a predetermined threshold exists a value of each of the feature decision elements assigned according to internal-matrix positions of the feature elements included in the basis matrix among elements constituting a plurality of the separation data or the separation data matrix for the arbitrary one test segment obtained by the separation processing means, obtains a value of the feature decision element of which the absolute value of a difference from the threshold is largest or of which degree of feature pattern closeness is highest among the values of the feature decision elements which are decided to represent the feature pattern or a degree of the feature pattern closeness, and recognizes that the feature pattern putative sequence corresponding to the test data assigned with the obtained value of the feature decision element is one of multiple types of the known feature patterns or a new feature pattern that similar to the known feature patterns.

In the aforementioned feature pattern recognition system, the test data-generating means generates a plurality of test data for an arbitrary one test segment by selecting the putative sequences while shifting by one discrete symbol and changing a length at each position among the to-be-decided sequence, the segment thereof, or the test segment extracted from the sequence or the segment, performing an alignment process for equalizing lengths of a plurality of the selected putative sequences to a constant length by inserting gaps, and converting to numerals the putative sequences of which lengths are equalized according to the sequence positions and the types of the discrete symbols including the gaps by using the symbol-frequency table stored in the symbol-frequency table storage means, wherein the separation processing means obtains, for each test segment, a plurality of separation data or a separation data matrix in which a plurality of the separation data are bound by performing a matrix calculation of multiplying the separation matrix with a plurality of the test data generated by the test data-generating means or a test data matrix in which a plurality of the test data are bound, and wherein the decision means calculates a value indicating a similarity measure of each of column vectors constructed with the values of the feature decision elements of multiple rows assigned according to internal-matrix positions of the feature elements of multiple columns included in the basis matrix among elements constituting a plurality of the separation data or the separation data matrix for the arbitrary one test segment obtained by the separation processing means to column vectors constructed with values of feature decision elements of true data-corresponding portions of a separation data matrix that is obtained together with the separation matrix in the training step, decides at which side of a predetermined threshold exists a value indicating the similarity measure or decides a magnitude of the value thereof, obtains a value indicating the similarity measure of which the absolute value of a difference from the threshold is the largest or of which degree of feature pattern closeness is highest among the values of the similarity measure which are decided to represent the feature pattern or a degree of the feature pattern closeness, and recognizes that the feature pattern putative sequence corresponding to the test data assigned with the obtained value indicating the similarity measure is one of multiple types of the known feature patterns or a new feature pattern that is similar to the known feature patterns.

In such a case where the putative sequences in the test sequence are selected while shifting by one discrete symbol and changing the length at each position, and a process of selecting one sequence that is recognized as a feature pattern from a plurality of the putative sequences. (however, any one feature pattern may not be recognized, which means that two or more putative sequences are not recognized as the feature pattern) is performed, under the condition that the test segment are set to a suitable length, it is possible to recognize the feature pattern with a high accuracy.

As a method that can be implemented by using the aforementioned feature pattern recognition system according to the present invention, there are feature pattern recognition methods as follows.

According to another aspect of the present invention, there is provided a feature pattern recognition method of deciding whether or not one of multiple types of known feature patterns that are found in advance and similar to each other or a new feature pattern that is similar to the known feature pattern is included in a sequence constructed with a finite number of discrete symbols, a segment thereof, or a test segment extracted from the sequence or the segment, comprising: preparing the multiple types of the known feature patterns and generating or preparing multiple types of non-feature patterns different from the known feature patterns obtaining a symbol frequency for each of multiple types of the discrete symbols at each of the sequence positions in the feature patterns by using the multiple types of known feature patterns, generating a symbol-frequency table by corresponding the symbol frequencies to the sequence positions and the types of the discrete symbols in the feature patterns, and storing the symbol-frequency table in symbol-frequency table storage means; converting to numerals the multiple types of known feature patterns and the multiple types of non-feature patterns that are different from the known feature patterns according to the sequence positions and the types of the discrete symbols by using the symbol-frequency table, binding the numerals to generate a training data matrix and performing an independent component analysis or a principal component analysis by using the training data matrix, thereby generating a separation matrix, as a matrix for performing inverse transformation of a basis matrix including feature elements representing the feature patterns and storing the separation matrix in separation matrix storage means; test data-generating means, generating test data by converting to numerals the to-be-decided sequence, the segment thereof, or the test segment extracted from the sequence or the segment according to the sequence positions and the types of the discrete symbols by using the symbol-frequency table stored in the symbol-frequency table storage means; separation processing means, obtaining separation data or a separation data matrix in which a plurality of the separation data are bound by performing a matrix calculation of multiplying the separation matrix stored in the separation matrix storage means with the test data or a test data matrix in which a plurality of the test data are bound; and decision means, deciding whether or not one of the multiple types of the known feature patterns or the new feature pattern similar to the known feature patterns is included in the to-be-decided sequence, the segment thereof, or the test segment extracted from the sequence or the segment or deciding a degree of existence thereof by using the values of feature decision elements assigned according to internal-matrix positions of the feature elements included in the basis matrix among elements constituting the separation data or the separation data matrix obtained by the separation processing means.

According to the feature pattern recognition method of the present invention, the same operations and effects are as those of the aforementioned feature pattern recognition system of the present invention, so that the objects of the present invention can be achieved.

In the aforementioned feature pattern recognition method, preferably, the feature patterns are hierarchical feature patterns that includes a plurality of partial patterns located at different regions, and region positions of the partial patterns in the feature patterns and a whole length of the feature patterns include multiple types of region positions and multiple types of lengths according to a difference of the types of the feature patterns, wherein the symbol-frequency table storage means is whole-pattern symbol-frequency table storage means for storing a whole-pattern symbol-frequency table generated by equalizing whole pattern lengths of the multiple types of the known feature patterns to a constant length by inserting gaps or removing discrete symbols of regions other than the partial patterns, obtaining the symbol frequency for each type of the discrete symbols including the gaps at each of the sequence positions in the feature patterns by using the multiple types of the known feature patterns of which whole pattern lengths are equalized, and corresponding the symbol frequencies to the sequence positions in the feature patterns and the types of the discrete symbols including the gaps, wherein the separation matrix storage means is whole-pattern separation matrix storage means for storing a whole-pattern separation matrix obtained by performing the independent component analysis or the principal component analysis by using a whole-pattern training data matrix generated from the multiple types of the known feature patterns of which whole pattern lengths are equalized and the multiple types of non-feature patterns of which lengths are equalized to the lengths of the multiple types of the known feature patterns, wherein the feature pattern recognition method further comprises: storing a partial-pattern symbol-frequency table obtained for each partial pattern in each region in partial-pattern symbol-frequency table storage means; storing a partial-pattern separation matrix obtained for each partial pattern in each region in partial-pattern separation matrix storage means; and storing elements of at least true data-corresponding portions of a partial-pattern separation data matrix that is obtained together with the partial-pattern separation matrix in a training step for each partial pattern in each region in partial-pattern separation data matrix storage means, wherein the partial-pattern symbol-frequency table storage means stores a partial-pattern symbol-frequency table generated by obtaining, for each partial pattern in each region included in the known feature patterns, the symbol frequencies for each of the types of the discrete symbols at each sequence position in the partial patterns by using the multiple types of the known partial patterns and corresponding the symbol frequencies to the sequence positions in the partial patterns and the types of the discrete symbols, wherein the partial-pattern separation matrix storage means stores, for each partial pattern in each region included in the known feature patterns, a partial-pattern separation matrix as a matrix for performing inverse transformation of a partial-pattern basis matrix including feature elements representing the partial patterns generated by converting to numerals the multiple types of known partial patterns and multiple types of non-partial patterns that are different from the known partial patterns according to the sequence positions and the types of the discrete symbols by using the partial-pattern symbol-frequency table, binding the numerals to generate a partial-pattern training data matrix, and performing an independent component analysis or a principal component analysis by using the partial-pattern training data matrix, wherein the partial-pattern separation data matrix storage means stores elements of at least true data-corresponding portions of a partial-pattern separation data matrix obtained as a result of multiplication of the partial-pattern separation matrix with the partial-pattern training data matrix when the partial-pattern separation matrix is obtained by performing the independent component analysis or the principal component analysis, and wherein, when the test data is generated by the test data-generating means, the feature pattern recognition method further comprises: partial pattern putative data-generating means, generating a plurality of partial pattern putative data by selecting, for each partial pattern in each region, a plurality of partial pattern putative sequences of which the lengths are the same as that of the partial pattern and of which positions are shifted from each other among the to-be-decided sequence, the segment thereof, or the test segment extracted from the sequence or the segment, and converting to numerals a plurality of the partial pattern putative sequences according to the sequence positions and the types of the discrete symbols by using the partial-pattern symbol-frequency table stored in the partial-pattern symbol-frequency table storage means; partial pattern putative data-associated separation data-generating means, generating a plurality of partial pattern putative data-associated separation data or a partial pattern putative data-associated separation data matrix in which a plurality of the partial pattern putative data-associated separation data are bound by performing a matrix calculation of multiplying the partial-pattern separation matrix stored in the partial-pattern separation matrix storage means with each of the partial pattern putative data generated by the partial pattern putative data-generating means or a partial pattern putative data matrix in which a plurality of the partial pattern putative data are bound; partial pattern-corresponding sequences selection means, obtaining partial pattern putative data-associated separation data that are closest to column vectors of true data-corresponding portions of the partial-pattern separation data matrix among a plurality of the partial pattern putative data-associated separation data generated by the partial pattern putative data-associated separation data-generating means and selecting the partial pattern putative sequences corresponding to the obtained partial pattern putative data-associated separation data as partial pattern-corresponding sequences included in feature pattern putative sequences that are candidates of the feature pattern; feature pattern putative sequence selection means, selecting the feature pattern putative sequence based on the partial pattern-corresponding sequences of the regions selected by the partial pattern-corresponding sequences selection means; alignment processing means, performing an alignment process for equalizing lengths of the feature pattern putative sequences selected by the feature pattern putative sequence selection means to a constant length by inserting gaps or removing the discrete symbols of regions other than the partial patterns while each of the partial pattern-corresponding sequences of each region selected by the partial pattern-corresponding sequences selection means is maintained to be in a one-body state; and feature pattern putative sequence numerical conversion means, generating the test data by converting to numerals the feature pattern putative sequences of which lengths are equalized by the alignment processing means according to the sequence positions and the types of the discrete symbols including the gaps by using the whole-pattern symbol-frequency table stored in the whole-pattern symbol-frequency table storage means.

In addition, as described above, in a construction capable of recognizing the hierarchical feature pattern, preferably, when the multiple types of the non-feature patterns of which whole pattern lengths are equalized to constitute the whole-pattern training data matrix used to obtain the whole-pattern separation matrix stored in the whole-pattern separation matrix storage means are generated, the feature pattern recognition method further comprises: generating a plurality of partial pattern putative data by selecting, for each partial pattern in each region, a plurality of partial pattern putative sequences of which the lengths are the same as that of the partial pattern and of which positions are shifted from each other among non-feature patterns-generating sequences prepared to generate the non-feature patterns, and converting to numerals a plurality of the partial pattern putative sequences according to the sequence positions and the types of the discrete symbols by using the partial-pattern symbol-frequency table; generating a plurality of partial pattern putative data-associated separation data or a partial pattern putative data-associated separation data matrix in which a plurality of the partial pattern putative data-associated separation data are bound by performing a matrix calculation of multiplying the partial-pattern separation matrix with each of the partial pattern putative data or a partial pattern putative data matrix in which a plurality of the partial pattern putative data are bound; obtaining partial pattern putative data-associated separation data that are closest to column vectors of true data-corresponding portions of the partial-pattern separation data matrix among the generated plurality of the partial pattern putative data-associated separation data and selecting the partial pattern putative sequences corresponding to the obtained partial pattern putative data-associated separation data as partial pattern-corresponding sequences included in the non-feature patterns; selecting the non-feature patterns based on the selected partial pattern-corresponding sequences of the regions; and performing an alignment process for equalizing lengths of the selected non-feature patterns to a constant length by inserting gaps or removing the discrete symbols of regions other than the partial patterns while each of the partial pattern-corresponding sequences of each region is maintained to be in a one-body state.

In this case, preferably, the multiple types of the non-feature patterns are generated by obtaining the partial pattern putative data-associated separation data in which a similarity measure of the partial pattern putative data-associated separation data to a set of the column vectors of true data-corresponding portions of the partial-pattern separation data matrix is maximized, when obtaining the partial pattern putative data-associated separation data that are closest to column vectors of true data-corresponding portions of the partial-pattern separation data matrix among a plurality of the partial pattern putative data-associated separation data. The similarity measure may include a summation of inner products of the partial pattern putative data-associated separation data to the column vectors of the true data-corresponding portions of the partial-pattern separation data matrix, and like that.

In addition, as described above, in a construction capable of recognizing the hierarchical feature pattern, preferably, when the multiple types of the non-feature patterns are generated, the feature pattern recognition method may comprise obtaining the partial pattern putative data-associated separation data in which a similarity measure of the partial pattern putative data-associated separation data to a set of the column vectors of true data-corresponding portions of the partial-pattern separation data matrix is maximized, when obtaining the partial pattern putative data-associated separation data that are closest to column vectors of true data-corresponding portions of the partial-pattern separation data matrix among a plurality of the partial pattern putative data-associated separation data. The similarity measure may include a summation of inner products of the partial pattern putative data-associated separation data to the column vectors of the true data-corresponding portions of the partial-pattern separation data matrix, and like that.

In addition, in the aforementioned feature pattern recognition method, the decision means may decide at which side of a predetermined threshold exist the values of the feature decision element of the separation data or the separation data matrix obtained by the separation processing means or decides the magnitudes of the values thereof, thereby deciding whether or not one of the multiple types of the known feature patterns or the new feature pattern similar to the known feature patterns is included in the to-be-decided sequence, the segment thereof, or the test segment extracted from the sequence or the segment or deciding a degree of existence thereof.

In addition, in the aforementioned feature pattern recognition method, when multiple columns of the feature elements appear in the basis matrix, wherein multiple rows of elements constituting the separation data or the separation data matrix obtained by the separation processing means are used as the feature decision elements, and wherein the decision means decides whether or not one of the multiple types of the known feature patterns or the new feature pattern similar to the known feature patterns is included in the to-be-decided sequence, the segment thereof, or the test segment extracted from the sequence or the segment or decides a degree of existence thereof by using values of the feature decision elements of the multiple rows of the separation data or the separation data matrix obtained by the separation processing means.

In addition, as described above, when performing a decision process using the values of multiple rows feature decision elements, the decision means calculates a value indicating a similarity measure of a column vector constructed with the values of the feature decision elements of the multiple rows of the separation data or the separation data matrix obtained by the separation processing means to column vectors constructed with values of feature decision elements of true data corresponding portions of a separation data matrix that is obtained together with the separation matrix in the training step and decides at which side of a predetermined threshold exists the calculated value indicating the similarity measure or decides a magnitude of the value thereof, thereby deciding whether or not one of the multiple types of the known feature patterns or the new feature pattern similar to the known feature patterns is included in the to-be-decided sequence, the segment thereof, or the test segment extracted from the sequence or the segment or deciding a degree of existence thereof.

In addition, as described above, when calculating the value indicating the similarity measure, preferably, the decision means calculates, as the value indicating the similarity measure, a value indicating a similarity measure of a column vector constructed with the values of the feature decision elements of the multiple rows of the separation data or the separation data matrix obtained by the separation processing means to a set of column vectors constructed with values of feature decision elements of true data corresponding portions of a separation data matrix that is obtained together with the separation matrix in the training step. More specifically, the decision means calculates, as the value indicating the similarity measure, a value of an inner product of a column vector constructed with the values of the feature decision elements of the multiple rows of the separation data or the separation data matrix obtained by the separation processing means to a centroid vector from the column vectors constructed with the values of feature decision elements of true data corresponding portions of a separation data matrix that is obtained together with the separation matrix in the training step or an equivalent value thereof.

In addition, as described above, when recognizing the hierarchical feature patterns, preferably, the test data-generating means generates a plurality of test data for an arbitrary one test segment by selecting the feature pattern putative sequences while shifting by one discrete symbol among the to-be-decided sequence, the segment thereof, or the test segment extracted from the sequence or the segment, performing an alignment process for equalizing lengths of the selected feature pattern putative sequences to a constant length by inserting gaps or removing discrete symbols of regions other than the partial patterns, and converting to numerals the feature pattern putative sequences of which lengths are equalized according to the sequence positions and the types of the discrete symbols including the gaps by using the whole-pattern symbol-frequency table stored in the whole-pattern symbol-frequency table storage means, wherein the separation processing means obtains, for each test segment, a plurality of separation data or a separation data matrix in which a plurality of the separation data are bound by performing a matrix calculation of multiplying the whole-pattern separation matrix with a plurality of the test data generated by the test data-generating means or a test data matrix in which a plurality of the test data are bound, and wherein the decision means decides at which side of a predetermined threshold exists a value of each of the feature decision elements assigned according to internal-matrix positions of the feature elements included in the basis matrix among elements constituting a plurality of the separation data or the separation data matrix for the arbitrary one test segment obtained by the separation processing means, obtains a value of the feature decision element of which the absolute value of a difference from the threshold is largest or of which degree of the feature pattern closeness is highest among the values of feature decision elements which are decided to represent the feature pattern or a degree of the feature pattern closeness, and recognizes that the feature pattern putative sequence corresponding to the test data assigned with the obtained value of the feature decision element is one of multiple types of the known feature patterns or a new feature pattern that similar to the known feature patterns.

In addition, as described above, when recognizing the hierarchical feature patterns, the test data-generating means generates a plurality of test data for an arbitrary one test segment by selecting the feature pattern putative sequences while shifting by one discrete symbol among the to-be-decided sequence, the segment thereof, or the test segment extracted from the sequence or the segment, performing an alignment process for equalizing lengths of the selected feature pattern putative sequences to a constant length by inserting gaps or removing discrete symbols of regions other than the partial patterns, and converting to numerals the feature pattern putative sequences of which lengths are equalized according to the sequence positions and the types of the discrete symbols including the gaps by using the whole-pattern symbol-frequency table stored in the whole-pattern symbol-frequency table storage means, wherein the separation processing means obtains, for each test segment, a plurality of separation data or a separation data matrix in which a plurality of the separation data are bound by performing a matrix calculation of multiplying the whole-pattern separation matrix with a plurality of the test data generated by the test data-generating means or a test data matrix in which a plurality of the test data are bound, and wherein the decision means calculates a value indicating a similarity measure of each of the column vectors constructed with the values of the feature decision elements of multiple rows assigned according to internal-matrix positions of the feature elements of multiple columns included in the basis matrix among elements constituting a plurality of the separation data or the separation data matrix for the arbitrary one test segment obtained by the separation processing means to column vectors constructed with values of feature decision elements of true data corresponding portions of a separation data matrix that is obtained together with the whole-pattern separation matrix in the training step, decides at which side of a predetermined threshold exists a value indicating the similarity measure or decides a magnitude of the value thereof, obtains a value indicating the similarity measure of which the absolute value of a difference from the threshold is largest or of which degree of the feature pattern closeness is highest among the values of the similarity measure which are decided to represent the feature pattern or a degree of the feature pattern closeness, and recognizes that the feature pattern putative sequence corresponding to the test data assigned with the obtained value indicating the similarity measure is one of multiple types of the known feature patterns or a new feature pattern that is similar to the known feature patterns.

In addition, as described above, when recognizing the hierarchical feature patterns, preferably, the feature pattern recognition method may further comprise, when the partial patterns of each region included in the hierarchical feature patterns have a correlation with specific-site neighborhood sequences including a specific site of the sequence, correlation training result storage means for storing information including a correlation training result obtained by training in advance as information used to decide the correlation of the partial pattern of each region with the specific-site neighborhood sequences, wherein the partial pattern putative data-generating means of the test data-generating means selects a plurality of the partial pattern putative sequences for each of the partial patterns of each region based on a relative positional relation to the specific site or a relative positional relation to partial pattern putative sequences of other regions defined according to the relative positional relation to the specific site, and wherein the feature pattern putative sequence selection means of the test data-generating means decides the existence of correlation or a degree of the correlation between the partial pattern-corresponding sequences of each region selected by the partial pattern-corresponding sequences selection means of the test data-generating means and the specific-site neighborhood sequences by using the information including the correlation training result stored in the correlation training result storage means and, if there is no correlation or if the degree of the correlation is low, does not perform a decision process for the feature pattern putative sequence based on the partial pattern-corresponding sequences of each region and the specific site in the specific-site neighborhood sequences.

As described above, when performing the correlation-decision process for deciding a correlation between the partial pattern-corresponding sequences of each region and the specific-site neighborhood sequence, preferably, the correlation training result storage means comprises: correlation-decision symbol-frequency table storage means for storing a correlation-decision symbol-frequency table generated by binding the known partial patterns of at least one region among a plurality of regions included in the known feature patterns with known specific-site neighborhood sequences to generate multiple types of correlation-binding sequences, obtaining a symbol frequency for each type of the discrete symbols at each sequence position in the correlation-binding sequences by using multiple types of correlation-binding sequences, and corresponding the symbol frequencies to the sequence positions and the types of the discrete symbols in the correlation-binding sequences; and correlation-decision separation matrix storage means for storing a correlation-decision separation matrix used for a correlation-decision process for deciding the correlation between the partial patterns of each region and the specific-site neighborhood sequences, wherein the correlation-decision separation matrix storage means stores a correlation-decision separation matrix, as a matrix for performing inverse transformation of a correlation-decision basis matrix including feature elements representing correlation-binding sequences, generated by converting to numerals correlation-binding sequences generated by binding the known partial patterns of at least one region among a plurality of the regions with the known specific-site neighborhood sequences and non-correlation-binding sequences generated by binding the known partial patterns of at least one region among a plurality of the regions with non-specific-site neighborhood sequences different from the known specific-site neighborhood sequences according to the sequence positions and the types of the discrete symbols by using the correlation-decision symbol-frequency table, binding the numerals to generate a correlation-decision training data matrix, and performing an independent component analysis or a principal component analysis by using the correlation-decision training data matrix, and wherein the feature pattern putative sequence selection means of the test data generating means, when deciding the existence of a correlation or a degree of the correlation between the partial pattern-corresponding sequences of each region and the specific-site neighborhood sequences, generates correlation-decision sequences by binding the partial pattern-corresponding sequences of at least one region among a plurality of the regions with the specific-site neighborhood sequences, converts to numerals the correlation-decision sequences according to the sequence positions and the types of the discrete symbols by using the correlation-decision symbol-frequency table stored in the correlation-decision symbol-frequency table storage means to generate correlation-decision data, performs a correlation-decision separation process for obtaining correlation-decision separation data or a correlation-decision separation data matrix in which a plurality of the correlation-decision separation data are bound by performing a matrix calculation of multiplying the correlation-decision separation matrix stored in the correlation-decision separation matrix storage means with the correlation-decision data or a correlation-decision data matrix in which a plurality of the correlation-decision data are bound, and decides the existence of the correlation or a degree of the correlation by using a value of the correlation-decision element assigned according to internal-matrix positions of the feature elements included in the correlation-decision basis matrix among the correlation-decision separation data obtained in the correlation-decision separation process or the elements constituting the correlation-decision separation data matrix.

As described above, when performing a correlation-decision process by using a correlation-decision separation matrix obtained in a pre-training using an independent component analysis (ICA) or a principal component analysis (PCA), the feature pattern putative sequence selection means of the test data-generating means may decide the existence of a correlation or a degree of the correlation by deciding at which side of a predetermined correlation-decision threshold exists a value of the correlation-decision element. In addition, the correlation-decision process may be performed by using the values of multiple rows of the correlation-decision elements.

The aforementioned feature pattern recognition methods may be suitably applied to a case where the sequence is a DNA sequence, the discrete symbols are symbols A, T, G, and C, representing nucleotides constituting the DNA sequence, or substitute symbols thereof, and the feature pattern is a promoter in the DNA sequence.

Among the aforementioned feature pattern recognition methods, a method having a construction capable of recognizing the hierarchical feature pattern may be suitably applied to a case where the sequence is a DNA sequence, the discrete symbols are symbols A, T, G, and C, representing nucleotides constituting the DNA sequence, or substitute symbols thereof, the feature pattern is a promoter in the DNA sequence, and the partial patterns are a −35 box and a −10 box included in the promoter.

Among the aforementioned feature pattern recognition methods, a method having a construction of performing a correlation-decision process for deciding a correlation between the partial pattern-corresponding sequences of each region and the specific-site neighborhood sequence may be suitably applied to a case where the sequence is a DNA sequence, the discrete symbols are symbols A, T, G, and C, representing nucleotides constituting the DNA sequence, or substitute symbols thereof, the feature pattern is a promoter in the DNA sequence, the partial patterns are a −35 box and a −10 box included in the promoter, the specific site is a transcription start site of the DNA sequence, and the specific-site neighborhood sequences is a transcription-start-site neighborhood sequence.

The aforementioned feature pattern recognition method may be suitably applied to a case where the sequence is an amino acid sequence constituting a protein, the discrete symbols are symbols representing the amino acids constituting the amino acid sequence, and the feature pattern is a motif of the amino acid sequence.

In addition, in a case where there are multiple types of lengths in the feature patterns, when non-hierarchical feature patterns are recognized or when hierarchical feature patterns are recognized by using the same scheme as the non-hierarchical case, the following methods may be used.

In the aforementioned feature pattern recognition method, preferably, the lengths of the feature pattern include multiple types of lengths according to the difference of the types of the feature patterns, wherein the symbol-frequency table storage means stores a symbol-frequency table generated by equalizing the lengths of the multiple types of the known feature patterns to a constant length by inserting gaps, by obtaining the symbol frequency for each type of the discrete symbols including the gaps at each of the sequence positions in the feature patterns by using the multiple types of the known feature patterns of which lengths are equalized, and corresponding the symbol frequencies to the sequence positions in the feature patterns and the types of the discrete symbols including the gaps, wherein the separation matrix storage means stores a separation matrix obtained by performing the independent component analysis or the principal component analysis by using a training data matrix generated from the multiple types of the known feature patterns of which the lengths are equalized and the multiple types of non-feature patterns of which the lengths are equalized to the lengths of the multiple types of the known feature patterns, and wherein the test data-generating means generates the test data by selecting putative sequences that become candidates of the feature patterns among the to-be-decided sequence, the segment thereof, or the test segment extracted from the sequence or the segment, performing an alignment process for equalizing lengths of the selected putative sequences to a constant length by inserting gaps, and converting to numerals the putative sequences of which the lengths are equalized according to the sequence positions and the types of the discrete symbols including the gaps by using the symbol-frequency table stored in the symbol-frequency table storage means.

In addition, as described above, in case of performing an alignment process, preferably, the test data-generating means generates a plurality of test data for an arbitrary one test segment by selecting the putative sequences while shifting by one discrete symbol and changing a length at each position among the to-be-decided sequence, the segment thereof, or the test segment extracted from the sequence or the segment, performing an alignment process for equalizing lengths of a plurality of the selected putative sequences to a constant length by inserting gaps, and converting to numerals the putative sequences of which lengths are equalized according to the sequence positions and the types of the discrete symbols including the gaps by using the symbol-frequency table stored in the symbol-frequency table storage means, wherein the separation processing means obtains, for each test segment, a plurality of separation data or a separation data matrix in which a plurality of the separation data are bound by performing a matrix calculation of multiplying the separation matrix with a plurality of the test data generated by the test data-generating means or a test data matrix in which a plurality of the test data are bound, and wherein the decision means decides at which side of a predetermined threshold exists a value of each of the feature decision elements assigned according to the internal-matrix positions of the feature elements included in the basis matrix among elements constituting a plurality of the separation data or the separation data matrix for the arbitrary one test segment obtained by the separation processing means, obtains a value of the feature decision element of which the absolute value of a difference from the threshold is largest or of which degree of the feature pattern closeness is highest among the values of the feature decision elements which are decided to represent the feature pattern or a degree of the feature pattern closeness, and recognizes that the feature pattern putative sequence corresponding to the test data assigned with the obtained value of the feature decision element is one of multiple types of the known feature patterns or a new feature pattern that similar to the known feature patterns.

In addition, as described above, when performing an alignment process, the test data-generating means generates a plurality of test data for an arbitrary one test segment by selecting the putative sequences while shifting by one discrete symbol and changing a length at each position among the to-be-decided sequence, the segment thereof, or the test segment extracted from the sequence or the segment, performing an alignment process for equalizing lengths of a plurality of the selected putative sequences to a constant length by inserting gaps, and converting to numerals the putative sequences of which lengths are equalized according to the sequence positions and the types of the discrete symbols including the gaps by using the symbol-frequency table stored in the symbol-frequency table storage means, wherein the separation processing means obtains, for each test segment, a plurality of separation data or a separation data matrix in which a plurality of the separation data are bound by performing a matrix calculation of multiplying the separation matrix with a plurality of the test data generated by the test data generating means or a test data matrix in which a plurality of the test data are bound, and wherein the decision means calculates a value indicating a similarity measure of each of the column vectors constructed with the values of the feature decision elements of multiple rows assigned according to internal-matrix positions of the feature elements of the multiple columns included in the basis matrix among the elements constituting a plurality of the separation data or the separation data matrix for the arbitrary one test segment obtained by the separation processing means to column vectors constructed with the values of the feature decision elements of the true data-corresponding portions of a separation data matrix that is obtained together with the separation matrix in the training step, decides at which side of a predetermined threshold exists a value indicating the similarity measure or decides a magnitude of the value thereof, obtains a value indicating the similarity measure of which the absolute value of a difference from the threshold is largest or of which degree of the feature pattern closeness is highest among the values of the similarity measure which are decided to represent the feature pattern or a degree of the feature pattern closeness, and recognizes that the feature pattern putative sequence corresponding to the test data assigned with the obtained value indicating the similarity measure is one of multiple types of the known feature patterns or a new feature pattern that similar to the known feature patterns.

According to still another aspect of the present invention, there is provided a program for configuring a computer in a feature pattern recognition system for deciding whether or not one of multiple types of known feature patterns that are found in advance and similar to each other or a new feature pattern that is similar to the known feature pattern is included in a sequence constructed with a finite number of discrete symbols, a segment thereof, or a test segment extracted from the sequence or the segment, comprising: symbol-frequency table storage means for storing a symbol-frequency table generated by obtaining a symbol frequency for each of multiple types of the discrete symbols at each of the sequence positions in the feature patterns by using the multiple types of known feature patterns and by corresponding the symbol frequencies to the sequence positions and the types of the discrete symbols in the feature patterns; separation matrix storage means for storing a separation matrix, as a matrix for performing inverse transformation of a basis matrix including feature elements representing the feature patterns, generated by converting to numerals the multiple types of known feature patterns and the multiple types of non-feature patterns that are different from the known feature patterns according to the sequence positions and the types of the discrete symbols by using the symbol-frequency table, by binding the numerals to generate a training data matrix, and by performing an independent component analysis or a principal component analysis by using the training data matrix; test data-generating means for generating test data by converting to numerals the to-be-decided sequence, the segment thereof, or the test segment extracted from the sequence or the segment according to the sequence positions and the types of the discrete symbols by using the symbol-frequency table stored in the symbol-frequency table storage means; separation processing means for obtaining separation data or a separation data matrix in which a plurality of the separation data are bound by performing a matrix calculation of multiplying the separation matrix stored in the separation matrix storage means with the test data or a test data matrix in which a plurality of the test data are bound; and decision means for deciding whether or not one of the multiple types of the known feature patterns or the new feature pattern similar to the known feature patterns is included in the to-be-decided sequence, the segment thereof, or the test segment extracted from the sequence or the segment or deciding a degree of existence thereof by using values of feature decision elements assigned according to internal-matrix positions of the feature elements included in the basis matrix among elements constituting the separation data or the separation data matrix obtained by the separation processing means.

In addition, the program or a portion thereof may be recorded on a recording medium such as optical magnetic drive (MO), read-only memory using compact disk (CD) (CD-ROM), CD-recordable (CD-R), CD rewritable (CD-RW), read-only memory using digital versatile disk (DVD) (DVD-ROM), random access memory using DVD (DVD-ROM), flexible disk (FD), magnetic tape, hard disk, read-only memory (ROM), electrical erasable/programmable read-only memory (EEPROM), flash memory, random access memory (RAM), or the like. Therefore, in this manner, the program can be preserved and commercially provided. In addition, the program can be transmitted through transmission media such as local area network (LAN), metropolitan area network (MAN), wide area network (WAN), wire or wireless network such as Internet, intranet, and extranet, or a combination thereof. Moreover, the program can be transmitted on a carrier wave. The program may be a portion of other programs. In addition, the program together with separate programs may be recorded on the recording medium.

Effects of the Invention

As described above, according to the present invention, each of the discrete symbols constituting a to-be-decided sequence is converted to numerals by using symbol frequency according to each sequence position or each type of the discrete symbol, and it is decided whether or not feature patterns exist in the sequence by using a separation matrix obtained by performing an independent component analysis (ICA) or a principal component analysis (PCA). Therefore, in comparison with a computer analysis using a conventional neural network method or an expectation-maximization algorithm (EM algorithm), it is possible to improve a feature pattern recognition accuracy for a promoter or the like. In addition, in comparison with a promoter analysis using a biological experiment in a test tube or an X-ray analysis, it is possible to implement a feature pattern analysis having advantages in terms of processing time and cost.

BRIEF DESCRIPTION OF THE DRAWINGS

FIG. 2 is a detailed view illustrating a construction of a training means in the promoter recognition system according to the first embodiment.

FIG. 5 is a view illustrating an example of a sequence including a known promoter extracted from a DNA sequence according to the first embodiment.

FIG. 6 is a first view for explaining a process in the −35 box training according to the first embodiment.

FIG. 7 is a second view for explaining a process in the −35 box training according to the first embodiment.

FIG. 12 is a first view for explaining a process in the −10 box training according to the first embodiment.

FIG. 13 is a second view for explaining a process in the −10 box training according to the first embodiment.

FIG. 31 is a fourth view for explaining a process in the correlation training according to the first embodiment.

FIG. 43 is a view illustrating a promoter symbol-frequency table $T_{prom}$ according to the second embodiment of the present invention.

FIG. 45 is a graph illustrating values of elements of a first column of an inverse matrix $W_{prom}^{-1}$ of a promoter-associated separation matrix $W_{prom}$ obtained in a process of a training step according to the second embodiment.

FIG. 46 is a graph illustrating values of elements of a first row of a promoter-associated separation data matrix $Y_{prom}$ obtained in a process of the training step according to the second embodiment.

BEST MODE FOR CARRYING OUT THE INVENTION

Hereinafter, embodiments of the present invention are described with reference to the accompanying drawings.

First Embodiment

Figure 1:
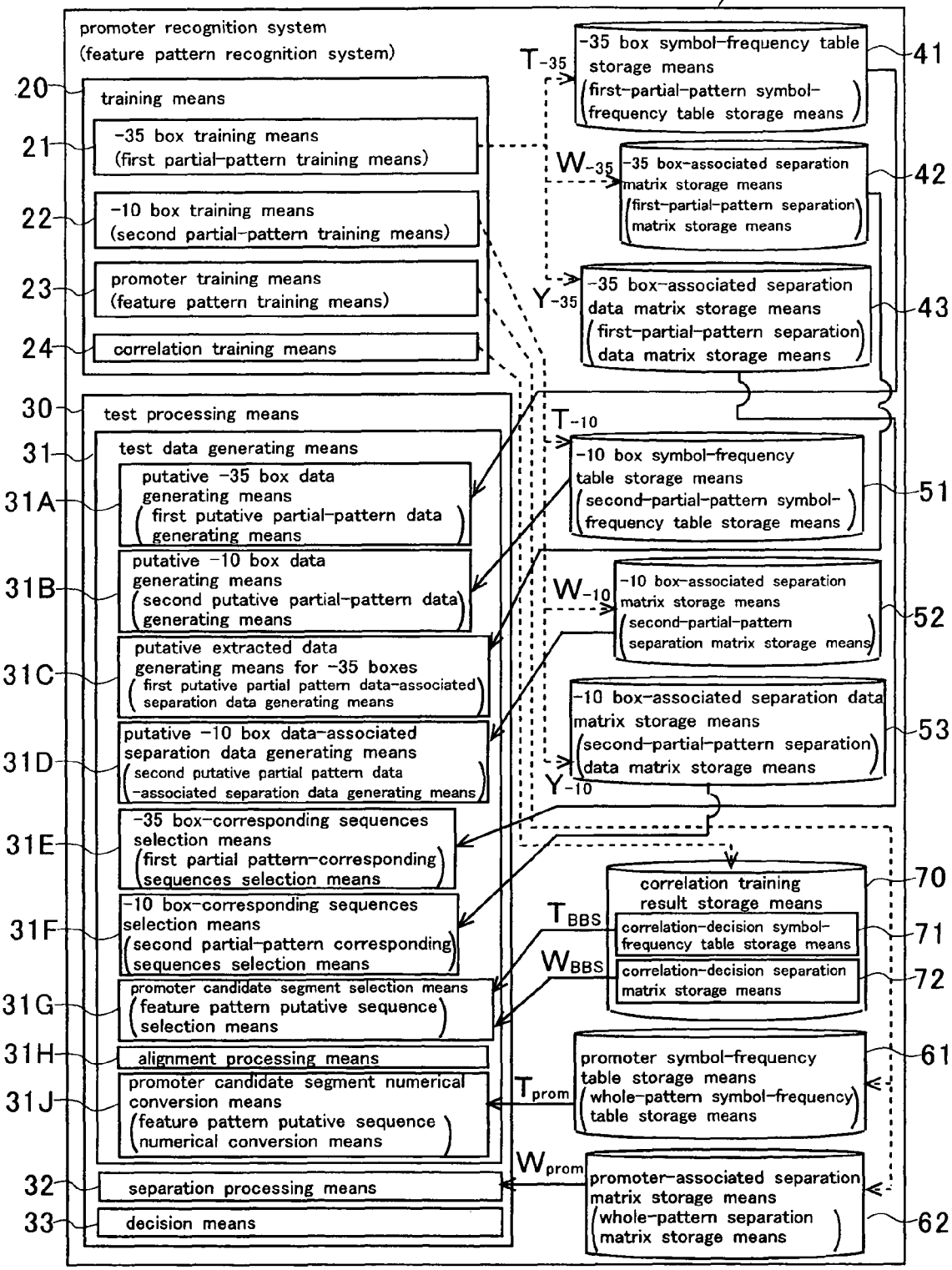
FIG. 1 is a view illustrating a whole construction of a promoter recognition system according to a first embodiment of the present invention.
Figure 3:
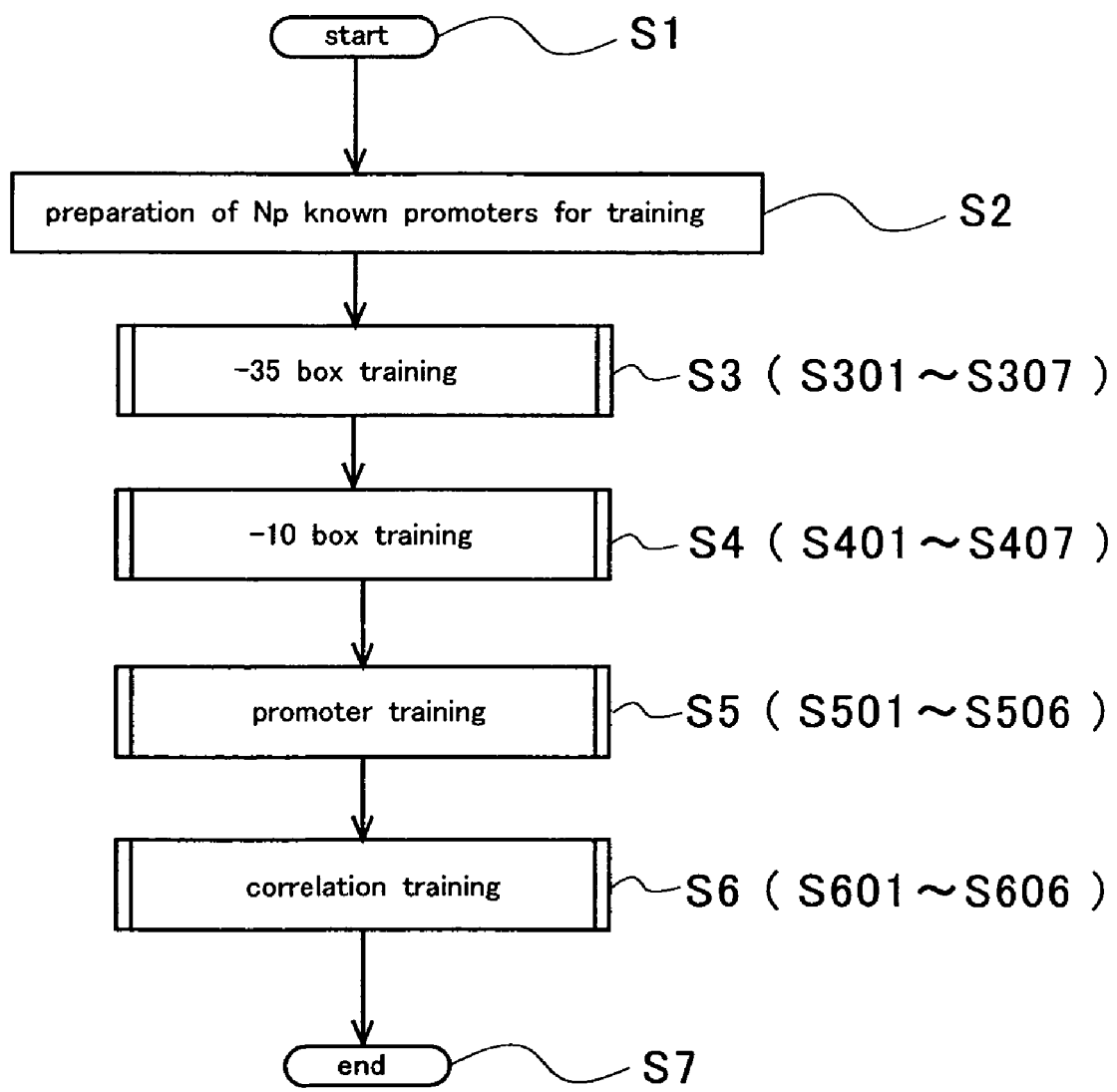
FIG. 3 is a flowchart illustrating a whole flow of a training step according to the first embodiment.
Figure 4:
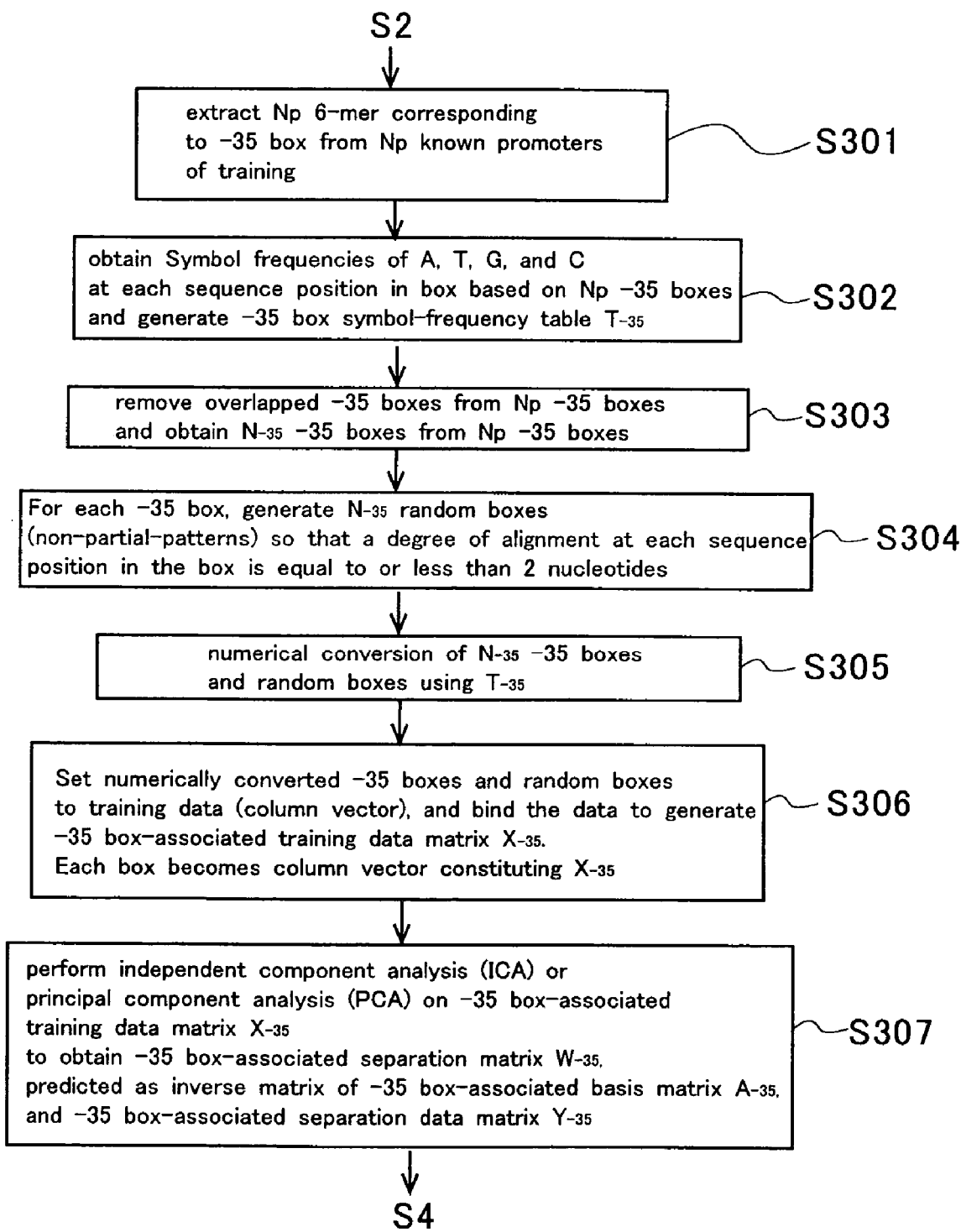
FIG. 4 is a flowchart illustrating a flow of −35 box training according to the first embodiment.
Figure 16:
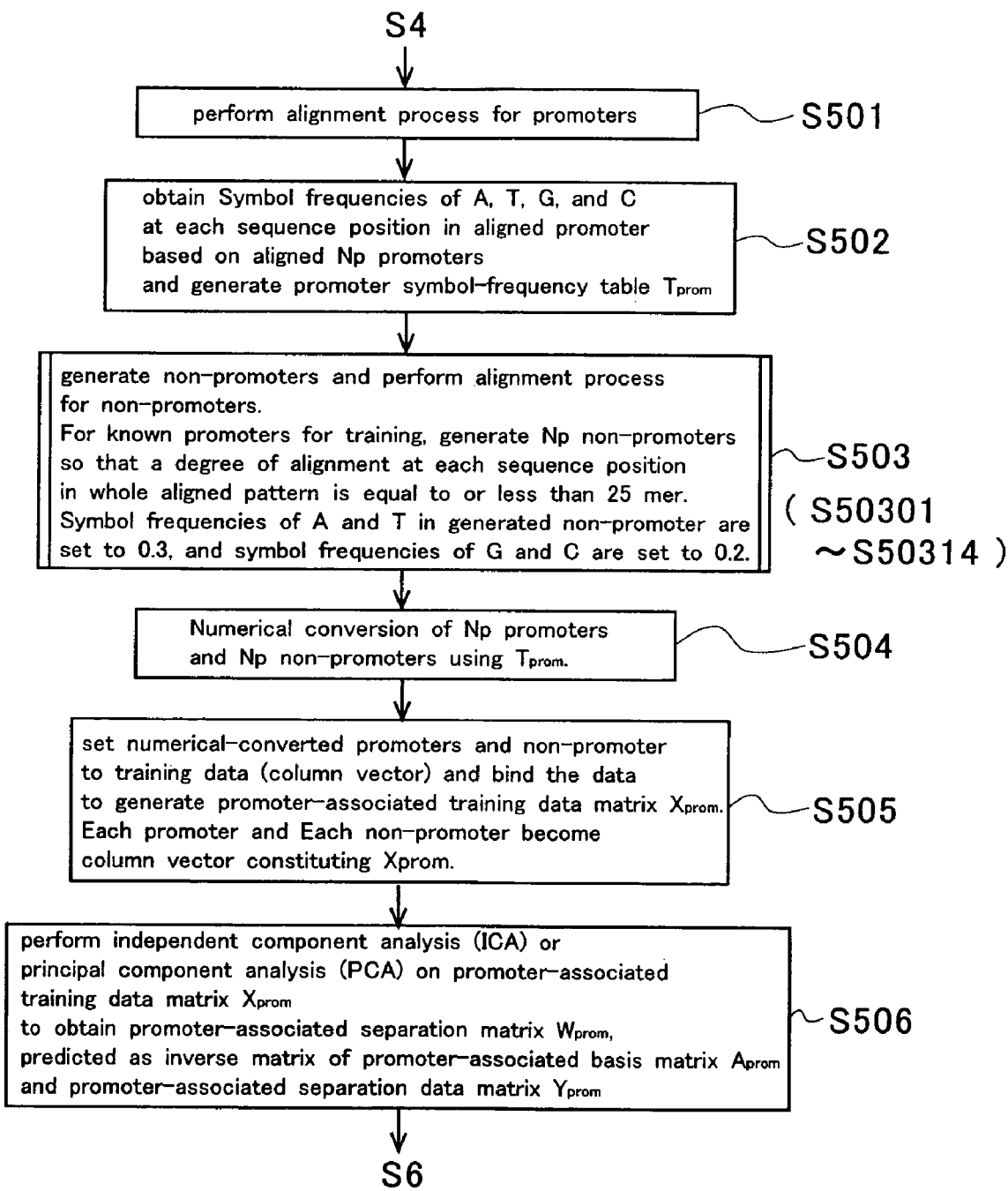
FIG. 16 is a flowchart illustrating a flow of promoter training according to the first embodiment.
Figure 17:
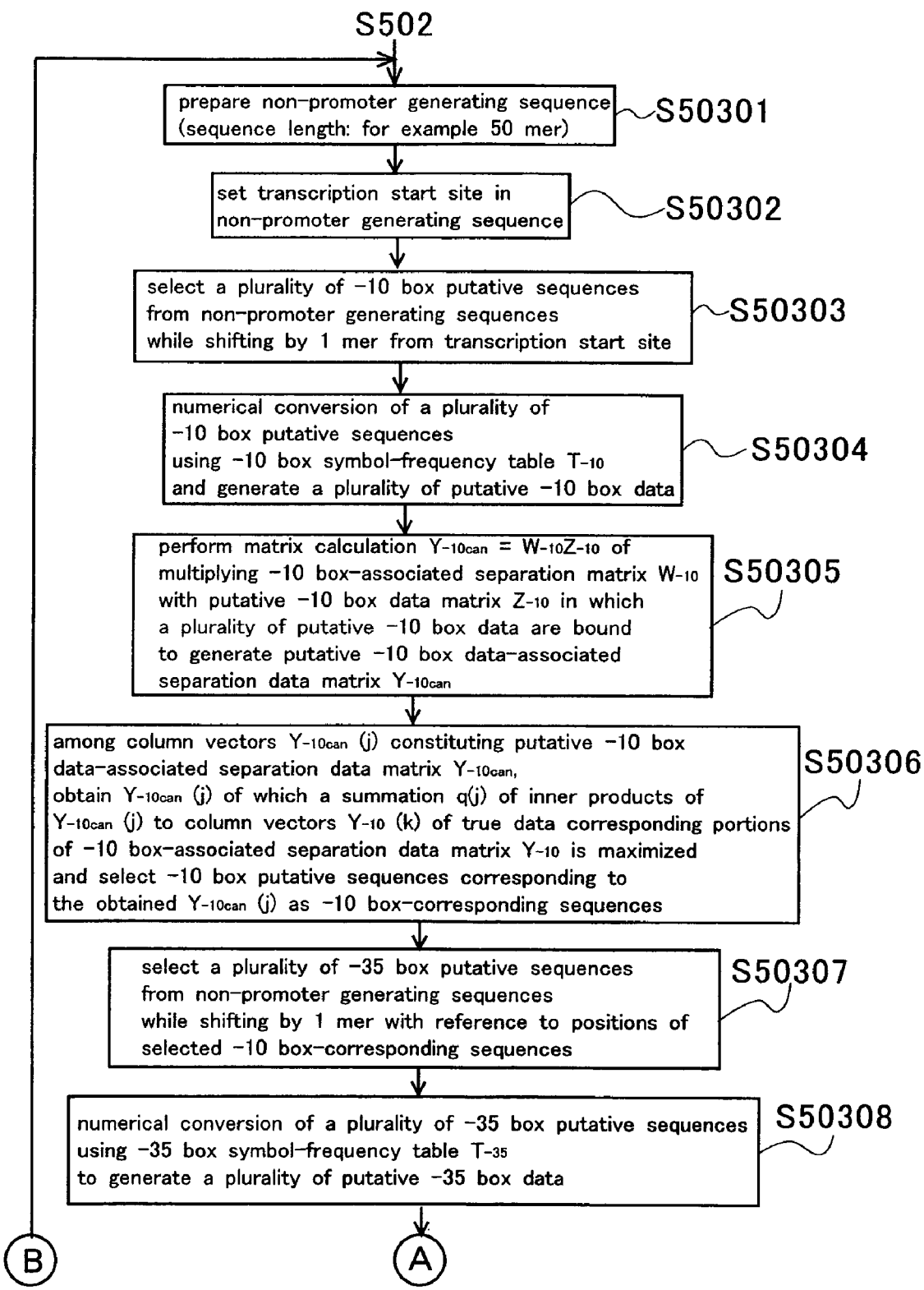
FIG. 17 is a detailed flowchart illustrating a first portion of the flow of the promoter training according to the first embodiment.
Figure 18:
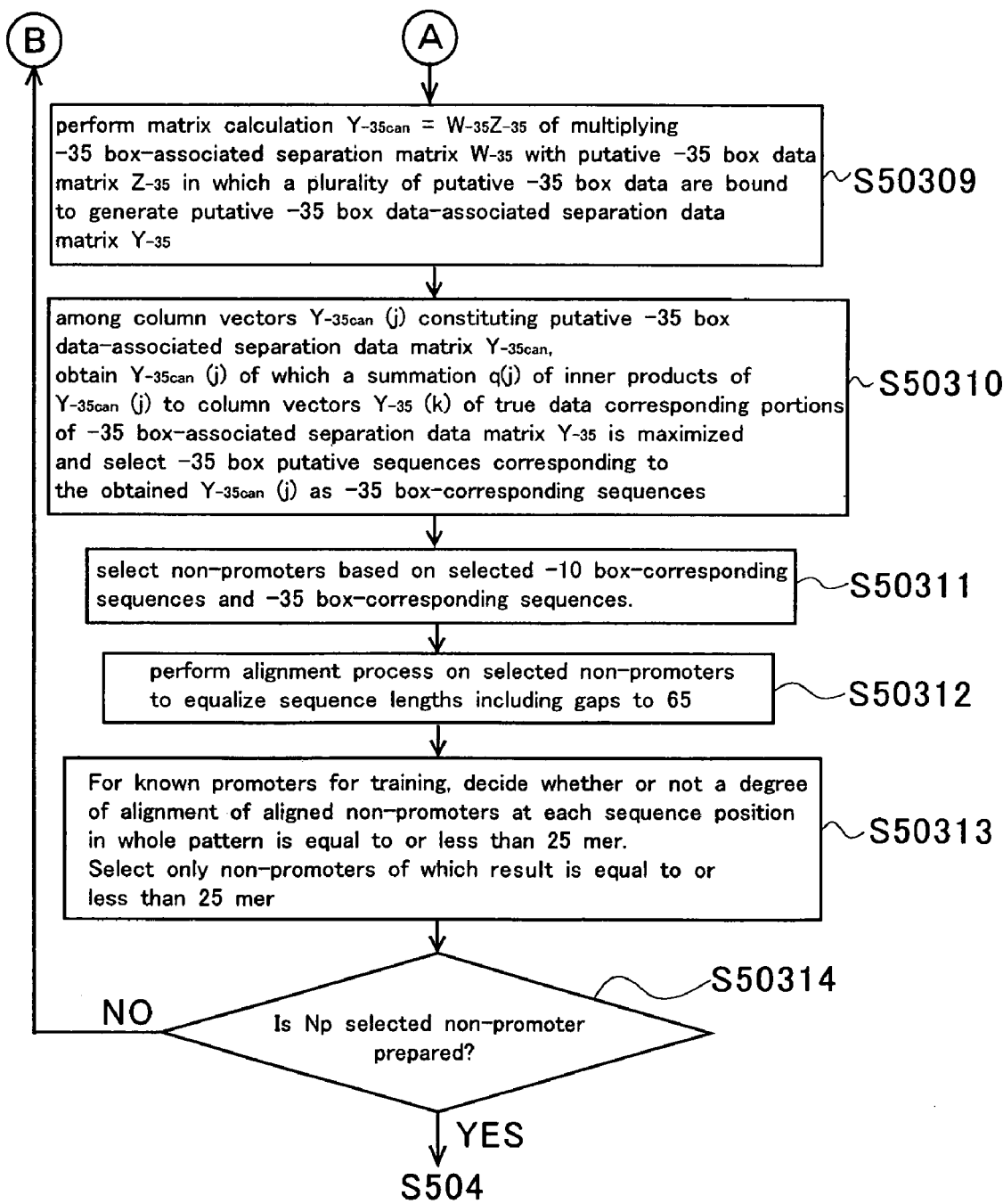
FIG. 18 is a detailed flowchart illustrating a second portion of the flow of the promoter training according to the first embodiment.
Figure 26:
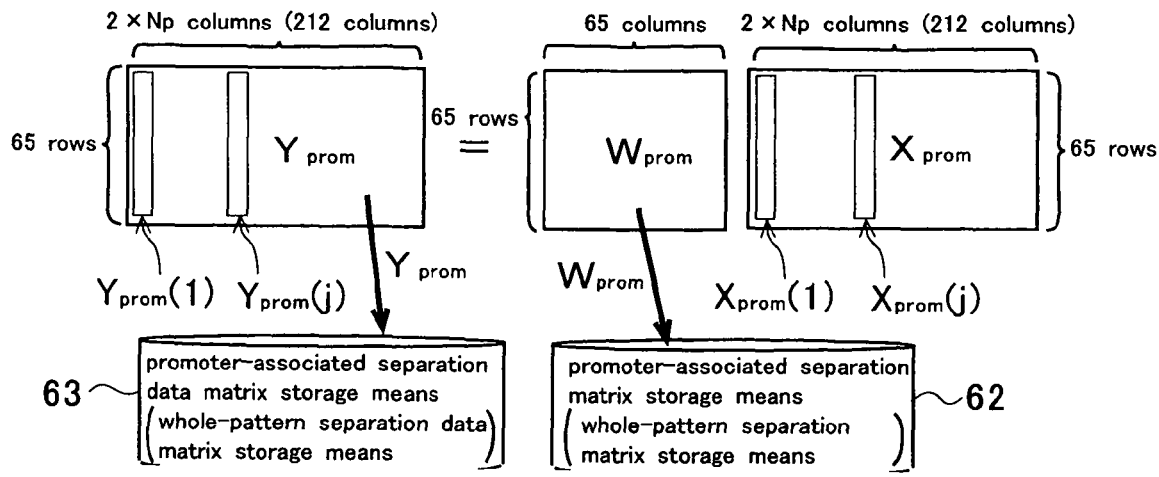
FIG. 26 is an eighth view for explaining a process in the promoter training according to the first embodiment.
Figure 27:
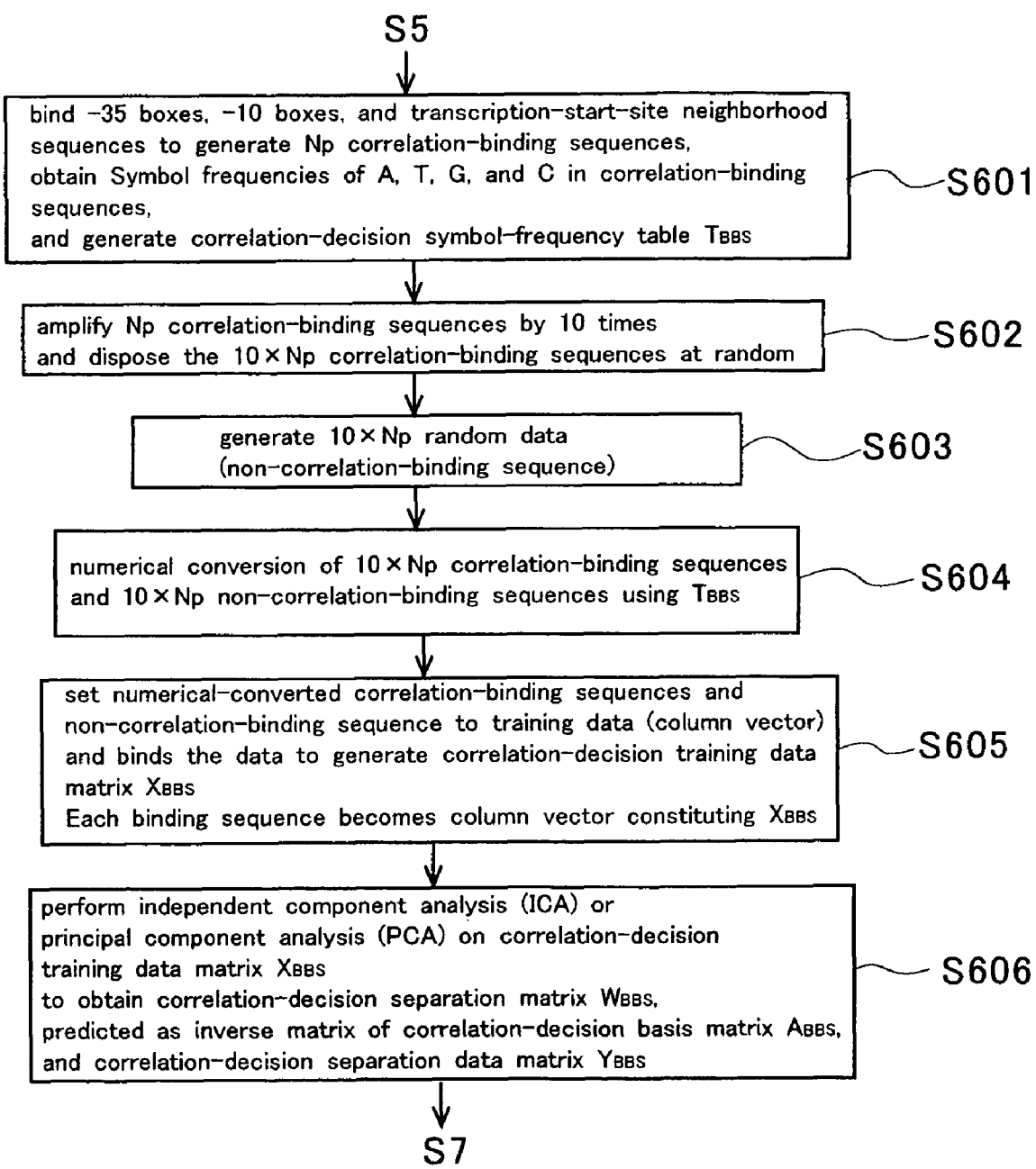
FIG. 27 is a flowchart illustrating a flow of correlation training according to the first embodiment.
Figure 32:
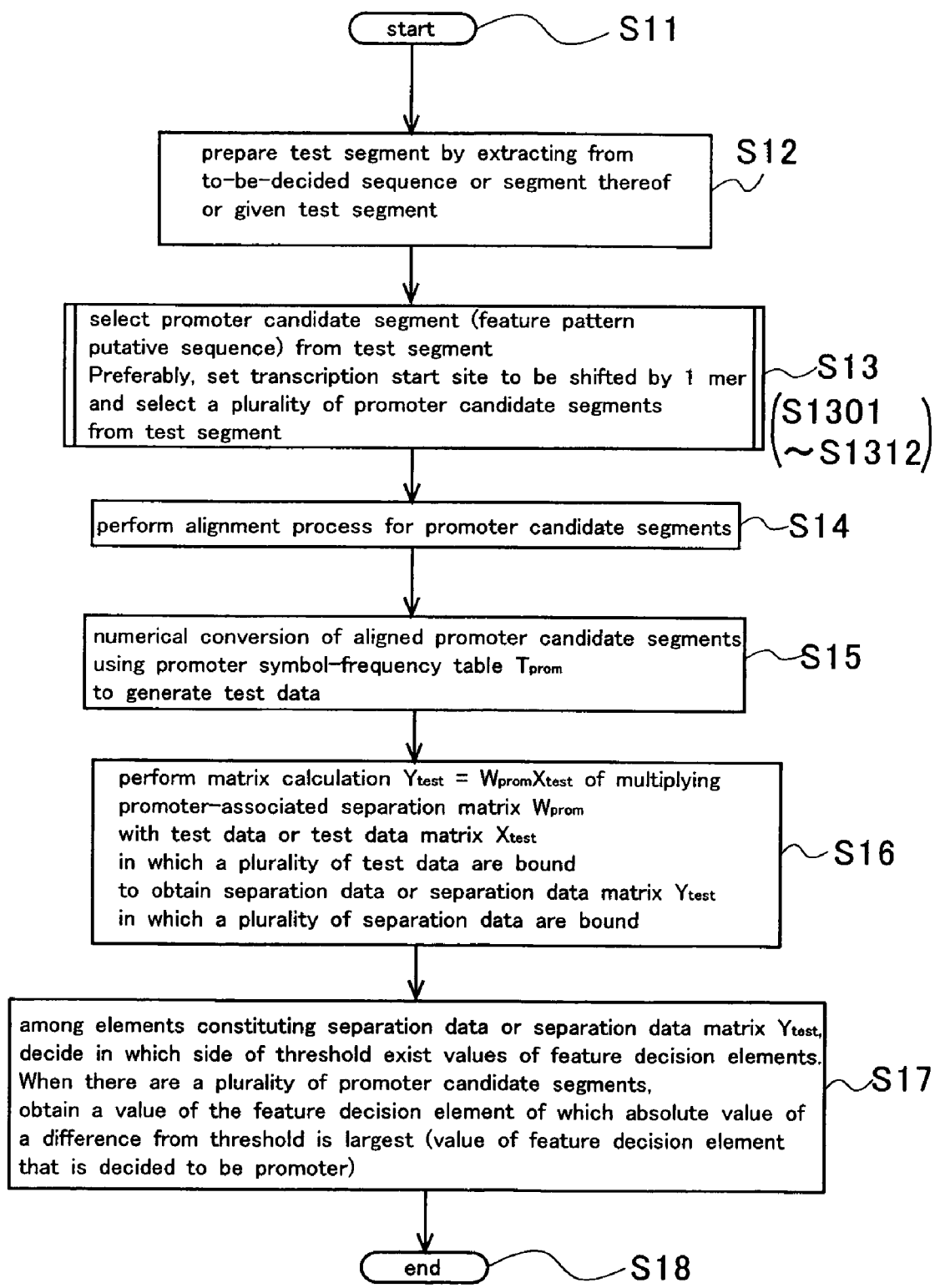
FIG. 32 is a flowchart illustrating a whole flow of a test step according to the first embodiment.
Figure 33:
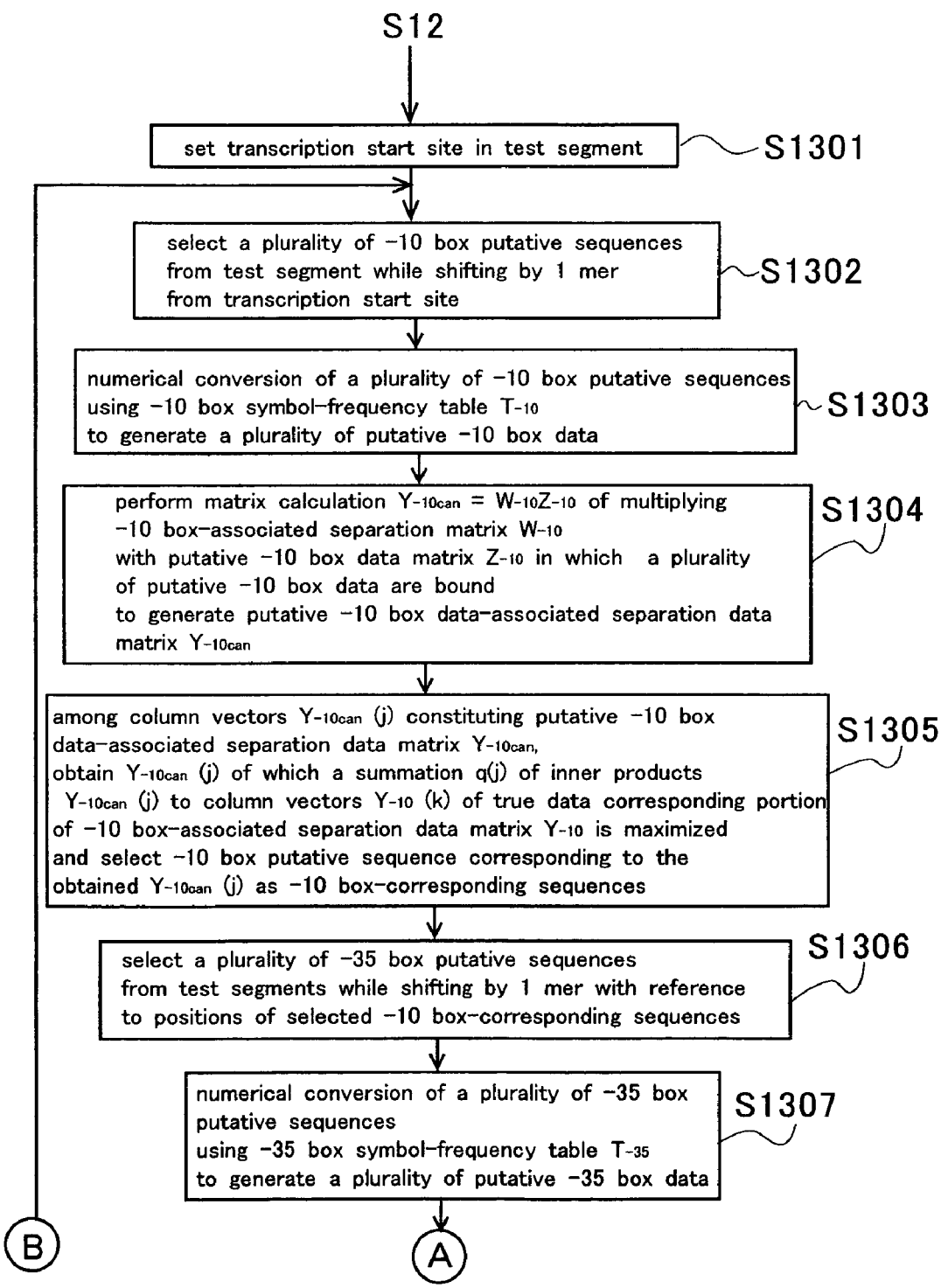
FIG. 33 is a detailed flowchart illustrating a first portion of the flow of test step according to the first embodiment.
Figure 34:
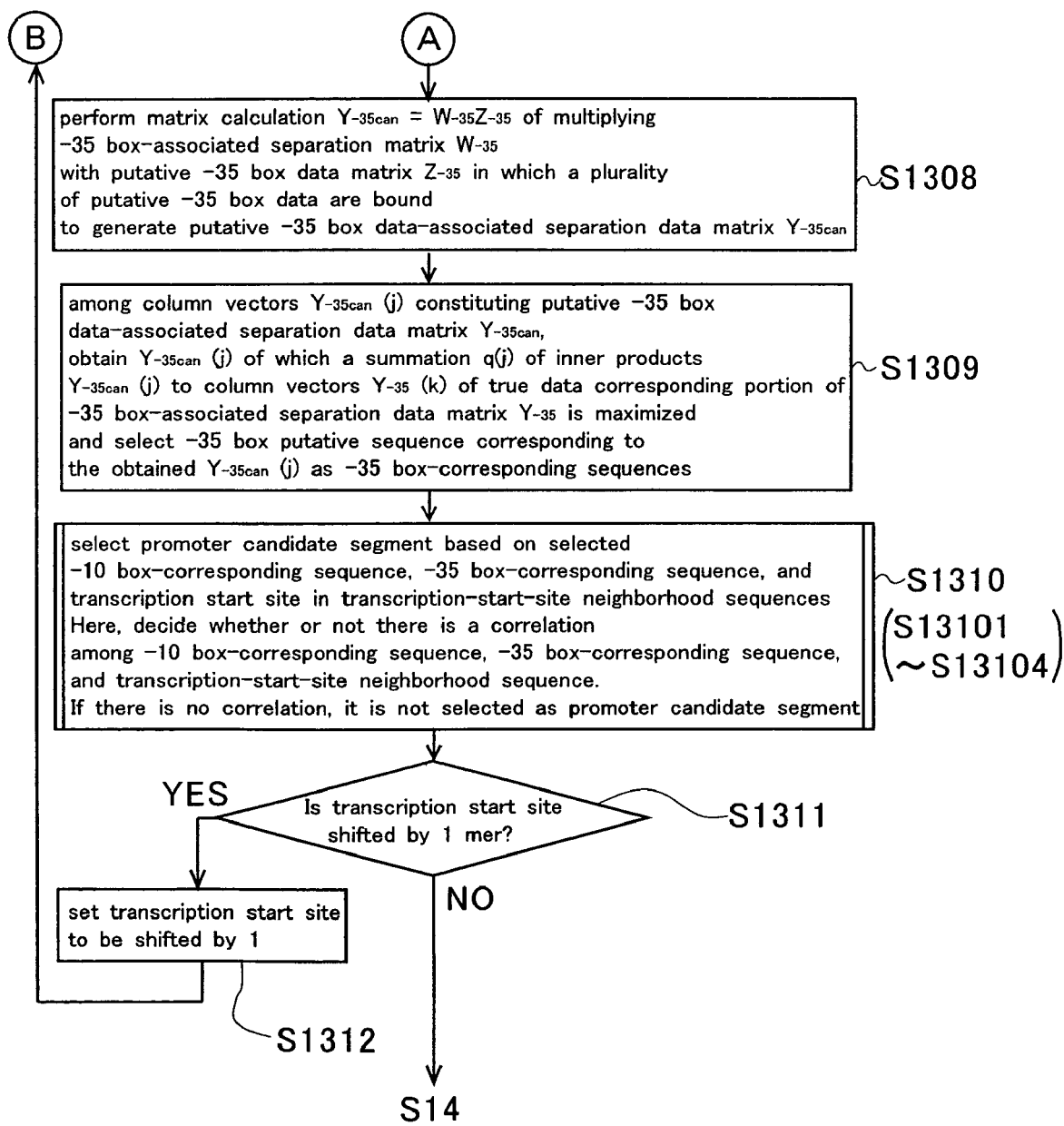
FIG. 34 is a detailed flowchart illustrating a second portion of the flow of test step according to the first embodiment.
Figure 35:
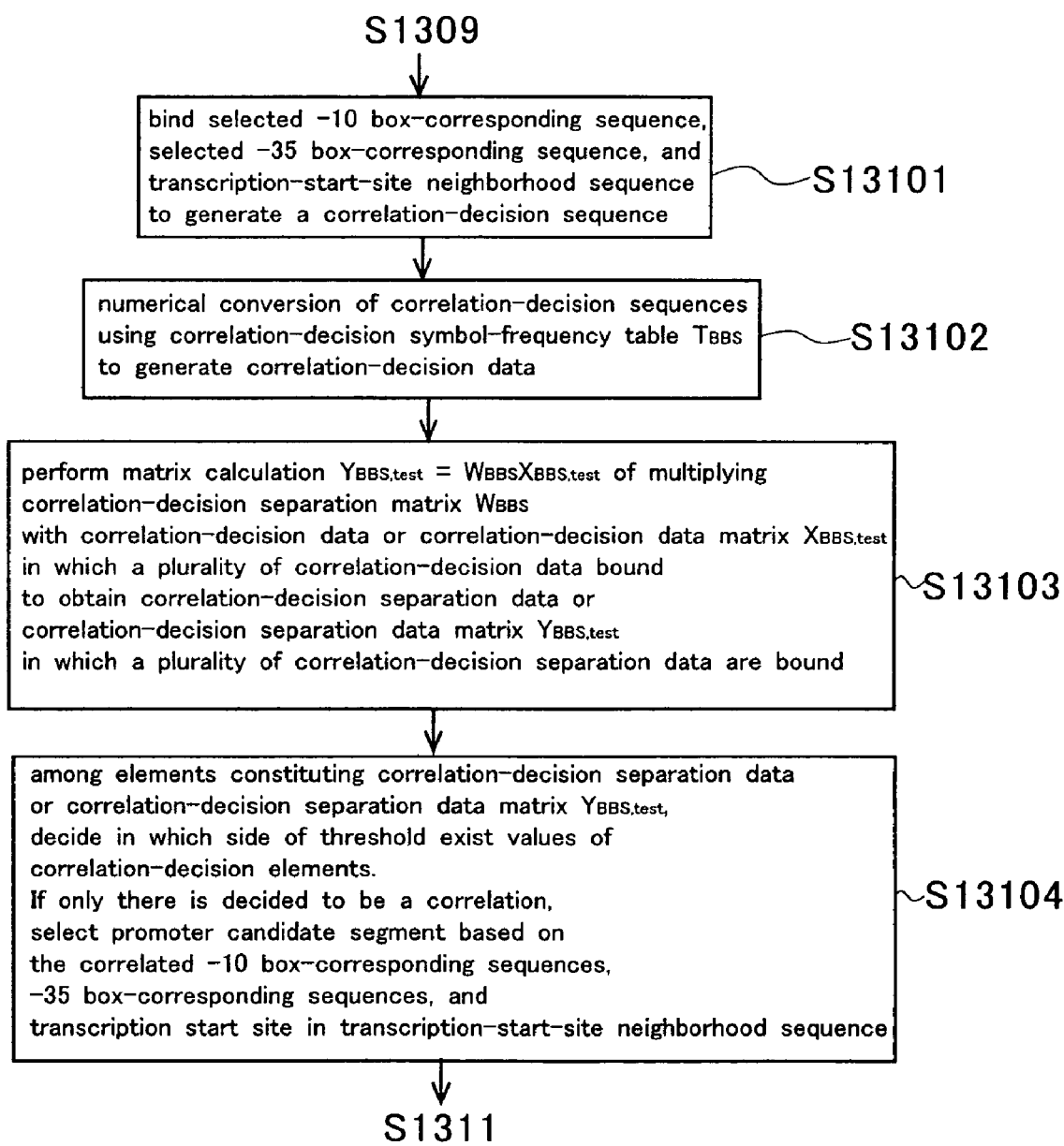
FIG. 35 is a flowchart illustrating a flow of a correlation decision process in the test step according to the first embodiment.
Figure 36:
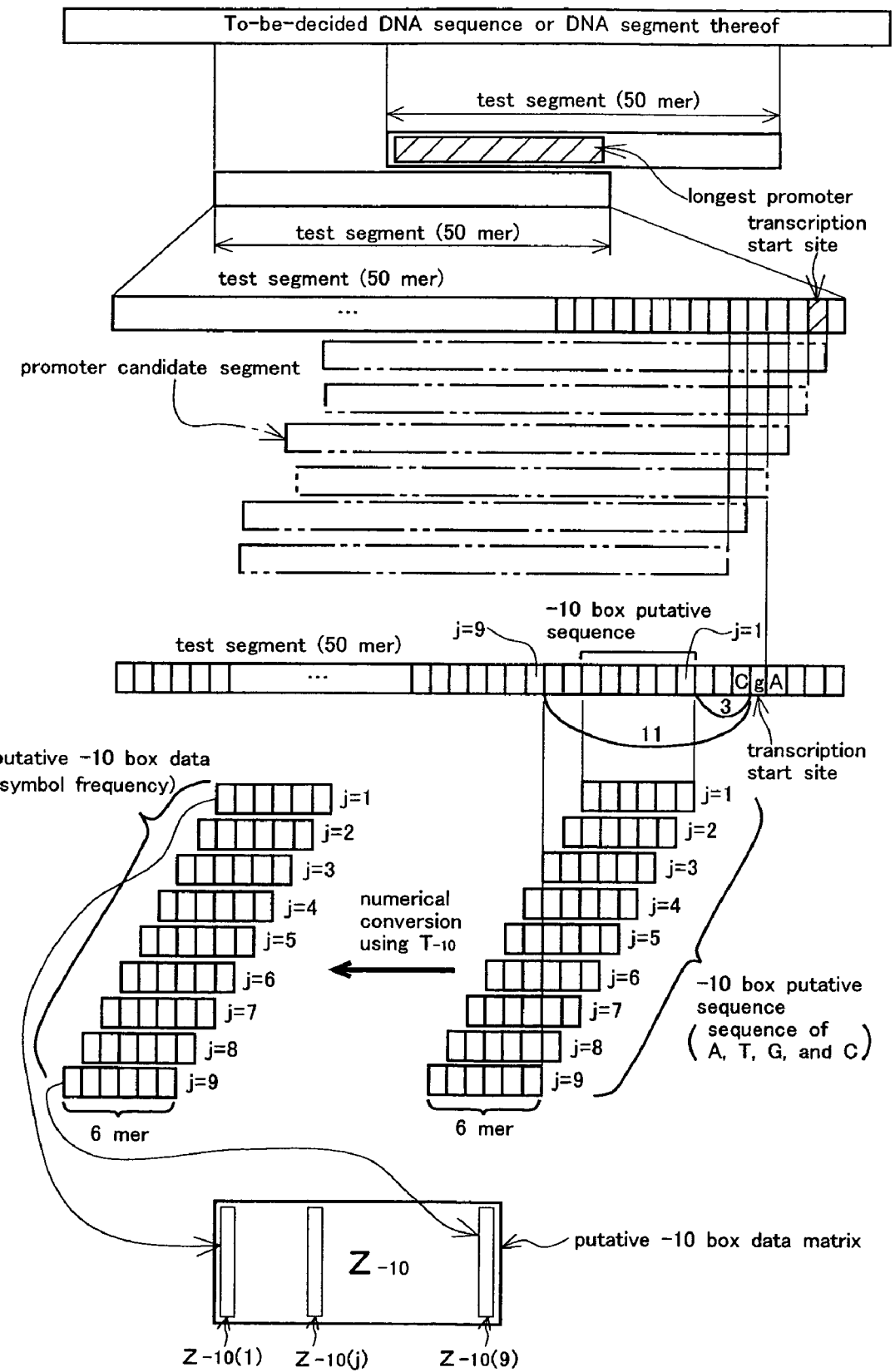
FIG. 36 is a first view for explaining a process in the test step according to the first embodiment.
Figure 37:
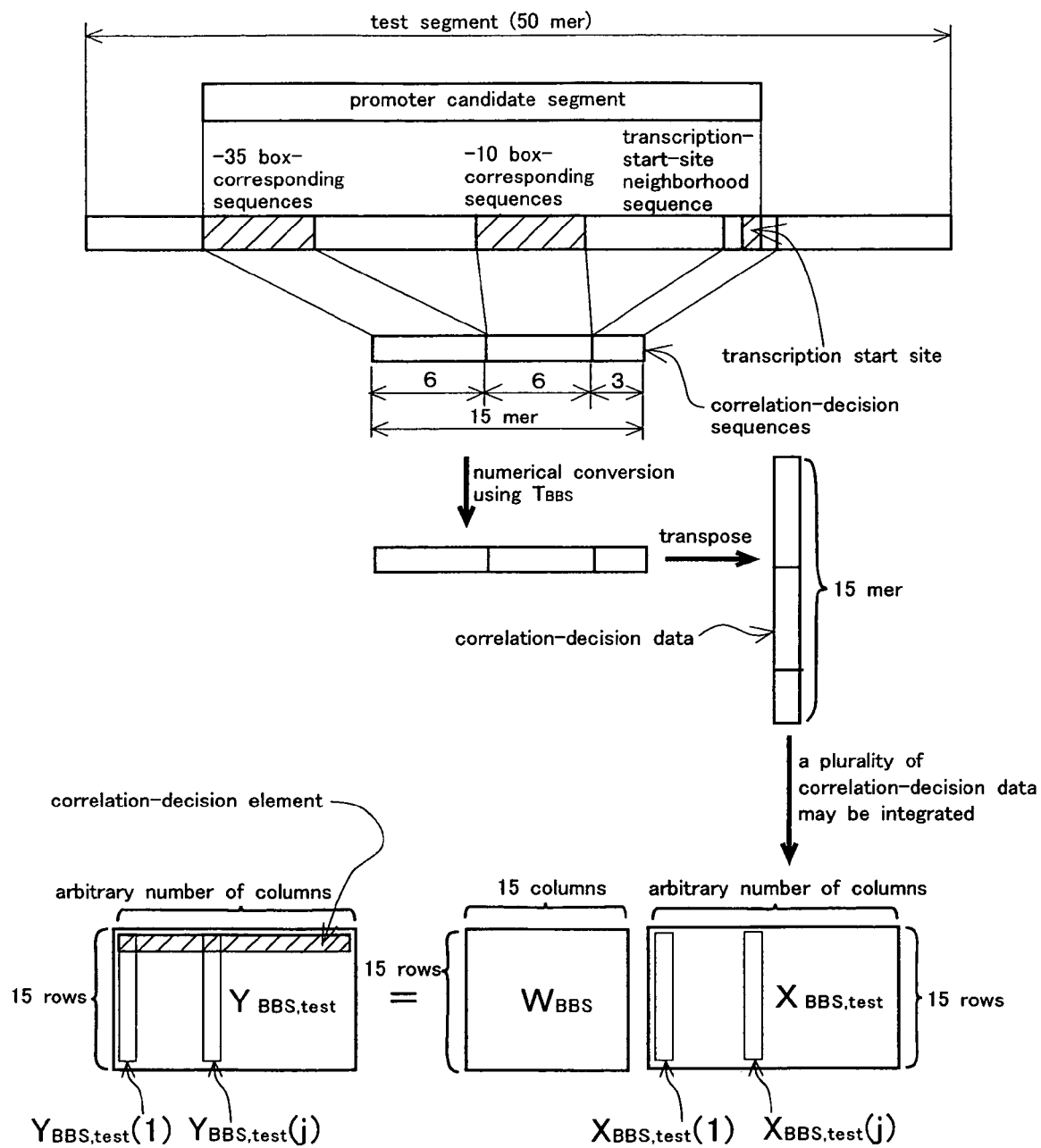
FIG. 37 is a second view for explaining a process in the test step according to the first embodiment.
Figure 38:
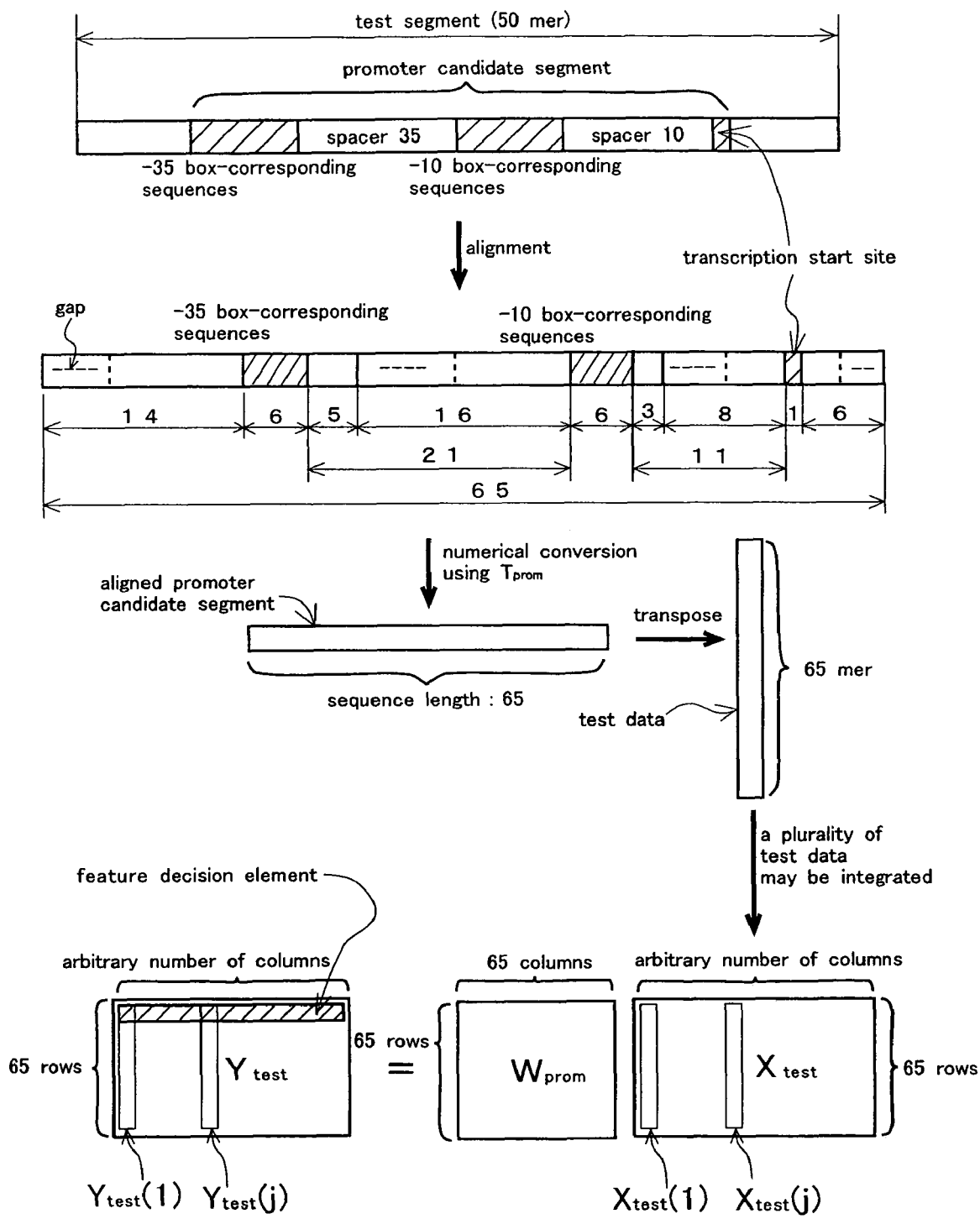
FIG. 38 is a third view for explaining a process of the test step according to the first embodiment.

FIG. 1 is a view illustrating a whole construction of a promoter recognition system 10 as a feature pattern recognition system according to a first embodiment of the present invention. FIG. 2 is a detailed view illustrating a construction of a training means 20 in the promoter recognition system 10. FIG. 3 is a flowchart illustrating a whole flow of a training step. FIG. 4 is a flowchart illustrating a flow of −35 box training. FIG. 5 is a view illustrating an example of a sequence including a known promoter extracted from a DNA sequence. FIGS. 6 to 10 are views for explaining processes in the −35 box training. FIG. 11 is a flowchart illustrating a flow of −10 box training. FIGS. 12 to 15 are views for explaining processes in the −10 box training. FIGS. 16 to 18 are flowcharts illustrating a flow of promoter training. FIGS. 19 to 26 are views for explaining processes in the promoter training. FIG. 27 is a flowchart illustrating a flow of correlation training. FIGS. 28 to 31 are views for explaining processes in the correlation training. FIG. 32 is a flowchart illustrating a whole flow of a test step. FIGS. 33 to 35 are detailed flowcharts illustrating processes in the test step. FIGS. 36 to 38 are views for explaining processes in the test step.

Referring to FIG. 1, the promoter recognition system 10 includes training means 20 for performing various processes in the training step and test processing means 30 for performing various processes in the test step. The promoter recognition system 10 is a system for deciding whether or not a promoter as a feature pattern exists in a DNA sequence (for example, a *Escherichia coli* nucleic base sequence) constructed with 4 nucleotide symbols A, T, G, and C shown in FIG. 5. The promoter (for example, an *Escherichia coli* promoter) exists in the vicinity of a gene coding region. The promoter includes a +1 region constructed with a transcription start site where transcription of nucleic base sequence information from DNA to RNA starts and a nucleotide (−1) shifted by 1 mer at the upstream thereof, a 6-mer length −35 box shifted by about 35 mer at the upstream of the transcription start site, and a 6-mer length −10 box shifted by about 10 mer at the upstream of the transcription start site. A spacer 35 which has a relatively constant length of 15 mer to 21 mer is disposed between the −35 box and the −10 box. A spacer 10 which has a length of 3 mer to 11 mer is disposed between the −10 box and the transcription start site. In the specification, the spacer 10 is defined as not a sequence between the −10 box and the +1 region (−1 and +1) but a sequence between the −10 box and the transcription start site (+1). The transcription start site together with front and rear nucleotides constitutes a specific pattern. Therefore, in the specification, a sequence constructed with three nucleotides, that is, the transcription start site (+1) and the front and rear nucleotides (−1 and +2) is defined as a transcription-start-site neighborhood sequence, that is, a specific-site neighborhood sequence. However, the transcription-start-site neighborhood sequence is not limited to the 3-mer sequence. For example, a 5-mer sequence may be employed. In other words, a region including the transcription start site (+1) can be employed so as to represent a specific pattern.

In addition, the promoter recognition system 10 includes −35 box symbol-frequency table storage means 41 that is first-partial-pattern symbol-frequency table storage means for storing a −35 box symbol-frequency table $T_{-35}$ that is a first-partial-pattern symbol-frequency table, −35 box-associated separation matrix storage means 42 that is first-partial-pattern separation matrix storage means for storing a −35 box-associated separation matrix $W_{-35}$ that is a first-partial-pattern separation matrix, and −35 box-associated separation data matrix storage means 43 that is first-partial-pattern separation data matrix storage means for storing a −35 box-associated separation data matrix $Y_{-35}$ that is a first-partial-pattern separation data matrix.

In addition, the promoter recognition system 10 includes −10 box symbol-frequency table storage means 51 that is second-partial-pattern symbol-frequency table storage means for storing a −10 box symbol-frequency table $T_{-10}$ that is a second-partial-pattern symbol-frequency table, −10 box-associated separation matrix storage means 52 that is second-partial-pattern separation matrix storage means for storing a −10 box-associated separation matrix $W_{-10}$ that is a second-partial-pattern separation matrix, and −10 box-associated separation data matrix storage means 53 that is second-partial-pattern separation data matrix storage means for storing a −10 box-associated separation data matrix $Y_{-10}$ that is a second-partial-pattern separation data matrix. In addition, the promoter recognition system 10 includes promoter symbol-frequency table storage means 61 as whole-pattern symbol-frequency table storage means for storing a promoter symbol-frequency table $T_{prom}$ as a whole-pattern symbol-frequency table, promoter-associated separation matrix storage means 62 as whole-pattern separation matrix storage means for storing a promoter-associated separation matrix $W_{prom}$ as a whole-pattern separation matrix, and promoter-associated separation data matrix storage means 63 as whole-pattern separation data matrix storage means for storing a promoter-associated separation data matrix $Y_{prom}$ as a whole-pattern separation data matrix (see FIG. 26).

In addition, the promoter recognition system 10 includes correlation training result storage means 70 for storing information containing a correlation training result. The correlation training result storage means 70 is provided with correlation-decision symbol-frequency table storage means 71 for storing a correlation-decision symbol-frequency table $T_{BBS}$, correlation-decision separation matrix storage means 72 for storing a correlation-decision separation matrix $W_{BBS}$, and correlation-decision separation data matrix storage means 73 for storing a correlation-decision separation data matrix $Y_{BBS}$ (see FIG. 31).

The training means 20 includes −35 box training means 21 that is first partial pattern training means, −10 box training means 22 that is second partial pattern training means, promoter training means 23 that is feature pattern training means, and correlation training means 24.

FIG. 2, the −35 box training means 21 includes −35 box symbol-frequency table generating means 21A that is first-partial-pattern symbol-frequency table generating means, random box-generating means 21B that is first-non-partial-pattern-generating means, −35 box-associated numerical conversion means 21C that is first-partial-pattern numerical conversion means, −35 box-associated training data matrix-generating means 21D that is first-partial-pattern training data matrix-generating means, and −35 box-associated analyzing means 21E that is first-partial-pattern analyzing means.

The −35 box symbol-frequency table-generating means 21A obtains symbol frequencies of the symbols A, T, G, and C at each sequence position in multiple types of known −35 boxes by using nucleotide information of the −35 boxes and generates a −35 box symbol-frequency table $T_{-35}$ (see FIG. 6) by corresponding the symbol frequencies to the sequence positions and symbols in the −35 boxes (see Step S302 of FIG. 4). The −35 box symbol-frequency table generating means 21A stores the generated $T_{-35}$ in the −35 box symbol-frequency table storage means 41 (see FIG. 1).

The random box-generating means 21B generates random boxes so as to prepare false data (column vectors of $C_{-35}^T$ shown in FIG. 8) among training data (column vectors) of the −35 box-associated training data matrix $X_{-35}$ (see FIG. 8) that is the first-partial-pattern training data matrix (see Step S304 of FIG. 4).

The −35 box-associated numerical conversion means 21C converts to numerals the known −35 boxes and the random boxes generated by the random box generating means 21B according to the sequence positions in the boxes and the types of symbols A, T, G, and C by using the −35 box symbol-frequency table $T_{-35}$ (see FIG. 6) stored in the −35 box symbol-frequency table storage means 41 (see FIG. 1) and generates $B_{-35}$ (see FIG. 7) and $C_{-35}$ (see Step S305 of FIG. 4).

The −35 box-associated training data matrix-generating means 21D transposes the $B_{-35}$ (see FIG. 7) and $C_{-35}$ obtained by the numerical conversion of the −35 box-associated numerical conversion means 21C into $B_{-35}^T$ and $C_{-35}^T$, respectively, and binds the $B_{-35}^T$ and $C_{-35}^T$ to generate a −35 box-associated training data matrix $X_{-35}$ (see FIG. 8) (see Step S306 of FIG. 4). Alternatively, the order of the binding and the numerical conversion may be inverted.

Figure 9:
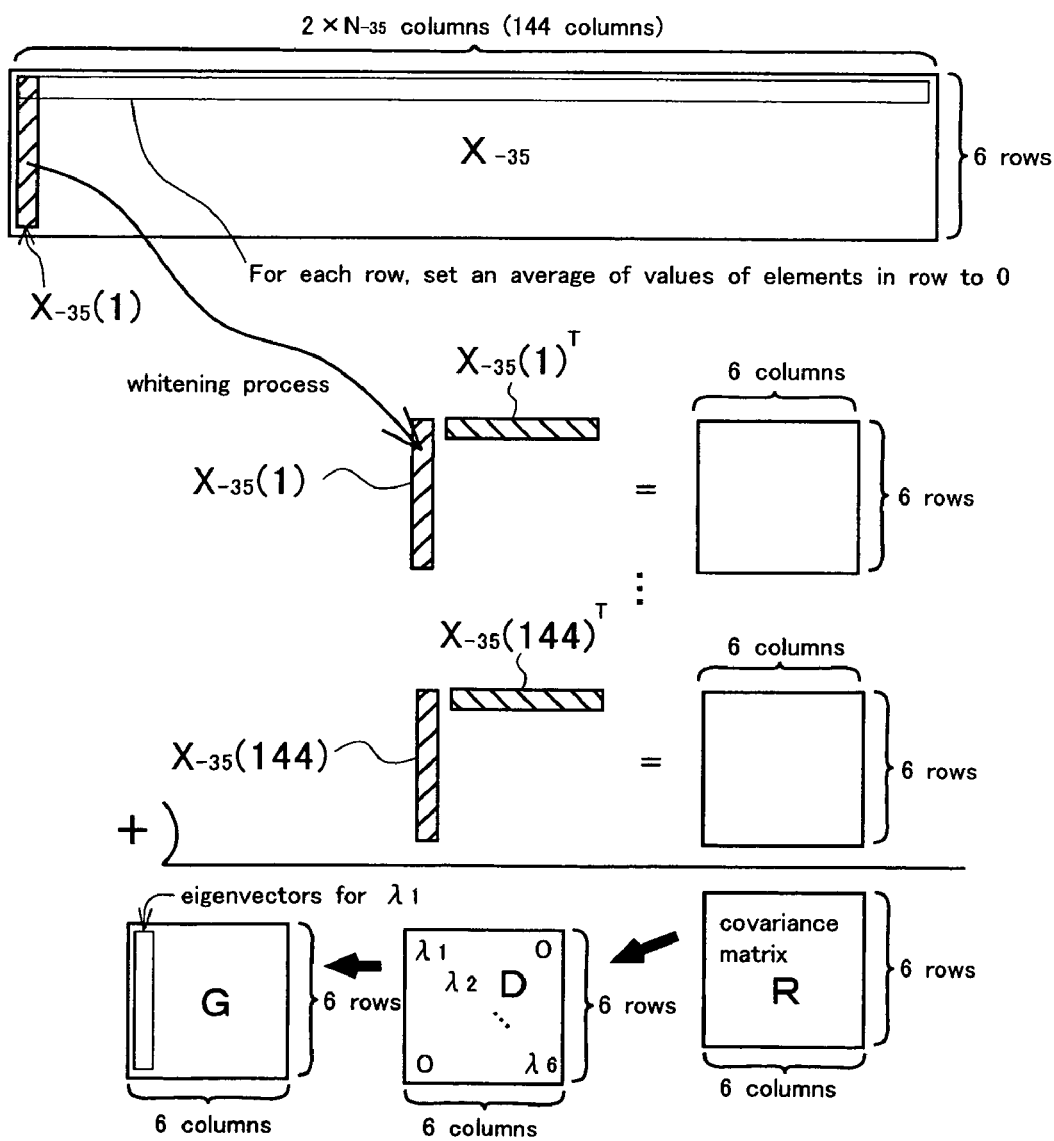
FIG. 9 is a fourth view for explaining a process in the −35 box training according to the first embodiment.
Figure 10:
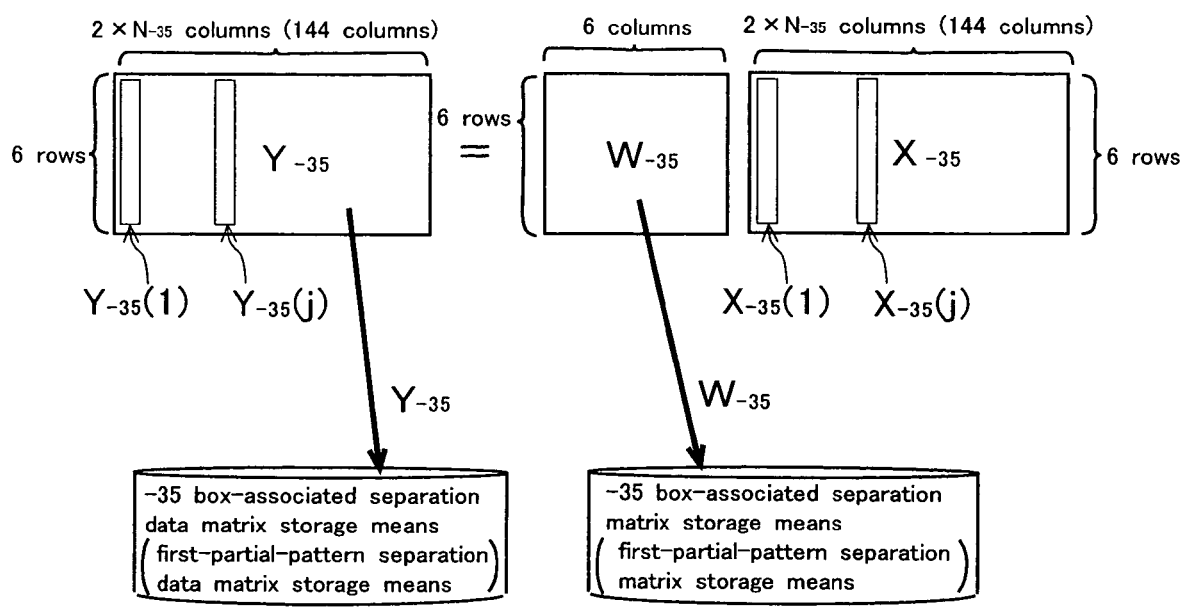
FIG. 10 is a fifth view for explaining a process in the −35 box training according to the first embodiment.
Figure 11:
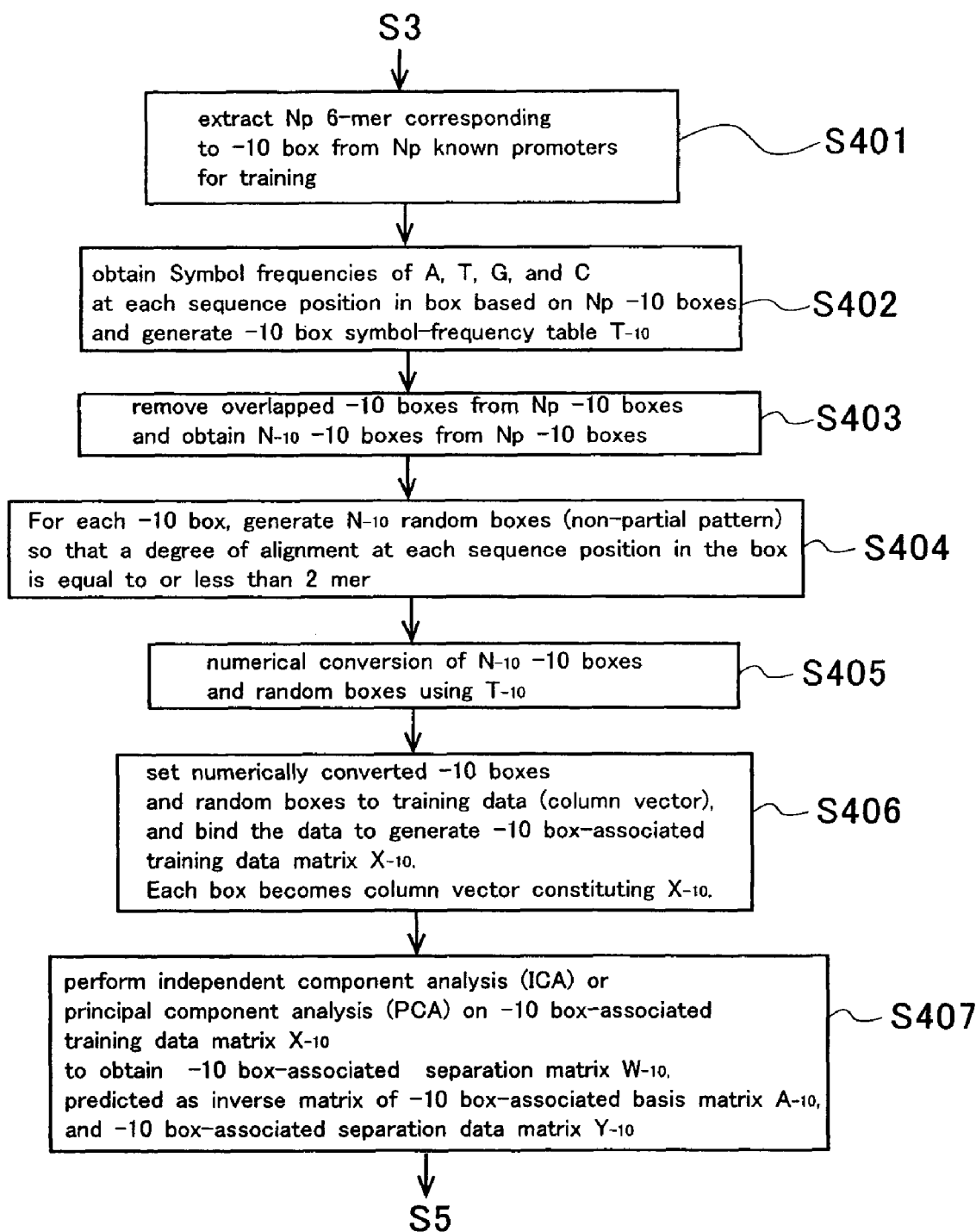
FIG. 11 is a flowchart illustrating a flow of −10 box training according to the first embodiment.

The −35 box-associated analyzing means 21E performs pre-processes such as a mean-value-to-zero normalization process and a whitening process on the −35 box-associated training data matrix $X_{-35}$ (see FIG. 8) generated by the −35 box-associated training data matrix-generating means 21D (see FIG. 9) and an independent component analysis (ICA) by using the pre-processed −35 box-associated training data matrix $X_{-35}$ so as to obtain a −35 box-associated separation matrix $X_{-35}$ and a −35 box-associated separation data matrix $Y_{-35}$ (see FIG. 10 and Step S307 of FIG. 4). The −35 box-associated analyzing means 21E stores the obtained $W_{-35}$ in the −35 box-associated separation matrix storage means 42 (see FIG. 1) and the obtained $Y_{-35}$ in the −35 box-associated separation data matrix storage means 43 (see FIG. 1).

The −10 box training means 22 includes a −10 box symbol-frequency table-generating means 22A that is a second-partial-pattern symbol-frequency table-generating means, random box-generating means 22B that is a second non-partial pattern-generating means, −10 box-associated numerical conversion means 22C that is a second-partial-pattern numerical conversion means, −10 box-associated training data matrix-generating means 22D that is a second-partial-pattern training data matrix-generating means, and −10 box-associated analyzing means 22E that is a second-partial-pattern analyzing means.

The −10 box symbol-frequency table-generating means 22A obtains symbol frequencies of the symbols A, T, G, and C at each sequence position in multiple types of known −10 boxes by using nucleotide information of the −10 boxes and generates the −10 box symbol-frequency table $T_{-10}$ (see FIG. 12) by corresponding the symbol frequencies to the sequence positions and symbols in the −10 boxes (see Step S402 of FIG. 11). The −10 box symbol-frequency table-generating means 22A stores the generated $T_{-10}$ in the −10 box symbol-frequency table storage means 51 (see FIG. 1).

The random box-generating means 22B generates random boxes so as to prepare false data (column vectors of $C_{-10}^T$ shown in FIG. 14) among training data (column vectors) of the −10 box-associated training data matrix $X_{-10}$ (see FIG. 14) that is the second-partial-pattern training data matrix (see Step S404 of FIG. 11).

The −10 box-associated numerical conversion means 22C converts to numerals the known −10 boxes and the random boxes generated by the random box-generating means 22B according to the sequence positions in the boxes and the types of symbols A, T, G, and C by using the −10 box symbol-frequency table $T_{-10}$ (see FIG. 12) stored in the −10 box symbol-frequency table storage means 51 (see FIG. 1) and generates $B_{-10}$ (see FIG. 13) and $C_{-10}$ (see Step S405 of FIG. 11).

The −10 box-associated training data matrix-generating means 22D transposes the $B_{-10}$ (see FIG. 13) and the $C_{-10}$ obtained by the numerical conversion of the −10 box-associated numerical conversion means 22C into $B_{-10}^T$ and $C_{-10}^T$, respectively, and binds the −10 box-associated training data matrix $X_{-10}$ (see FIG. 14) (see Step S406 of FIG. 11). Alternatively, the order of the binding and the numerical conversion may be inverted.

Figure 14:
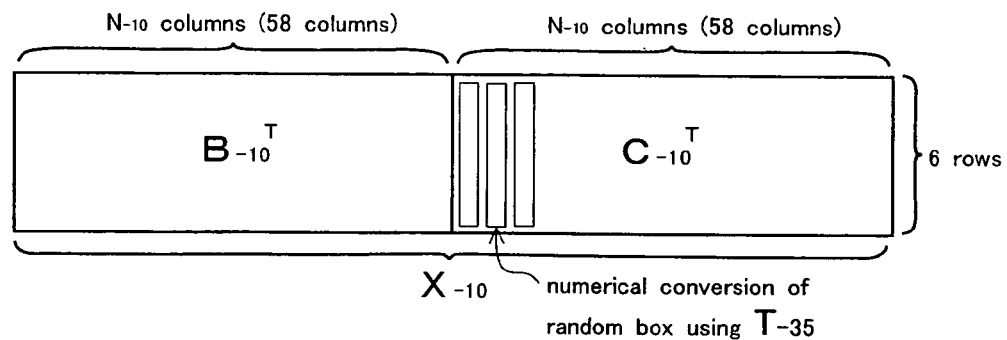
FIG. 14 is a third view for explaining a process in the −10 box training according to the first embodiment.
Figure 15:
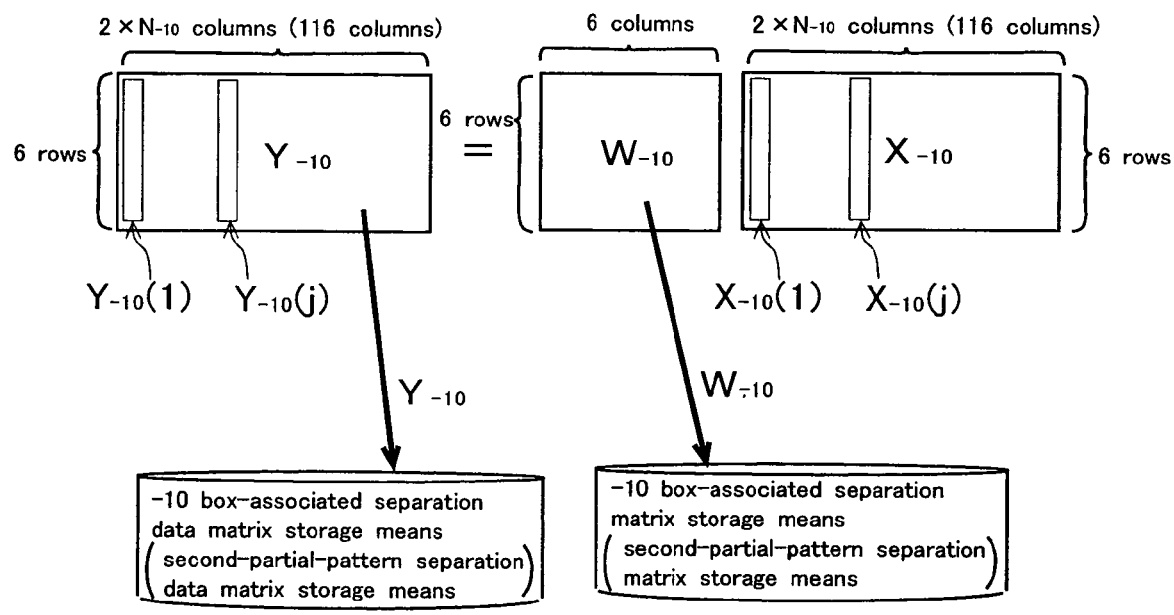
FIG. 15 is a fourth view for explaining a process in the −10 box training according to the first embodiment.

The −10 box-associated analyzing means 22E performs pre-processes such as a mean-value-to-zero normalization process and a whitening process on the −10 box-associated training data matrix $X_{-10}$ (see FIG. 14) generated by the −10 box-associated training data matrix-generating means 22D (similarly to FIG. 9) and an independent component analysis (ICA) by using the pre-processed −10 box-associated training data matrix $X_{-10}$ so as to obtain a −10 box-associated separation matrix $W_{-10}$ and a −10 box-associated separation data matrix $Y_{-10}$ (see FIG. 15 and Step S407 of FIG. 11). The −10 box-associated analyzing means 22E stores the obtained $W_{-10}$ in −10 box-associated separation matrix storage means 52 (see FIG. 1) and the obtained $Y_{-10}$ in the −10 box-associated separation data matrix storage means 53 (see FIG. 1).

The promoter training means 23 includes a promoter alignment processing means 23A that is a feature pattern alignment processing means, promoter symbol-frequency table-generating means 23B that is a whole-pattern symbol-frequency table-generating means, non-promoter-generating means 23C that is a non-feature pattern-generating means, non-promoter alignment processing means 23D that is non-feature pattern alignment processing means, promoter-associated numerical conversion means 23E that is a whole-pattern numerical conversion means, promoter-associated training data matrix-generating means 23F that is a whole-pattern training data matrix-generating means, and promoter-associated analyzing means 23G that is whole-pattern analyzing means.

The promoter alignment processing means 23A performs an alignment process for equalizing lengths of multiple types of known promoters to a constant length by inserting gaps (for example, indicated by a symbol "−") (see Step S501 of FIG. 16). Although the alignment process may be performed according a pre-defined rule, the alignment process can be performed according to a rule similar to that of an alignment process for a promoter candidate segment selected from test segments in a test step, and thus, detailed description thereof is made later (see FIG. 38). In addition, when the lengths of known promoters are previously equalized to a constant length according to the rule shown in FIG. 39, the process of the promoter alignment processing means 23A does not need to be performed. Although the lengths of known promoter are previously equalized to a constant length, if the lengths are equalized according to a rule different from the rule shown in FIG. 39, the promoter alignment processing means 23A removes the gaps and performs the alignment process again according to the rule shown in FIG. 38. In this case, similarly to later-described Steps S50302 (FIG. 17) to S50312 (FIG. 18), the −10 box-associated separation matrix $W_{-10}$ and the −35 box-associated separation matrix $W_{-35}$ are used to search for the −10 box and the −35 box, and after that, the alignment process is performed. However, when the −10 box and the −35 box are known, the alignment process is performed by using the known −10 box and −35 box.

The promoter symbol-frequency table-generating means 23B obtains symbol frequencies of the symbols A, T, G, C, and gap (for example, "−") at each sequence position in the whole pattern by using multiple types of the known promoters equalized to a constant length by the promoter alignment processing means 23A and generates a promoter symbol-frequency table $T_{prom}$ (see FIG. 19) by corresponding the symbol frequencies to the sequence positions and symbols in the whole pattern (see Step S502 of FIG. 16). The promoter symbol-frequency table-generating means 23B stores the generated $T_{prom}$ in the promoter symbol-frequency table storage means 61 (see FIG. 1).

The non-promoter-generating means 23C generates multiple types of non-promoters that are non-feature patterns of which whole lengths are equalized (see Step S503 of FIG. 16). The non-promoter-generating means 23C selects a plurality of partial pattern putative sequences having the same length (in this case, 6 mer) as that of each box and having nucleotide positions shifted by 1 mer (a plurality (j=1 to 9) of −10 box putative sequences shown in FIG. 20 and a plurality (j=1 to 7) of −35 box putative sequences shown in FIG. 22) among non-promoter-generating sequences (see FIG. 20) that is non-feature pattern-generating sequences prepared in order to generate a non-promoter, for each of the partial patterns in each region, that is, for the −10 box and the −35 box (see Steps S50303 and S50307 of FIG. 17) and converts to numerals a plurality of the partial pattern putative sequences according to the sequence positions and types of the symbols A, T, G, and C by using the partial-pattern symbol-frequency tables (−10 box symbol-frequency table $T_{-10}$ and −35 box symbol-frequency table $T_{-35}$) to generate partial pattern putative data (a plurality of putative −10 box data and a plurality of putative −10 box data) (see Steps S50304 and S50308 of FIG. 17).

Subsequently, the non-promoter-generating means 23C performs a matrix calculation of multiplying the partial-pattern separation matrix (−10 box-associated separation matrix $W_{-10}$ and −35 box-associated separation matrix $W_{-35}$) with a partial pattern putative data matrix (putative −10 box data matrix $Z_{-10}$ of FIG. 20 and putative −35 box data matrix $Z_{-35}$ of FIG. 22) in which a plurality of partial pattern putative data are bound to generate a partial pattern putative data-associated separation data matrix (putative −10 box data-associated separation data matrix $Y_{-10can}$ Y of FIG. 21 and putative −35 box data-associated separation data matrix $Y_{-35can}$ of FIG. 23) in which a plurality of the partial pattern putative data-associated separation data are bound (see Steps S50305 of FIG. 17 and Step S50309 of FIG. 18). Subsequently, the non-promoter generating means 23C obtains, among the generated partial pattern putative data-associated separation data (the putative −10 box data-associated separation data $Y_{-10can}$ (j) and the putative −35 box data-associated separation data $Y_{-35can}$ (j)), the partial pattern putative data-associated separation data of which the summation of the inner products of the partial pattern putative data-associated separation data $Y_{-10can}$ (j) and $Y_{-35can}$ (j) with column vectors $Y_{-10}$ (k) and $Y_{-35}$ (k) of true data-corresponding portions of the partial-pattern separation data matrix (the −10 box-associated separation data matrix $Y_{-10}$ of FIG. 21 and the −35 box-associated separation data matrix $Y_{-35}$ of FIG. 23) is maximized. The non-promoter-generating means 23C selects partial pattern putative sequences (any one of a plurality (j=1 to 9 of FIG. 20) of the −10 box putative sequences and any one of a plurality (j=1 to 7 of FIG. 22) of the −35 box putative sequences) corresponding to the obtained partial pattern putative data-associated separation data as partial pattern-corresponding sequences (a −10 box-corresponding sequences and −35 box-corresponding sequences) included in the non-promoter that is a non-feature pattern (see Step S50306 of FIG. 17 and Step S50310 of FIG. 18). The non-promoter-generating means 23C selects the non-promoter based on the selected partial pattern-corresponding sequences (the −10 box-corresponding sequences and the −35 box-corresponding sequences) in each region (see Step S50311 of FIG. 18). Although a process for obtaining the partial pattern putative data-associated separation data of which the summation of the inner products is maximized is performed, the partial pattern putative data-associated separation data which are closest to the column vectors $Y_{-10}$ (k) and $Y_{-35}$ (k) of true data-corresponding portions may be obtained. For example, in a case where the partial pattern putative data-associated separation data of which a similarity measure to a set of the column vectors $Y_{-10}$ (k) and $Y_{-35}$ (k) of true data-corresponding portions is maximized are obtained, the similarity measure instead of the "summation of inner products" may be used.

Figure 24:
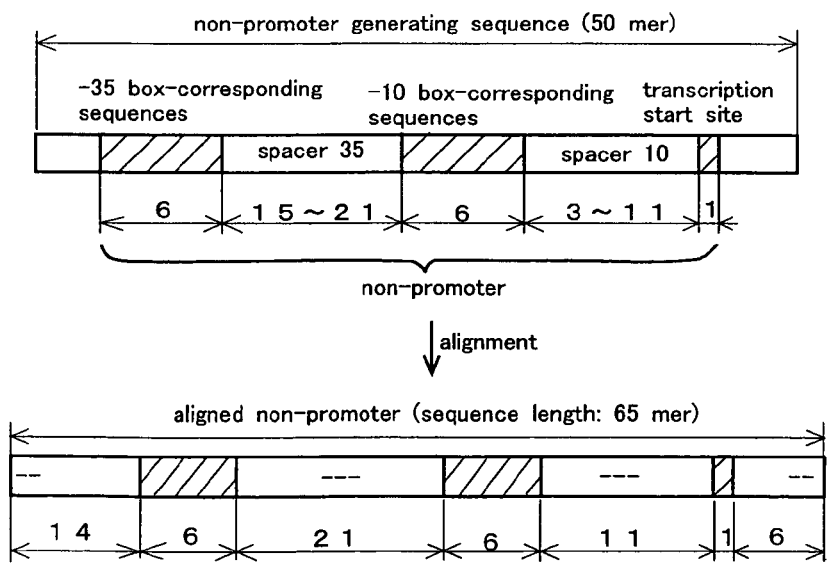
FIG. 24 is a sixth view for explaining a process in the promoter training according to the first embodiment.

The non-promoter alignment processing means 23D performs an alignment process for equalizing the lengths of the non-promoters to a constant length (in this case, sequence length: 65 mer) by inserting the gaps while each of the −10 box-corresponding sequences and the −35 box-corresponding sequences selected by the non-promoter generating means 23C is maintained to be in a one-body state (see Step S503 of FIG. 16, Step S50312 of FIG. 18, and FIG. 24).

Figure 25:
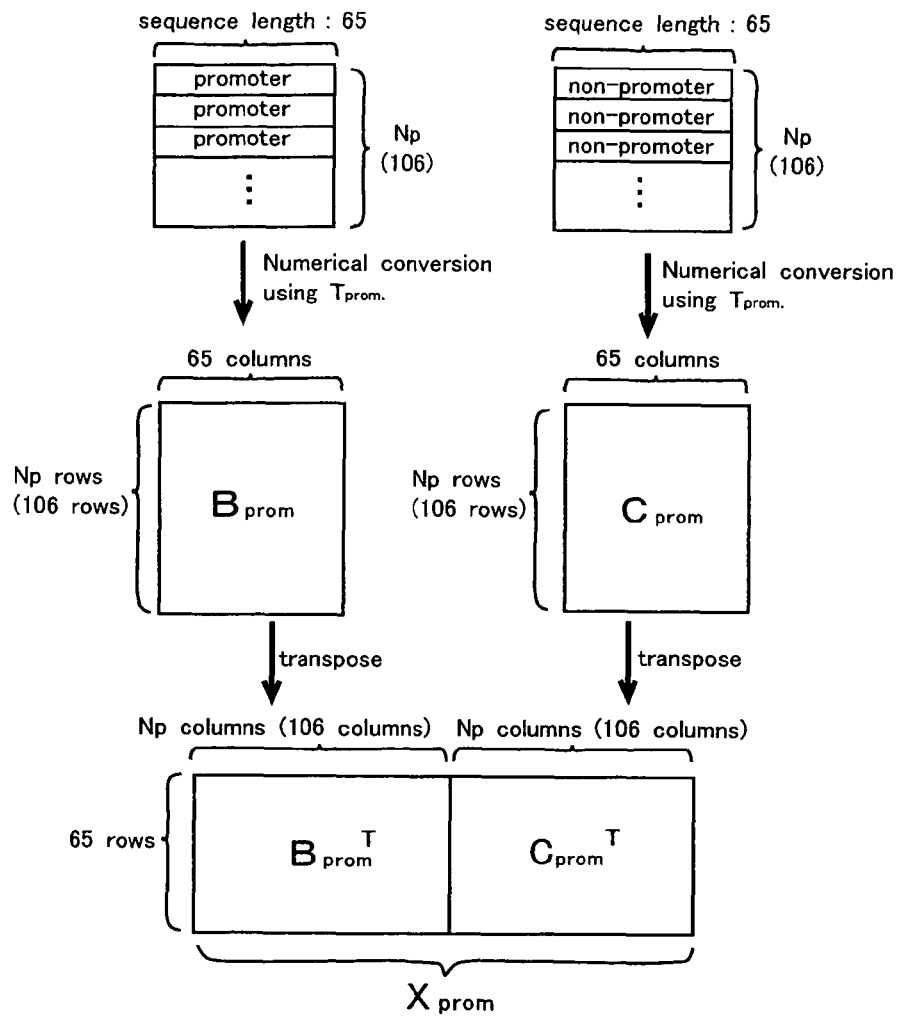
FIG. 25 is a seventh view for explaining a process in the promoter training according to the first embodiment.

The promoter-associated numerical conversion means 23E converts to numerals the promoter that includes multiple types of known feature patterns in which the lengths of whole patterns are equalized to a constant length (in this case, sequence length: 65 mer) by the promoter alignment processing means 23A and the non-promoter that includes multiple types of known non-feature patterns in which lengths of whole patterns are equalized to a constant length (in this case, sequence length: 65 mer) by the non-promoter alignment processing means 23D according to the sequence positions and types of symbols of A, T, G, C, and gap (for example, "−") by using the promoter symbol-frequency table $T_{prom}$ stored in the promoter symbol-frequency table storage means 61 (see FIG. 1) (see Step S504 of FIG. 16 and FIG. 25).

The promoter-associated training data matrix-generating means 23F transposes the $B_{prom}$ and the $C_{prom}$ (see FIG. 25) obtained by the numerical conversion of the promoter-associated numerical conversion means 23E into $B_{prom}^T$ and $C_{prom}^T$, respectively, and binds the $B_{prom}^T$ and the $C_{prom}^T$ to generate a promoter-associated training data matrix $X_{prom}$ (see FIG. 25) (see Step S505 of FIG. 16). Alternatively, the order of the binding and the numerical conversion may be inverted.

The promoter-associated analyzing means 23G performs pre-processes such as a mean-value-to-zero normalization process and a whitening process on the promoter-associated training data matrix $X_{prom}$ (see FIG. 25) generated by the promoter-associated training data matrix-generating means 23F (similarly to FIG. 9). The promoter-associated analyzing means 23G performs an independent component analysis (ICA) by using the pre-processed promoter-associated training data matrix $X_{prom}$ so as to obtain a promoter-associated separation matrix $W_{prom}$ and a promoter-associated separation data matrix $Y_{prom}$ (see FIG. 26 and Step S506 of FIG. 16). In addition, the promoter-associated analyzing means 23G stores the obtained $W_{prom}$ in the promoter-associated separation matrix storage means 62 (see FIG. 1) and the obtained $Y_{prom}$ in the promoter-associated separation data matrix storage means 63 (see FIG. 26). Although the $Y_{prom}$ is not used for processes in the following test step, the $Y_{prom}$ is obtained in order to check that a promoter is decided according to which sign (plus or minus) a value of the feature decision element (each element in the first row) of a separation data matrix $Y_{test}$ (see FIG. 38) obtained in a process of the test step has.

The correlation training means 24 includes correlation-binding sequence generating means 24A, correlation-decision symbol-frequency table-generating means 24B, non-correlation-binding sequence-generating means 24C, correlation-binding sequence numerical conversion means 24D, correlation-decision training data matrix-generating means 24E, and correlation-decision analyzing means 24F.

The correlation-binding sequence-generating means 24A binds the −35 box (6 mer) and the −10 box (6 mer) that are the known partial patterns with transcription-start-site neighborhood sequences (for example, 3 mer) that are the known specific-site neighborhood sequence to generate, for example, 15-mer correlation-binding sequences (see FIG. 28) (see Step S601 of FIG. 27). In the embodiment, the 15-mer correlation-binding sequences are exemplified, but if correlation-searchable feature portions are found in a spacer 10, a portion of the spacer 35, or other portions as a progression of technologies, these portions may be included to generate a correlation-binding sequences. In this case, these found portions may be selected as the partial patterns in the present invention. Accordingly, the later-described non-correlation-binding sequences (see FIG. 30) and correlation-decision sequences (see FIG. 37) are not limited to 15 nucleotides, but other portions may be included so as to generate a sequences.

The correlation-decision symbol-frequency table-generating means 24B obtains symbol frequencies of the symbols A, T, G, and C at each sequence position in multiple types of the correlation-binding sequences by using the correlation-binding sequences generated by the correlation-binding sequence-generating means 24A and generates a correlation-decision symbol-frequency table $T_{BBS}$ (see FIG. 29) by corresponding the symbol frequencies to the sequence positions and symbols in the correlation-binding sequences (see Step S601 of FIG. 27). The correlation-decision symbol-frequency table-generating means 24B stores the generated $T_{BBS}$ in the correlation-decision symbol-frequency table storage means 71 (see FIG. 1).

Figure 30:
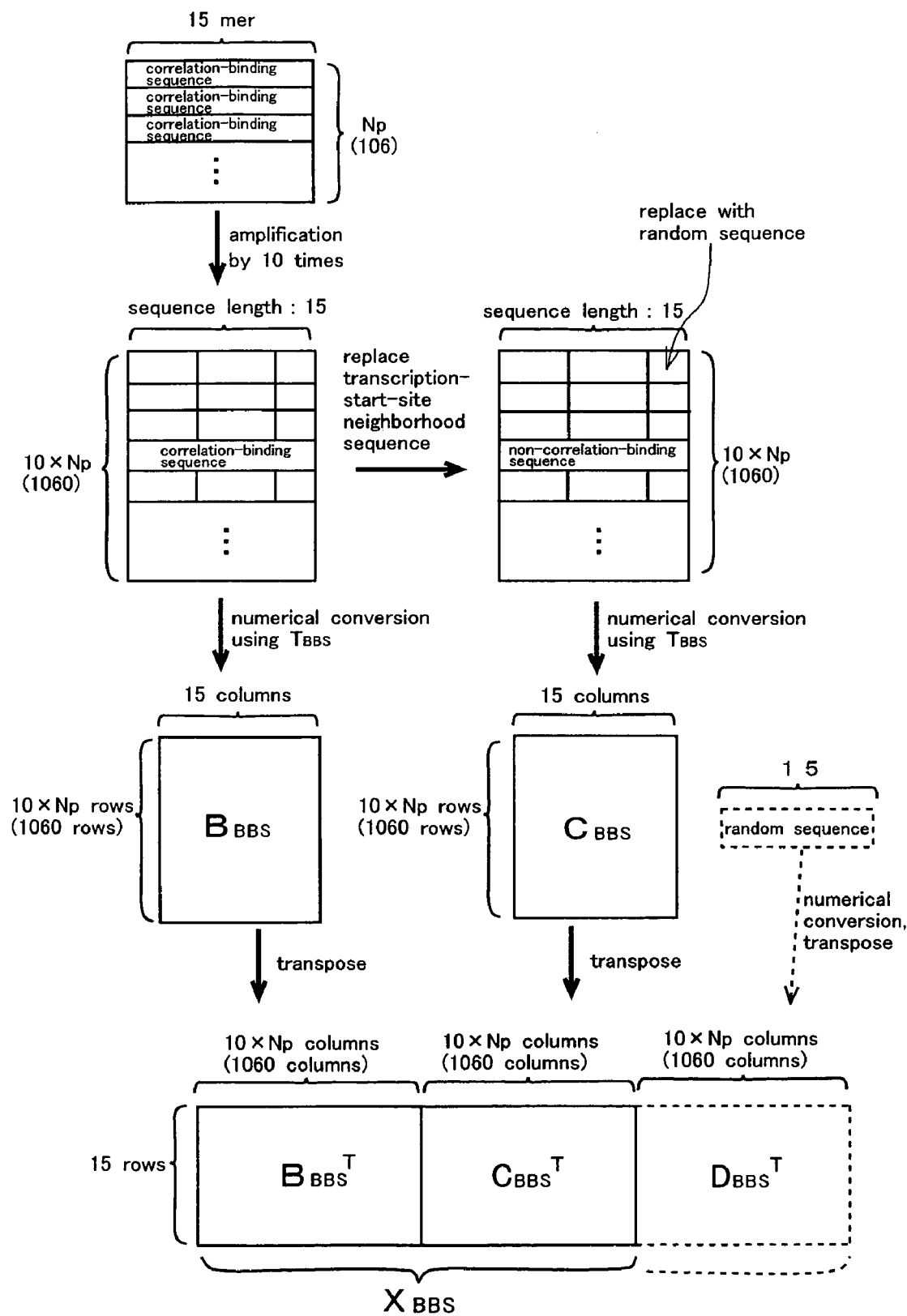
FIG. 30 is a third view for explaining a process in the correlation training according to the first embodiment.

The non-correlation-binding sequence-generating means 24C binds the known partial patterns, that is, the −35 box (6 mer) and the −10 box (6 mer) with a random sequence (for example, 3 mer) that is a non-specific-site neighborhood sequence different from the known specific-site neighborhood sequences, that is, the transcription-start-site neighborhood sequences to generate, for example, 15-mer non-correlation-binding sequences (see Step S603 of FIG. 27 and FIG. 30).

The correlation-binding sequence numerical conversion means 24D converts to numerals the correlation-binding sequence and the non-correlation-binding sequence (see FIG. 30) according to the sequence positions in the boxes and the types of symbols A, T, G, and C by using the correlation-decision symbol-frequency table $T_{BBS}$ (see FIG. 29) stored in the correlation-decision symbol-frequency table storage means 71 (see FIG. 1) (see Step S604 of FIG. 27 and FIG. 30).

The correlation-decision training data matrix-generating means 24E transposes the $B_{BBS}$ and the $C_{BBS}$ (see FIG. 30)

obtained by the numerical conversion of the correlation-binding sequence numerical conversion means 24D into $B_{ins}^T$ and $C_{BBS}^T$, respectively, and binds the $B_{BBS}^T$ and the $C_{BBS}^T$ to generate a correlation-decision training data matrix $X_{BBS}$ (see FIG. 30) (see Step S605 of FIG. 27 and FIG. 30). Alternatively, the order of the binding and the numerical conversion may be inverted.

The correlation-decision analyzing means 24F performs pre-processes such as a mean-value-to-zero normalization process and a whitening process (similarly to FIG. 9) on the correlation-decision training data matrix $X_{BBS}$ (see FIG. 30) generated by the correlation-decision training data matrix-generating means 24E and an independent component analysis (ICA) by using the pre-processed correlation-decision training data matrix $X_{BBS}$ so as to obtain a correlation-decision separation matrix $W_{BBS}$ and a correlation-decision separation data matrix $Y_{BBS}$ (see Step S606 of FIG. 27 and FIG. 31). The correlation-decision analyzing means 24F stores the obtained $W_{BBS}$ in the correlation-decision separation matrix storage means 72 (see FIG. 1) and the obtained the $Y_{BBS}$ in the correlation-decision separation data matrix storage means 73 (see FIG. 31). Although the $Y_{BBS}$ is not used for the following processes in the test step, the $Y_{BBS}$ is obtained so as to be used to decide whether the values of the correlation-decision elements (elements of the first row) of a correlation-decision separation data matrix $Y_{BBS}$, (see FIG. 37) obtained in the test step are plus or minus values.

Referring to FIG. 1, the test processing means 30 includes test data-generating means 31, separation processing means 32, and decision means 33.

The test data-generating means 31 includes putative −35 box data-generating means 31A that is a first putative partial pattern data-generating means, putative −10 box data generating means 31B that is a second putative partial pattern data-generating means, putative −35 box extracted data-generating means 31C that is a first putative partial pattern data-associated separation data-generating means, a putative −10 box data-associated separation data-generating means 31D that is a second putative partial pattern data-associated separation data-generating means, a −35 box-corresponding sequences selection means 31E that is a first partial pattern-corresponding sequences selection means, a −10 box-corresponding sequences selection means 31F that is a second partial pattern-corresponding sequences selection means, a promoter candidate segment selection means 31G that is feature pattern putative sequence selection means, alignment processing means 31H, and a promoter candidate segment numerical conversion means 31J that is feature pattern putative sequence numerical conversion means.

Figure 22:
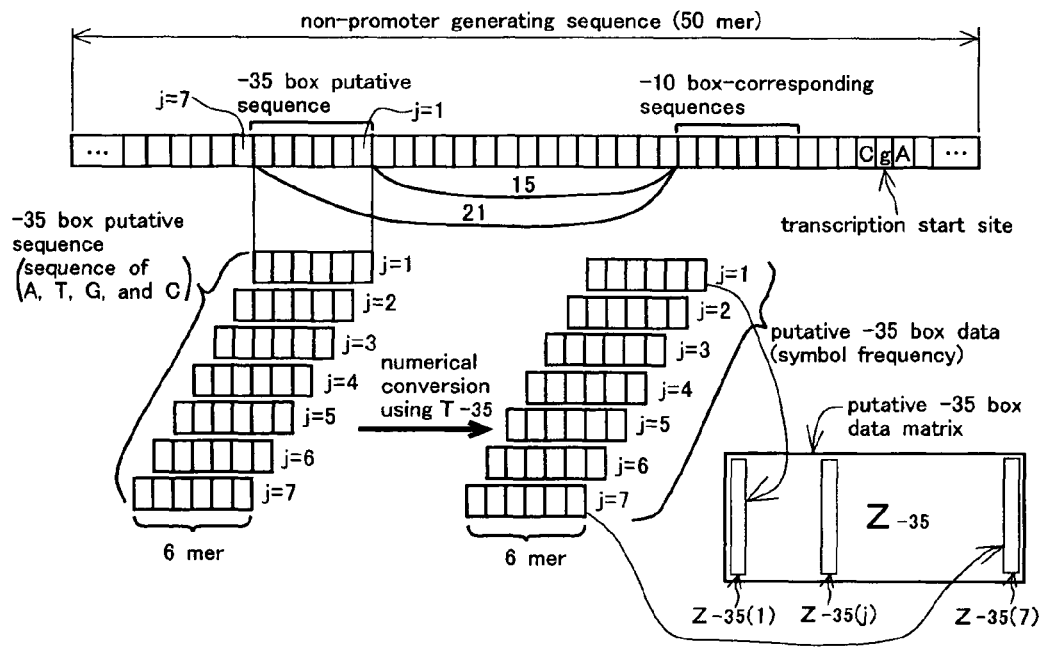
FIG. 22 is a fourth view for explaining a process in the promoter training according to the first embodiment.

The putative −35 box data-generating means 31A selects a plurality of −35 box putative sequences having the same lengths (6 mer) as that of the −35 box and having nucleotide positions shifted by 1 mer among the test segments extracted from a to-be-decided DNA sequence or a DNA segment thereof (see Step S1306 of FIG. 33, similar to FIG. 22) and converts to numerals a plurality of the −35 box putative sequences according to the sequence positions and types of the symbols A, T, G, and C by using the −35 box symbol-frequency table $T_{-35}$ stored in the −35 box symbol-frequency table storage means 41 (see FIG. 1) to generate a plurality of putative −35 box data (see Step S1307 of FIG. 33, similar to FIG. 22 and generation of putative −10 box data of FIG. 36). The putative −35 box data-generating means 31A selects a plurality of the −35 box putative sequences with reference to the −10 box-corresponding sequences selected by the −10 box-corresponding sequences selection means 31F so that an interval (corresponding to the spacer 35) between the −10 box-corresponding sequences and the −35 box putative sequences is 15 to 21 mer. Therefore, in a case where the putative −10 box data-generating means 31B sets a plurality of transcription start sites in a one-nucleotide-shifted manner as described later, since a plurality of the −10 box-corresponding sequences are selected by the −10 box-corresponding sequences selection means 31F, the putative −35 box data generating means 31A defines a plurality of the −35 box putative sequences for each transcription start site of each of the −10 box-corresponding sequences with reference to each of the −10 box-corresponding sequences.

The putative −10 box data generating means 31B selects a transcription start site among the test segment extracted from the to-be-decided DNA sequence or the DNA segment (see Step S1301 of FIG. 33). In addition, the putative −10 box data generating means 31B selects a plurality of −10 box putative sequences having the same lengths (6 mer) as that of the −10 box and having nucleotide positions shifted by 1 mer with reference to the designated transcription start site, so that an interval (corresponding to a spacer 10) between the −10 box putative sequences and the transcription start site is 3 to 11 mer (see Step S1302 of FIG. 33 and FIG. 36). The putative −10 box data-generating means 31B converts to numerals a plurality of the −10 box putative sequence according to the sequence positions and the types of symbols A, T, G, and C by using the −10 box symbol-frequency table $T_{-10}$ stored in the −10 box symbol-frequency table storage means 51 (see FIG. 1) to generate a plurality of putative −10 box data (see Step S1303 of FIG. 33 and FIG. 36). Although the putative −10 box data-generating means 31B may be constructed to select one transcription start site from one test segment, as shown in FIG. 36, in order to improve a recognition accuracy, it is preferable that a plurality of the transcription start sites are selected from one test segment by shifting by 1 mer and a plurality of the −10 box putative sequences are selected for each of the transcription start sites (see Steps S1311 and S1312 of FIG. 34).

Figure 23:
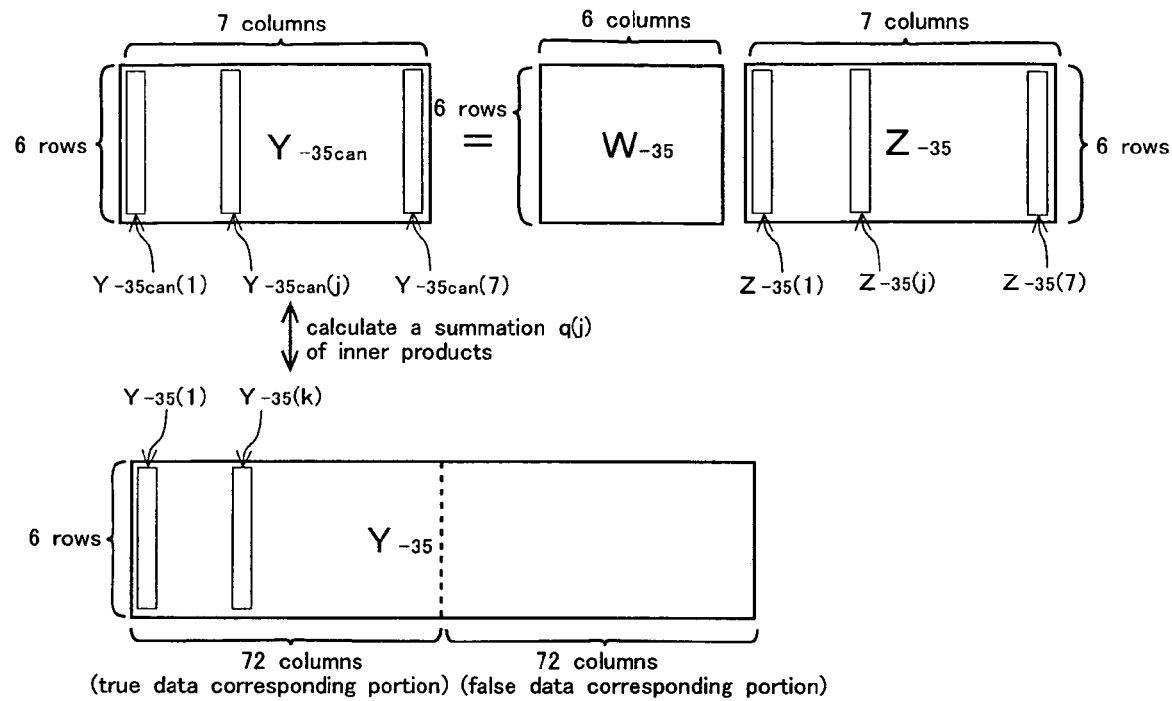
FIG. 23 is a fifth view for explaining a process in the promoter training according to the first embodiment.

The putative extracted data-generating means for −35 boxes 31C performs a matrix calculation of multiplying the −35 box-associated separation matrix $W_{-35}$ stored in the −35 box-associated separation matrix storage means 42 (see FIG. 1) with a putative −35 box data matrix $Z_{-35}$ in which a plurality of the putative −35 box data generated by the putative −35 box data-generating means 31A are bound to generate a putative −35 box data-associated separation data matrix $Y_{-35can}$ in which a plurality of the putative −35 box data-associated separation data are bound (see Step S1308 of FIG. 34, similarly to FIG. 23).

Figure 21:
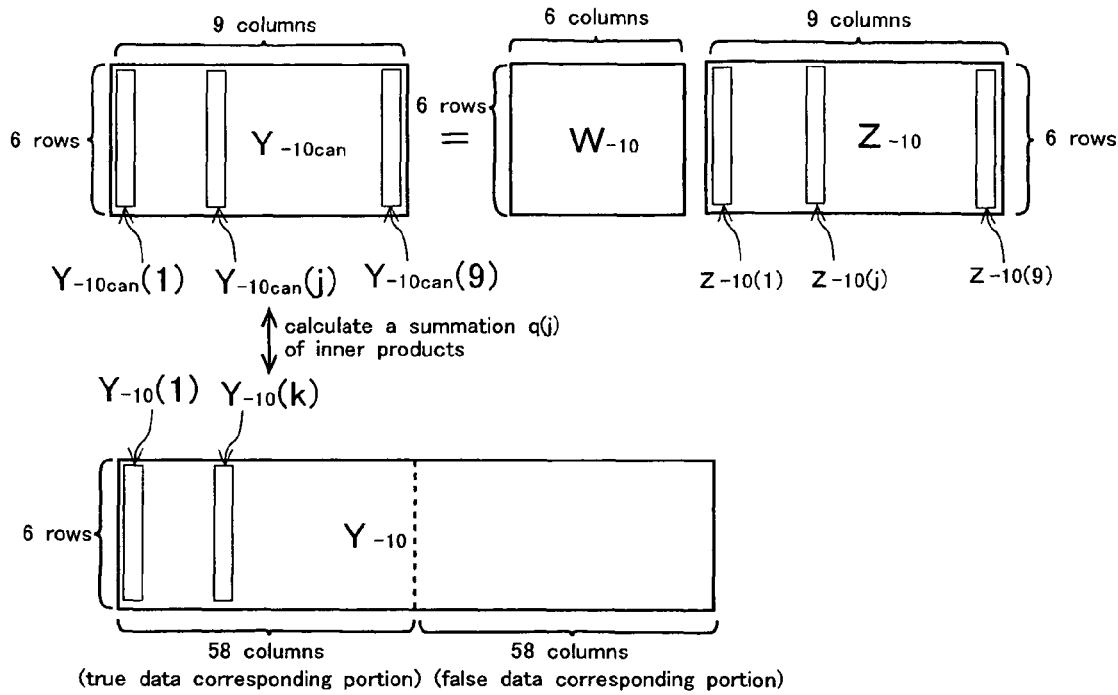
FIG. 21 is a third view for explaining a process in the promoter training according to the first embodiment.

The putative −10 box data-associated separation data-generating means 31D performs a matrix calculation of multiplying the −10 box-associated separation matrix $W_{-10}$ stored in the −10 box-associated separation matrix storage means 52 (see FIG. 1) with a putative −10 box data matrix $Z_{-10}$ in which a plurality of the putative −10 box data generated by the putative −10 box data-generating means 31B are bound to generate a putative −10 box data-associated separation data matrix $Y_{-10can}$ in which a plurality of the putative −10 box data-associated separation data are bound (see Step S1304 of FIG. 33, similarly to FIG. 21).

The −35 box-corresponding sequences selection means 31E obtains, among a plurality of the putative −35 box data-associated separation data (that is, the column vector $Y_{-35can}$ (j) constituting the putative −35 box data-associated separation data matrix $Y_{-35can}$) generated by the putative extracted data-generating means for −35 boxes 31C, the putative −35 box data-associated separation data of which summation q(j) of inner products of the putative −35 box data-associated separation data $Y_{-35can}$ (j) with the column vectors $Y_{-35}$ (k) of true data-corresponding portions of the −35 box-associated separation data matrix $Y_{-35}$ is maximized (similarly to FIG. 23). The −35 box-corresponding sequences selection means 31E selects a −35 box putative sequence (similarly to FIG. 22, any one of a plurality (j=1 to 7) of the −35 box putative sequences) corresponding to the obtained putative −35 box data-associated separation data as a −35 box-corresponding sequence (see Step S1309 of FIG. 34). Although a process for obtaining the putative −35 box data-associated separation data of which summation q(j) of inner products is maximized is performed, the putative −35 box data-associated separation data which are closest to the column vectors $Y_{-35}$ (k) of the true data-corresponding portion of the −35 box-associated separation data matrix $Y_{-35}$ may be obtained. In a case where the putative −35 box data-associated separation data of which similarity measure to a set of the column vector $Y_{-35}$ (k) of the true data-corresponding portion of the −35 box-associated separation data matrix $Y_{-35}$ is maximized are obtained, other similarity measures instead of the "summation of inner products" may be used.

The −10 box-corresponding sequences selection means 31F obtains, among a plurality of the putative −10 box data-associated separation data (that is, the column vectors $Y_{-10can}$ (j) constituting the putative −10 box data-associated separation data matrix $Y_{-10can}$) generated by the putative −10 box data-associated separation data-generating means 31D, the putative −10 box data-associated separation data of which summation q(j) of inner products of the putative −10 box data-associated separation data $Y_{-10can}$ (j) with the column vectors $Y_{-10}$ (k) of true data-corresponding portions of the −10 box-associated separation data matrix $Y_{-10}$ is maximized (similarly to FIG. 21). The −10 box-corresponding sequences selection means 31F selects a −10 box putative sequence (similarly to FIG. 20, any one of a plurality (j=1 to 9) of the −10 box putative sequences) corresponding to the obtained putative −10 box data-associated separation data as a −10 box-corresponding sequence (see Step S1305 of FIG. 33). Although a process for obtaining the putative −10 box data-associated separation data of which summation q(j) of inner products is maximized is performed, the putative −10 box data-associated separation data which are closest to the column vectors $Y_{-10}$ (k) of true data corresponding portion of the −10 box-associated separation data matrix $Y_{-10}$ may be obtained. In a case where the putative −10 box data-associated separation data of which similarity measure to a set of the column vector $Y_{-10}$ (k) of the true data-corresponding portion of the −10 box-associated separation data matrix $Y_{-10}$ is maximized are obtained, other similarity measures instead of the "summation of inner products" may be used.

The promoter candidate segment selection means 31G selects a promoter candidate segment based on the −35 box-corresponding sequence selected by the −35 box-corresponding sequences selection means 31E, the −10 box-corresponding sequence selected by the −10 box-corresponding sequences selection means 31F, and the transcription start sites corresponding thereto (see Step S1310 of FIG. 34 and FIG. 37).

The promoter candidate segment selection means 31G decides whether or not there is a correlation of the selected −35 box-corresponding sequences and −10 box-corresponding sequences to the transcription-start-site neighborhood sequences including the corresponding transcription start sites, and if there is no correlation, does not perform a process for deciding a promoter candidate segment based on the −35 box-corresponding sequences, the −10 box-corresponding sequences, and the transcription start sites in the transcription-start-site neighborhood sequences. Namely, the sequences selected from the −35 box-corresponding sequences, the −10 box-corresponding sequences, the transcription start sites in the transcription-start-site neighborhood sequences are not used as a promoter candidate segment.

More specifically, the promoter candidate segment selection means 31G binds the selected −35 box-corresponding sequences and −10 box-corresponding sequences and the transcription-start-site neighborhood sequences including the corresponding transcription start sites to generate correlation-decision sequences. The promoter candidate segment selection means 31G converts to numerals the correlation-decision sequences according to the sequence positions and types of symbols A, T, G, and C by using the correlation-decision symbol-frequency table $T_{BBS}$ stored in the correlation-decision symbol-frequency table storage means 71 (see FIG. 1) to generate correlation-decision data. The promoter candidate segment selection means 31G performs a matrix calculation of multiplying the correlation-decision data matrix $W_{BBS}$ stored in the correlation-decision separation matrix storage means 72 (see FIG. 1) with the correlation-decision data or a correlation-decision separation matrix $X_{BBS,test}$ in which a plurality of the correlation-decision data are bound, so that a correlation-decision separation process for obtaining correlation-decision separation data or a correlation-decision separation data matrix $Y_{BBS,test}$ in which a plurality of the correlation-decision separation data are bound is performed. After that, it is decided whether or not there is a correlation by deciding at which side of a predetermined correlation-decision threshold (for example, zero) exists a value of a correlation-decision element (for example, each element of the first row and, in the case of a vector, a first element) selected according to a position of a matrix of feature elements (for example, elements of the first column) included in a predicted correlation-decision basis matrix $W_{BBS}^{-1}$ among the correlation-decision separation data or the elements of the correlation-decision separation data matrix $Y_{BBS,test}$ obtained by the correlation-decision separation process (see Steps S13101 to S13104 of FIG. 35 and FIG. 37).

The alignment processing means 31H performs an alignment process for equalizing the lengths of the promoter candidate segments selected by the promoter candidate segment selection means 31G to a constant length (in this case, sequence length: 65 mer) by inserting the gaps (for example, "−") according to a predetermined rule (described later in detail) (see Step S14 of FIG. 32 and FIG. 38).

The promoter candidate segment numerical conversion means 31J converts to numerals the promoter candidate segments (see FIG. 38) aligned by the alignment processing means 31H according to the sequence positions and types of symbols of A, T, G, C, and gap (for example, "−") by using the promoter symbol-frequency table $T_{prom}$ (see FIG. 19) stored in the promoter symbol-frequency table storage means 61 (see FIG. 1) and generates the test data (see Step S15 of FIG. 32 and FIG. 38).

The separation processing means 32 performs pre-processes on the test data (column vector) generated by the test data-generating means 31 or the test data matrix $X_{test}$ in which a plurality of the test data are bound. Next, the separation processing means 32 performs a matrix calculation of multiplying the promoter-associated separation matrix $W_{prom}$ stored in the promoter-associated separation matrix storage means 62 (see FIG. 1) with the processed test data (column vector) or the test data matrix $X_{test}$ in which a plurality of the test data are bound to generate separation data or a separation data matrix $Y_{test}$ in which a plurality of the separation data are bound (see Step S16 of FIG. 32 and FIG. 38).

In addition, in a case where a plurality of the promoter candidate segments are selected from one test segment (see FIG. 36), the separation processing means 32 performs the separation process on each of the test data obtained from each of the promoter candidate segments and obtains a plurality of the separation data for one test segment or the separation data matrix $Y_{test}$ in which a plurality of the separation data are bound.

The decision means 33 decides whether or not one of multiple types of known promoters or a new promoter similar to the known promoters is included in a test segment extracted from a to-be-decided DNA sequence or DNA segment by deciding at which side of a predetermined threshold (for example, zero) exists a value of a feature decision element (for example, each element of the first row and, in the case of a vector, a first element) selected according to a position in a matrix of feature elements (for example, elements of the first column) included in a predicted basis matrix $W_{prom}^{-1}$ among the separation data or the elements of the separation data matrix $Y_{test}$ obtained by the separation processing means 32 (see Step S17 of FIG. 32).

In a case where a plurality of promoter candidate segments are selected from one test segment (see FIG. 36), the decision means 33 decides at which side of a predetermined threshold (for example, zero) exists a value of a feature decision element (for example, each element of the first row and, in the case of a vector, a first element) selected according to a position in a matrix of feature elements (for example, elements of the first column) included in a predicted basis matrix $W_{prom}^{-1}$ among a plurality of the separation data or the elements of the separation data matrix $Y_{test}$ in which a plurality of the separation data are bound, for one test segment obtained by the separation processing means 32, obtains a value of the feature decision element having the largest absolute value of differences to the threshold among the values of the feature decision elements having the value (for example, a plus value) indicating the promoter, and recognizes the promoter candidate segment corresponding to the test data designated with the value of the obtained feature decision element as one of the multiple types of known promoters or the new promoter similar to the known promoters.

In the above-described embodiment, the training means 20 and the test processing means 30 are implemented with a central processing unit (CPU) provided in a computer (a personal computer, a high-performance computer thereof, or a low-performance thereof) constituting the promoter recognition system 10 and one or more programs for controlling operational sequences of the CPU.

In addition, the training means 20 and the test processing means 30 need not to be implemented with physically the same computer, but they may be implemented with different computers.

In addition, the processing means 21 (21A to 21E), 22 (22A to 22E), 23 (23A to 23G), and 24 (24A to 24F) included in the training means 20 are not limited to the ones implemented with one computer or one CPU, but they may be implemented by performing distributed processes (including functional distributed processes for each of the processing means 21 (21A to 21E), 22 (22A to 22E), 23 (23A to 23G), and 24 (24A to 24F) and parallel distributed process for increasing the processing speed) in a plurality of computers. The processing means 31 (31A to 31J), 32, and 33 included in the test processing means 30 may also be implemented in the same manner.

In addition, since various processes in the training step are not necessarily performed as an on-line process, at least some of the processes of the training means 20 may be performed as a manual calculation. However, in terms of the reduction of labor of users and facilitation of re-training for a newly found promoter, it is preferable that the various processes in the training step are performed as a computer process by the training means 20 like the embodiment.

In addition, the storage means 41 to 43, 51 to 53, 61 to 63, and 70 (71 to 73) may be implemented by using, for example, a hard disk, ROM, EEPROM, flash memory, RAM, MO, CD-ROM, CD-R, CD-RW, DVD-ROM, DVD-RAM, FD, magnetic tape, or a combination thereof.

In the second embodiment, recognition of promoter in a DNA sequence is performed by the promoter recognition system 10 as follows.

<Training Step>

Referring to FIG. 3, firstly, a computer constituting the promoter recognition system 10 is powered on to drive programs for various processes in the training step (Step S1). Next, Np known promoters for training are prepared. As an example of the embodiment, Np (for example, 106) analyzed *Escherichia coli* promoters shown in FIG. 5 and disclosed in Non-Patent Document 1 are used (Step S2). Next, a −35 box training process (Step S3) is performed.

(−35 Box Training)

Referring to FIG. 4, Np (106) 6 nucleotides (known nucleotides) corresponding to the −35 boxes are extracted from the Np (106) known training promoters shown in FIG. 5 (Step S301).

Next, the −35 box symbol-frequency table-generating means 21A obtains symbol frequencies of the symbols A, T, G, and C at each sequence position in the −35 boxes by using nucleotide information of the Np (106) −35 boxes, generates the −35 box symbol-frequency table $T_{-35}$ shown in FIG. 6 by corresponding the symbol frequencies to the sequence positions 1 to 6 and the symbols A, T, G, and C in the −35 boxes (Step S302 of FIG. 4), and stores the generated $T_{-35}$ in the −35 box symbol-frequency table storage means 41 (see FIG. 1).

In FIG. 6, $f_{A,-35\ (1)}$, $f_{A,-35\ (2)}$, $f_{A,-35\ (3)}$, . . . denote the symbol frequencies of A at the first, second, third, . . . in the −35 box, and $f_{T,-35\ (1)}$, $f_{T,-35\ (2)}$, $f_{T,-35\ (3)}$, . . . denote the symbol frequencies of T at the first, second, third, . . . in the −35 box. Like reference numerals are used for the symbols G and C. In addition, numbers vertically listed in the −35 box symbol-frequency table $T_{-35}$, that is, the symbol frequencies of A, T, G, C at the same position in the −35 box are normalized so as for a sum of the numbers to be 1.0. For example, $f_{A,-35\ (1)} + f_{T,-35\ (1)} + f_{G,-35\ (1)} + f_{C,-35\ (1)} = 1.0$. Other symbol-frequency tables $T_{-35}$, $T_{-10}$, $T_{prom}$, and $T_{BBS}$ are also normalized in the same manner. However, in the normalization, the sum is not necessarily 1.0, but the sum may be, for example, 1000.

Subsequently, overlapped −35 boxes are removed from the Np −35 boxes, so that the number of −35 boxes is reduced from Np to $N_{-35}$ (for example, 72) (Step S303 of FIG. 4). In addition, even in case of different types of promoters, since the −35 boxes may be the same, the overlap may occur.

Figure 8:
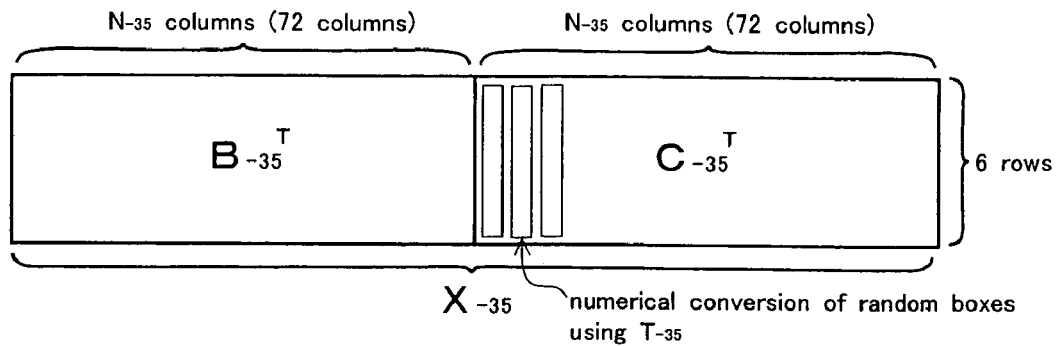
FIG. 8 is a third view for explaining a process in the −35 box training according to the first embodiment.

Next, the random box-generating means 21B generates $N_{-35}$ (72) 6-mer random boxes so as to prepare false data (column vectors of $C_{-35}^T$ shown in FIG. 8) among training data (column vectors) of the −35 box-associated training data matrix $X_{-35}$ shown in FIG. 8 (Step S304 of FIG. 4). At this time, the random box-generating means 21B generates the random boxes so that a degree of alignment at each sequence position in the boxes is equal to or less than two nucleotides. In the embodiment, the number of −35 boxes prepared for generating the −35 box-associated training data matrix $X_{-35}$ is equal to the number of the random boxes, that is, $N_{-35}$ (72), but the present invention is not limited to the same number. For example, when the feature of the −35 boxes is dominant, the number of the random boxes may be set to be larger than that of the −35 boxes. Other training data matrixes $X_{-10}$, $X_{prom}$, and $X_{BBS}$ may be generated in the same manner.

The −35 box-associated numerical conversion means 21C converts to numerals the known −35 Boxes and the random boxes generated by the random box-generating means 21B according to the sequence positions in the boxes and the types of symbols A, T, G, and C by using the −35 box symbol-frequency table $T_{-35}$ (see FIG. 6) stored in the −35 box symbol-frequency table storage means 41 (see FIG. 1) and generates $B_{-35}$ (see FIG. 7) and $C_{-35}$ (Step S305 of FIG. 4).

Subsequently, the −35 box-associated training data matrix-generating means 21D transposes the $B_{-35}$ (see FIG. 7) and $C_{-35}$ obtained by the numerical conversion of the −35 box-associated numerical conversion means 21C into $B_{-35}^T$ and $C_{-35}^T$, respectively, and binds the $B_{-35}^T$ and $C_{-35}^T$ to generate a −35 box-associated training data matrix $X_{-35}$ shown in FIG. 8 (Step S306 of FIG. 4). Referring to FIG. 8, the data obtained by converting to numerals the −35 boxes and the random boxes by using $T_{-35}$ are shown to be column vectors constituting the −35 box-associated training data matrix $X_{-35}$. Here, the $B_{-35}^T$ denotes a portion of the −35 box as true data, and the $C_{-35}^T$ denotes a portion of the random box as false data.

Next, the −35 box-associated analyzing means 21E performs pre-processes such as a mean-value-to-zero normalization process and a whitening process on the −35 box-associated training data matrix $X_{-35}$ (see FIG. 8) generated by the −35 box-associated training data matrix-generating means 21D. As shown in FIG. 9, firstly, the mean-value-to-zero normalization process is performed on each row of the −35 box-associated training data matrix $X_{-35}$ to set an average of values of elements in each row to zero. Secondly, the whitening process is performed by adding the column vectors $X_{-35}$ (j) (j=1 to 144) of the $X_{-35}$ and a product $X_{-35}$ (j) $X_{-35}$ (j)$^T$ of the column vectors $X_{-35}$ (j) and transposed vectors $X_{-35}$ (j)$^T$ over j=1 to 144 to generate a 6×6 covariance matrix R. Next, a diagonal matrix D (a matrix having zero elements except for diagonal elements) in which eigenvalues $\lambda_1$ to $\lambda_6$ of the covariance matrix R are arrayed diagonally in the descending order is obtained, and a matrix G in which eigenvectors corresponding to the eigenvalues $\lambda_1$ to $\lambda_6$ are arrayed in columns is obtained. Next, by using $V=D^{-1/2}G^T$, a matrix calculation process for multiplying the V with each of column vectors $X_{-35}$ (j) (j=1 to 144) of the $X_{-35}$ and the obtained $VX_{-35}$ (j) is newly set to the $X_{-35}$ (j) (j=1 to 144), so that the pre-processed −35 box-associated training data matrix $X_{-35}$ is generated. Although the above-described processes are performed based on the covariance matrix R using linear transformation, the present invention is not limited thereto. Alternatively, in the present invention, a process based on a covariance matrix using nonlinear transformation of the $X_{-35}$ may be performed. Namely, the $X_{-35}$ (j) may be subjected to nonlinear transformation and, after that, the transformed $X_{-35}$ (j) may be set to a new $X_{-35}$ (j).

Next, as shown in FIG. 10, the −35 box-associated analyzing means 21E performs an independent component analysis (ICA) by using the pre-processed −35 box-associated training data matrix $X_{-35}$ and satisfies $Y_{-35}=W_{-35}X_{-35}$. In addition, the −35 box-associated analyzing means 21E obtains the −35 box-associated separation matrix $W_{-35}$ in which elements of $Y_{-35}$ are independent of each other and the −35 box-associated separation data matrix $Y_{-35}$ and stores the obtained $W_{-35}$ and $Y_{-35}$ in the −35 box-associated separation matrix storage means 42 and the −35 box-associated separation data matrix storage means 43 (see FIG. 1), respectively (Step S307 of FIG. 4). Here, the independent component analysis (ICA) is a process for obtaining a −35 box-associated separation matrix $W_{-35}$ in which the column vectors $Y_{-35}$ (j) of the $Y_{-35}$ are independent of each other. In addition, similarly to an independent component analysis (ICA) (Step S506 of FIG. 16) for obtaining the later-described promoter-associated separation matrix $W_{prom}$ and promoter-associated separation data matrix $Y_{prom}$, any kind of independent component analysis may be used. In addition, similarly to the case of obtaining the later-described promoter-associated separation matrix $W_{prom}$ and promoter-associated separation data matrix $Y_{prom}$, a principal component analysis (PCA) may be performed as a −35 box-associated analysis process, and dimension reduction may be performed. In addition, although the independent component analysis (ICA) for solving a linearity problem by using the aforementioned nonlinear transformation of the $X_{-35}$ as an input may be referred to as a nonlinear ICA, such a nonlinear independent component analysis (ICA) can be included in the present invention. In addition, although an independent component analysis (ICA) for solving a linearity problem by using training data obtained by linear or nonlinear transformation as an input may also be referred to as a nonlinear ICA, if objects of the present invention can be achieved by such a ICA, an approximation and linearization processes thereof can be included in the present invention.

(−10 Box Training)

Referring to FIG. 11, Np (106) 6 nucleotides (known nucleotides) corresponding to the −10 boxes are extracted from the Np (106) known training promoters shown in FIG. 5 (Step S401).

Next, the −10 box symbol-frequency table-generating means 22A obtains symbol frequencies of the symbols A, T, G, and C at each sequence position in the −10 boxes by using nucleotide information of the Np (106) −10 boxes, generates the −10 box symbol-frequency table $T_{-10}$ shown in FIG. 12 by corresponding the symbol frequencies to the sequence positions 1 to 6 and symbols A, T, G, and C in the −10 boxes (Step S402 of FIG. 11), and stores the generated $T_{-10}$ in the −10 box symbol-frequency table storage means 51 (see FIG. 1).

Subsequently, overlapped −10 boxes are removed from the Np −10 boxes, so that the number of −10 boxes is reduced from Np to $N_{-10}$ (for example, 58) (Step S403 of FIG. 11). In addition, even in case of different types of promoters, since the −10 boxes may be the same, the overlap may occur.

Next, the random box-generating means 22B generates $N_{-10}$ (58) 6-mer random boxes so as to prepare false data (column vectors of $C_{-10}^T$ shown in FIG. 14) among training data (column vectors) of the −10 box-associated training data matrix $X_{-10}$ shown in FIG. 14 (Step S404 of FIG. 11). At this time, the random box-generating means 22B generates the random boxes so that a degree of alignment at each sequence position in the boxes is equal to or less than two nucleotides. Since the role of the random box is a set of false data, non-promoter segments in known databases can be used instead.

The −10 box-associated numerical conversion means 22C converts to numerals the known −10 Boxes and the random boxes generated by the random box-generating means 22B according to the sequence positions in the boxes and the types of symbols A, T, G, and C by using the −10 box symbol-frequency table $T_{-10}$ (see FIG. 12) stored in the −10 box symbol-frequency table storage means 51 (see FIG. 1) and generates $B_{-10}$ (see FIG. 13) and $C_{-10}$ (Step S405 of FIG. 11).

Subsequently, the −10 box-associated training data matrix-generating means 22D transposes the $B_{-10}$ (see FIG. 13) and $C_{-10}$ obtained by the numerical conversion of the −10 box-associated numerical conversion means 22C into $B_{-10}{}^T$ and $C_{-10}{}^T$, respectively, and binds the $B_{-10}{}^T$ and $C_{-10}{}^T$ to generate a −10 box-associated training data matrix $X_{-10}$ shown in FIG. 14 (Step S406 of FIG. 11). Referring to FIG. 14, the data obtained by converting to numerals the −10 boxes and the random boxes by using $T_{-10}$ are shown to be column vectors constituting the −10 box-associated training data matrix $X_{-10}$. Here, the $B_{-10}{}^T$ denotes a portion of the −10 box as true data, and the $C_{-10}{}^T$ denotes a portion of the random box as false data.

Next, the −10 box-associated analyzing means 22E performs pre-processes such as a mean-value-to-zero normalization process and a whitening process on the −10 box-associated training data matrix $X_{-10}$ (see FIG. 14) generated by the −10 box-associated training data matrix-generating means 22D. Next, by using $V=D^{-1/2}G^T$, a matrix calculation process for multiplying the V with each of the column vectors $X_{-10}$ (j) (j=1 to 116) of the $X_{-10}$ and the obtained $VX_{-10}$ (j) is newly set to the $X_{-10}$ (j) (j=1 to 116), so that the pre-processed −10 box-associated training data matrix $X_{-10}$ is generated. Similar to the case of the −35 box, the processes based on a covariance matrix using nonlinear transformation of the $X_{-10}$ may be performed. Namely, the $X_{-10}$ (j) may be subjected to nonlinear transformation and, after that, the transformed $X_{-10}$ (j) may be set to a new $X_{-10}$ (j).

Next, as shown in FIG. 15, the −10 box-associated analyzing means 22E performs an independent component analysis (ICA) by using the pre-processed −10 box-associated training data matrix $X_{-10}$ and satisfies $Y_{-10}=W_{-10}X_{-10}$. In addition, the −10 box-associated analyzing means 22E obtains the −10 box-associated separation matrix $W_{-10}$ in which elements of $Y_{-10}$ are independent of each other and the −10 box-associated separation data matrix $Y_{-10}$ and stores the obtained $W_{-10}$ and $Y_{-10}$ in the −10 box-associated separation matrix storage means 52 and the −10 box-associated separation data matrix storage means 53 (see FIG. 1), respectively (Step S407 of FIG. 11). Here, the independent component analysis (ICA) is a process for obtaining a −10 box-associated separation matrix $W_{-10}$ in which the column vectors $Y_{-10}$ (j) of the $Y_{-10}$ are independent of each other. In addition, similarly to an independent component analysis (ICA) (Step S506 of FIG. 16) for obtaining the later-described promoter-associated separation matrix $W_{prom}$ and promoter-associated separation data matrix $Y_{prom}$, any kind of independent component analysis may be used. In addition, similarly to the case of obtaining the later-described promoter-associated separation matrix $W_{prom}$ and promoter-associated separation data matrix $Y_{prom}$, a principal component analysis (PCA) may be performed as a −10 box-associated analysis process, and dimension reduction may be performed. In addition, although the independent component analysis (ICA) for solving a linearity problem by using the aforementioned nonlinear transformation of the $X_{-10}$ as an input may be referred to as a nonlinear ICA, such a nonlinear independent component analysis (ICA) can be included in the present invention. In addition, although an independent component analysis (ICA) for solving a linearity problem by using training data obtained by linear or nonlinear transformation as an input may also be referred to as a nonlinear ICA, if objects of the present invention can be achieved by such a ICA, approximation and linearization processes thereof can be included in the present invention.

(Promoter Training)

Referring to FIG. 16, firstly, the promoter alignment processing means 23A performs an alignment process for equalizing lengths of Np (106) known promoters to a constant length (in this case, sequence length: 65 mer) by inserting gaps (for example, indicated by a symbol "-"), that is, a process shown from the upper portion to the lower portion of FIG. 5 (Step S501). Although the alignment process may be performed according to a pre-defined rule, the alignment process can be performed according to a rule similar to that of an alignment process for a promoter candidate segment selected from test segments in a test step, and thus, detailed description thereof is made later (see FIG. 38). Since all the types of the Np (106) promoters are different, unlike the cases of the −35 boxes or the −10 boxes, the same promoters do not exist, a process for removing overlap is not performed.

Subsequently, the promoter symbol-frequency table-generating means 23B obtains symbol frequencies of the symbols A, T, G, C, and gap "-" at each sequence position in the whole pattern by using the Np (106) known promoters equalized to a constant length by the promoter alignment processing means 23A, generates a promoter symbol-frequency table $T_{prom}$ (see FIG. 19) by corresponding the symbol frequencies to the sequence positions and symbols in the whole pattern, and stores the generated $T_{prom}$ in the promoter symbol-frequency table storage means 61 (see FIG. 1) (Step S502 of FIG. 16).

Figures 19, 20:
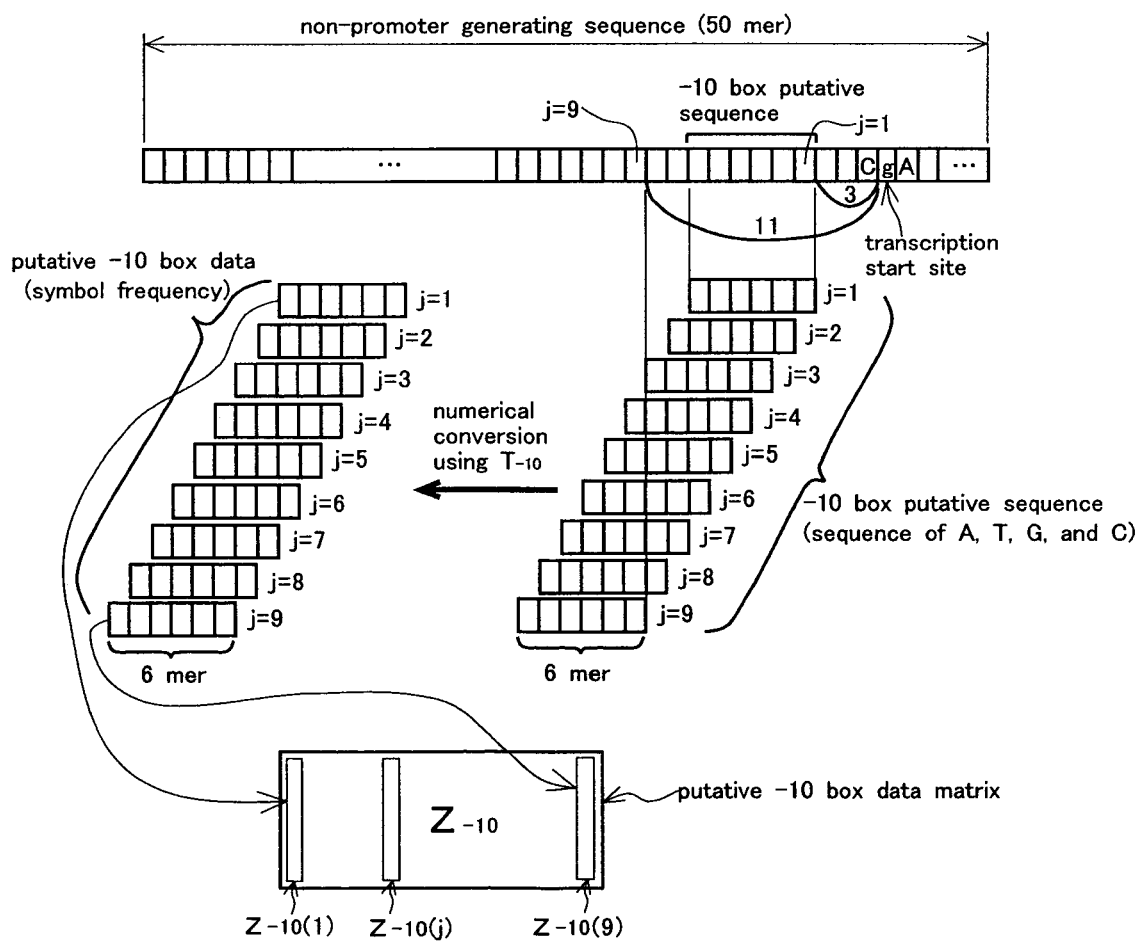
FIG. 19 is a first view for explaining a process in the promoter training according to the first embodiment.
FIG. 20 is a second view for explaining a process in the promoter training according to the first embodiment.

Next, the non-promoter-generating means 23C generates multiple types of non-promoters of which whole lengths are equalized to a constant length (in this case, sequence length: 65 mer) (Step S503 of FIG. 16). Namely, as shown in FIG. 20, the non-promoter-generating means 23C firstly prepares a non-promoter-generating sequence (for example, 50 mer) for generating the non-promoters (Step S50301 of FIG. 17). For example, each of the symbol frequencies of A and T is set to 0.3, each of the symbol frequencies of G and C is set to 0.2, and a plurality of the non-promoter-generating sequences are automatically generated at random.

Next, the non-promoter-generating means 23C selects a transcription start site in the non-promoter generating sequence (Step S50302 of FIG. 17). For example, the non-promoter-generating means 23C designates the A or G firstly appearing from the lower stream (the right side of FIG. 2) of the non-promoter-generating sequence as the transcription start site. In FIG. 20, the transcription start site is represented by a small letter.

Subsequently, as shown in FIG. 20, the non-promoter-generating means 23C selects a plurality of −10 box putative sequences (j=1 to 9) having the same lengths (6 mer) as that of the −10 box and having nucleotide positions shifted by 1 mer with reference to the designated transcription start site, so that an interval (corresponding to a spacer 10) between the −10 box putative sequences and the transcription start site is 3 to 11 mer (Step S50303 of FIG. 17).

Next, the non-promoter-generating means 23C converts to numerals a plurality (9) of the −10 box putative sequence according to the sequence positions and types of the symbols A, T, G, and C by using the −10 box symbol-frequency table $T_{-10}$ stored in the −10 box symbol-frequency table storage means 51 (see FIG. 1 and generates a plurality (9) of the putative −10 box data (Step S50304 of FIG. 17). In addition, a pre-process (a mean-value-to-zero normalization process or a whitening process) may not be performed on a plurality (9) of the putative −10 box data.

Next, as shown in FIG. 21, the non-promoter-generating means 23C performs a matrix calculation of multiplying the −10 box-associated separation matrix $W_{-10}$ with the putative −10 box data matrix $Z_{-10}$ in which a plurality (9) of the putative −10 box data are bound, that is, a calculation $Y_{-10can}=W_{-10}Z_{-10}$ and generates a putative −10 box data-associated separation data matrix $Y_{-10can}$ in which a plurality (9) of putative −10 box data-associated separation data are bound (Step S50305 of FIG. 17).

Subsequently, the non-promoter-generating means 23C obtains, among the generated plurality (9) of putative −10 box data-associated separation data $Y_{-10can}$ (j) (j=1 to 9), the $Y_{-10can}$ (j) of which summation q (i) of inner products of the $Y_{-10can}$ (j) with column vectors $Y_{-10}$ (k) of true data-corresponding portions of the −10 box-associated separation data matrix $Y_{-10}$ of FIG. 21 is maximized and selects the −10 box putative sequence (any one of a plurality (j=1 to 9) of the −10 box putative sequence of FIG. 20) corresponding to the obtained $Y_{-10can}$ (j) as the −10 box-corresponding sequences included in the non-promoter (Step S50306 of FIG. 17). Here, the true data-corresponding portion of the −10 box-associated separation data matrix $Y_{-10}$ is a portion corresponding to the portion $B_{-10}^T$ (58 columns) of the −10 box that is the true data in the column vectors of the −10 box-associated training data matrix $X_{-10}$ of FIG. 14.

Namely, the calculation $q(j)=\Sigma <Y_{-10can}$ (j), $Y_{-10}$ (k)> is performed. Here, j=1 to 9, and k=1 to 58. $\Sigma$ denotes summation over k=1 to 58, and $<\ldots,\ldots>$ denotes inner product. Next, $J_{-10}=\arg\{\max q(j)\}$ (j=1 to 9) is obtained, and the obtained $j_{-10}$ (any one of j=1 to 9) is designated as the start site (the lowest-stream site) of the −10 box-corresponding sequences included in the non-promoter. In addition, the $J_{-10}=1$ (j=1) is the start site of the −10 box-corresponding sequence of which interval (an interval corresponding to the spacer 10) between the transcription start site and the −10 box-corresponding sequence is 3 mer, and the $J_{-10}=9$ (j=9) is the start site of the −10 box-corresponding sequence of which interval between the transcription start site and the −10 box-corresponding sequence is 11 mer (see FIG. 20).

Next, as shown in FIG. 22, the non-promoter-generating means 23C selects a plurality of the −35 box putative sequences (j=1 to 7) having the same length (6 mer) as that of the −35 box and having nucleotide positions shifted by 1 mer with respect to the position of the selected −10 box-corresponding sequence so that an interval (an interval corresponding to the spacer 35) between each of the −35 box putative sequence and the −10 box-corresponding sequence is in a range of 15 mer to 21 mer. (Step S50307 of FIG. 17).

Subsequently, the non-promoter-generating means 23C converts to numerals a plurality (7) of the −35 box putative sequence according to the sequence positions and types of the symbols A, T, G, and C by using the −35 box symbol-frequency table $T_{-35}$ stored in the −35 box symbol-frequency table storage means 41 (see FIG. 1) to generate a plurality (7) of putative −35 box data (Step S50308 of FIG. 17). In addition, a pre-process (a mean-value-to-zero normalization process or a whitening process) may not be performed on a plurality (7) of the putative −35 box data.

Subsequently, as shown in FIG. 23, the non-promoter-generating means 23C performs a matrix calculation of multiplying the −35 box-associated separation matrix $W_{-35}$ with the putative −35 box data matrix $Z_{-35}$ in which a plurality (7) of the putative −35 box data are bound, that is, $Y_{-35can}=W_{-35}Z_{-35}$, and generates a putative −35 box data-associated separation data matrix $Y_{-35can}$ in which a plurality (7) putative −35 box data-associated separation data are bound (Step S50309 of FIG. 18).

Subsequently, the non-promoter-generating means 23C obtains, among the generated plurality (7) of putative −35 box data-associated separation data $Y_{-35can}$ Y (j) (j=1 to 7), the $Y_{-35can}$ (j) of which summation q (j) of inner products of the $Y_{-35can}$ (j) with column vectors $Y_{-35}$ (k) of true data-corresponding portions of the −35 box-associated separation data matrix $Y_{-35}$ of FIG. 23 is maximized and selects the −35 box putative sequence (any one of a plurality (j=1 to 7) of the −35 box putative sequence of FIG. 22) corresponding to the obtained $Y_{-35can}$ (j) as the −35 box-corresponding sequences included in the non-promoter (Step S50310 of FIG. 18). Here, the true data-corresponding portion of the −35 box-associated separation data matrix $Y_{-35}$ is a portion corresponding to the portion $B_{-35}^T$ (72 columns) of the −35 box that is the true data in the column vectors of the −35 box-associated training data matrix $X_{-35}$ of FIG. 8.

Namely, the calculation $q(j)=\Sigma <Y_{-35can}$ (j), $Y_{-35}$ (k)> is performed. Here, j=1 to 7, and k=1 to 72. $\Sigma$ denotes summation over k=1 to 72, and $<\ldots,\ldots>$ denotes inner product. Next, $J_{-35}=\arg\{\max q(j)\}$ (j=1 to 7) is obtained, and the obtained $j_{-35}$ (any one of j=1 to 7) is designated as the start site (the lowest-stream site) of the −35 box-corresponding sequences included in the non-promoter. In addition, the $J_{-35}=1$ (j=1) is the start site of the −35 box-corresponding sequence of which the interval (an interval corresponding to the spacer 35) between the −10 box-corresponding sequence and the −35 box-corresponding sequence is 15 mer, and the $J_{-35}=7$ (j=7) is the start site of the −35 box-corresponding sequence of which the interval between the −10 box-corresponding sequence and the −35 box-corresponding sequence is 21 mer (see FIG. 22).

Subsequently, the non-promoter-generating means 23C selects a non-promoter based on the selected −10 box-corresponding sequences, the selected −35 box-corresponding sequences, and the designated transcription start site (Step S50311 of FIG. 18).

Next, as shown in FIG. 24, the non-promoter alignment processing means performs an alignment process for equalizing the lengths of the non-promoters to a constant length (in this case, sequence length: 65 mer) by inserting the gaps while each of the −10 box-corresponding sequences and the −35 box-corresponding sequences selected by the non-promoter generating means 23C is maintained to be in a one-body state (Step S50312 of FIG. 18). Name, the lengths of the −10 box-corresponding sequences and the −35 box-corresponding sequences are maintained, and the sequence lengths of the spacers 10 and 35 are set to 11 mer and 21 mer, respectively. The alignment process is the same as the alignment process (see FIG. 38) performed in the test step, and thus, details thereof are described later.

Next, it is decided whether or not a degree of alignment of the aligned non-promoters at each sequence position (for instance, positions 1 to 65) in the whole pattern with respect to the known aligned training promoter is equal to or less than 25 nucleotides, and only the non-promoters having a degree of alignment equal to or less than 25 nucleotides are employed (Step S50313 of FIG. 18).

Subsequently, it is decided whether or not Np (for instance, 106) non-promoters are prepared (Step S50314 of FIG. 18), and if Np (106) non-promoters are not prepared, the process returns to Step S50301 of FIG. 17.

When the Np (106) non-promoters are prepared, as shown in FIG. 25, the promoter-associated numerical conversion means 23E converts to numerals the Np (106) known promoters in which the lengths of whole patterns are equalized to a constant length (in this case, sequence length: 65 mer) by the promoter alignment processing means 23A and the Np (106) non-promoters in which the lengths of whole patterns are equalized to a constant length (in this case, sequence length: 65 mer) by the non-promoter alignment processing means 23D according to the sequence positions and types of symbols of A, T, G, C, and gap (for example, "−") by using the promoter symbol-frequency table $T_{prom}$ stored in the promoter symbol-frequency table storage means 61 (see FIG. 1) (Step S504 of FIG. 16).

Next, as shown in FIG. 25, the promoter-associated training data matrix generating means 23F transposes the $B_{prom\ and\ the\ Cprom}$ obtained by the numerical conversion of the Np (106) promoters and the Np (106) non-promoters in the promoter-associated numerical conversion means 23E into $B_{prom}{}^T$ and $C_{prom}{}^T$, respectively, and binds the $B_{prom}{}^T$ and the $C_{prom}{}^T$ to generate a promoter-associated training data matrix $X_{prom}$ (see FIG. 25) (Step S505 of FIG. 16).

Subsequently, the promoter-associated analyzing means 23G performs pre-processes such a mean-value-to-zero normalization process and a whitening process on the promoter-associated training data matrix $X_{prom}$ (see FIG. 25) generated by the promoter-associated training data matrix-generating means 23F (similarly to FIG. 9). As shown in FIG. 26, the promoter-associated analyzing means 23G performs an independent component analysis (ICA) by using the pre-processed promoter-associated training data matrix $X_{prom}$ so as to obtain a promoter-associated separation matrix $W_{prom}$ and a promoter-associated separation data matrix $Y_{prom}$. The promoter-associated analyzing means 23G stores the obtained $W_{prom}$ and $Y_{prom}$ in the promoter-associated separation matrix storage means 62 (see FIG. 1) and the promoter-associated separation data matrix storage means 63 (see FIG. 26), respectively (Step S506 of FIG. 16). Alternatively, in the present invention, similarly to the case of the –35 box or the –10 box, a process based on a covariance matrix using nonlinear transformation of the $X_{prom}$ may be performed. Namely, the $X_{prom}$ (j) (j=1 to 2Np; for instance) may be subjected to nonlinear transformation and, after that, the transformed $X_{prom}$ (j) may be set to a new $X_{prom}$ (j). In addition, although the independent component analysis (ICA) for solving a linearity problem by using the aforementioned nonlinear transformation of the $X_{prom}$ as an input may be referred to as a nonlinear ICA, such a nonlinear independent component analysis (ICA) can be included in the present invention. In addition, although an independent component analysis (ICA) for solving a linearity problem by using training data obtained by linear or nonlinear transformation as an input may also be referred to as a nonlinear ICA, if the objects of the present invention can be achieved by such a ICA, an approximation and linearization processes thereof can be included in the present invention.

In order to improve the recognition accuracy, the aforementioned independent component analysis (ICA) is preferably performed and, in order to reduce the processing time, the later-described principal component analysis (PCA) may be performed. In the promoter training, as shown in FIG. 9, the covariance matrix R is a 65×65 square matrix. In addition, a 65×65 diagonal matrix D (a matrix having zero elements except for diagonal elements) in which eigenvalues $\lambda_1$ to $\lambda_{65}$ of the covariance matrix R are arrayed diagonally in the descending order is obtained, and a 65×65 matrix G in which eigenvectors corresponding to the eigenvalues $\lambda_1$ to $\lambda_{65}$ are arrayed in columns is obtained. Next, when dimension reduction from 65 dimensions to n dimensions is performed, the 65×65 diagonal matrix D is transformed into an n×n diagonal matrix $D_n$ in which eigenvalues $\lambda_1$ to $\lambda_n$ of the covariance matrix R are arrayed diagonally in the descending order, and the 65×65 matrix G is transformed into a 65×n matrix G in which eigenvectors corresponding to the eigenvalues $\lambda_1$ to $\lambda_n$ are arrayed in columns. Therefore, $D_n^{-1/2}$ is an n×n matrix, and $G_n{}^T$ is an n×65 matrix, so that $V_n = D_n^{-1/2} G_n{}^T$. Accordingly, the $V_n$ is an n×65 matrix. If the n×65 matrix $V_n$ is selected as a promoter-associated separation matrix corresponding to the promoter-associated separation matrix $W_{prom}$ in the independent component analysis (ICA), in the test step, a matrix calculation process, $Y_{n,test} = V_n X_{test}$, for multiplying the n×65 promoter-associated separation matrix $V_n$ with the aligned 65-dimensional test data (column vector) or a 65×r (arbitrary number) test data matrix $X_{test}$ in which a plurality of the test data are combined is performed, so that the n-dimensional separation data (column vector) of an n×r (arbitrary number) separation data matrix $Y_{n,test}$ in which a plurality of separation data are bound is obtained. Next, it is decided whether or not to be a promoter by deciding at which side of a threshold exists a value of the feature decision element (the first element) of the n-dimensional separation data (column vector) or a value of the feature decision element (each element in the first row) of the n×r (arbitrary number) separation data matrix $Y_{n,test}$.

Alternatively, the reduced n-dimensional $V_n X_{prom}$ (if the $X_{prom}$ is a 65-dimensional column vector, the $V_n X_{prom}$ is an n-dimensional column vector; and if the $X_{prom}$ is a 65×r (arbitrary number) matrix, the $V_n X_{prom}$ is an n×r (arbitrary number) matrix) may be selected as a new training data (column vector) or a training data matrix $X_{n,prom}$, and the independent component analysis (ICA) may be performed by using the $X_{n,prom}$ to obtained the n×n promoter-associated separation matrix $W_{n,prom}$. In this case, in the test step, a matrix calculation process, $Y_{n,test} = W_{n,prom} X_{n,test}$, for multiplying the n×n promoter-associated separation matrix $W_{n,prom}$ with the n-dimensional test data (column vector) or the n×r (arbitrary number) test data matrix $X_n$,test is performed, so that the n-dimensional separation data (column vector) or the n×r (arbitrary number) separation data matrix $Y_{n,test}$ is obtained. Next, it is decided whether or not to be a promoter by deciding at which side of a threshold exists a value of the feature decision element (the first element) of the n-dimensional separation data (column vector) or a value of the feature decision element (each element in the first row) of the n×r (arbitrary number) separation data matrix $Y_{n,test}$. In addition, in the above-described case, a product $W_{n,prom} V_n$ of the n×n promoter-associated separation matrix $W_{n,prom}$ with the n×65 matrix $V_n$, that is, $W_{n,prom} D_n^{-1/2} G_n{}^T$ may be selected as the promoter-associated separation matrix.

The independent component analysis (ICA) may be implemented by using one of (1) a method of minimizing the average correlation data amount using a gradient scheme (2) a method of increasing non-Gaussianity using an immovable point scheme, and (3) a diagonalization method for a high-order statistic data amount.

In addition, as a result of the independent component analysis (ICA) or the principal component analysis (PCA), since plus/minus of a value of the feature decision element (each element of the first row) of the promoter-associated separation data matrix $Y_{prom}$ (or $Y_{n,prom}$; hereinafter, the same) may be inverted, a process for checking whether the value of the feature decision element of the promoter-associated separation data matrix $Y_{prom}$ is plus or minus is performed. The process of checking may be performed mechanically or manually. Next, in a case where the value of the feature decision element of the column vector of the $Y_{prom}$ corresponding to the column vector of a portion of the $B_{prom}{}^T$ that is true data in the promoter-associated training data matrix $X_{prom}$ is a plus value (for example, a value in the vicinity of 1), if the value of the feature decision element (each element of the first row) of the separation data matrix $Y_{test}$ (see FIG. 38) obtained in the test step becomes a plus value (for example, a value in the vicinity of 1), it may be decided to be a promoter. If the value thereof becomes a minus value (for example, a value in the vicinity of –1), it may be decided not to be a promoter. On the other hand, in a case where the value of the feature decision element of the column vector of the $Y_{prom}$ corresponding to the column vector of a portion of the $B_{prom}^T$ that is true data in the promoter-associated training data matrix $X_{prom}$ is a minus value (for example, a value in the vicinity of −1), if the value of the feature decision element (each element of the first row) of the separation data matrix $Y_{test}$ (see FIG. 38) obtained in the test step becomes a minus value (for example, a value in the vicinity of −1), it may be decided to be a promoter. If the value thereof becomes a plus value (for example, a value in the vicinity of 1), it may be decided not to be a promoter. Therefore, information required for the decision is set to the decision means 33. The process of setting may be performed mechanically or manually.

(Correlation Training)

Figures 28, 29:
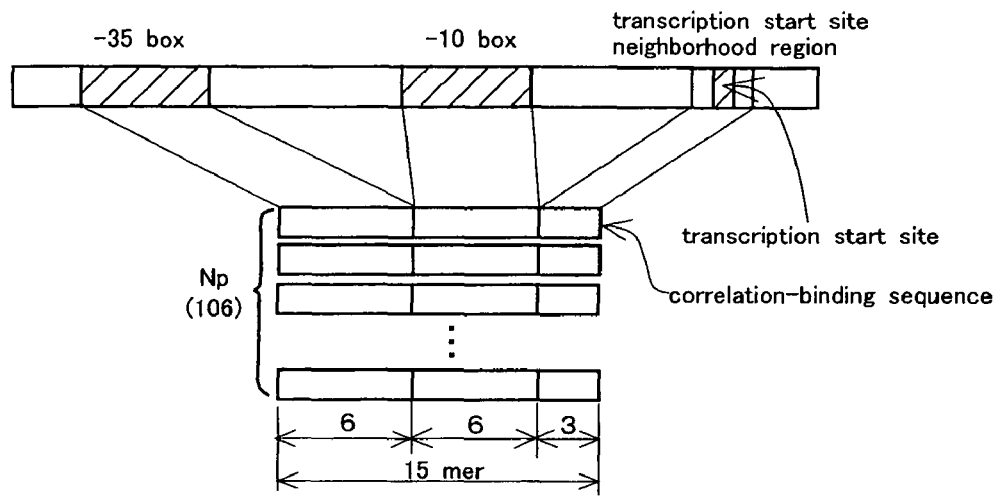
FIG. 28 is a first view for explaining a process in the correlation training according to the first embodiment.
FIG. 29 is a second view for explaining a process in the correlation training according to the first embodiment.

Referring to FIG. 27, firstly, as shown in FIG. 28, the correlation-binding sequence-generating means 24A binds the Np (106) known −35 boxes (6 mer) and the Np (106) known −10 boxes (6 mer) with the known transcription-start-site neighborhood sequence (in the embodiment, for example, 3 mer) to generate, for example, Np (106) 15-mer correlation-binding sequences (Step S601 of FIG. 27). In addition, the length of the transcription-start-site neighborhood sequences may be 4 mer, 5 mer, or the like.

Next, the correlation-decision symbol-frequency table-generating means 24B obtains symbol frequencies of the symbols A, T, G, and C at each sequence position in the correlation-binding sequences by using nucleotide information of the Np (106) correlation-binding sequences generated by the correlation-binding sequence-generating means 24A, generates a correlation-decision symbol-frequency table $T_{BBS}$ shown in FIG. 29 by corresponding the sequence positions and the symbols in the correlation-binding sequences, and stores the generated $T_{BBS}$ in the correlation-decision symbol-frequency table storage means 71 (see FIG. 1) (Step S601 of FIG. 27).

Subsequently, as shown in FIG. 30, the Np (106) correlation-binding sequences are amplified, for example, by ten times, and 10×Np (1060) correlation-binding sequences are arrayed at random. The amplification process is a process for amplifying the same data by a multiple, for example, ten times, which is called "bootstrapping process" in statistics.

Next, as shown in FIG. 30, the non-correlation-binding sequence-generating means 24C binds the 10×Np (1060) known −35 boxes (6 mer) and the 10×Np (1060) known −10 boxes (6 mer) with the 10×Np (1060) random sequences (for example, 3 mer) different from the known transcription-start-site neighborhood sequences to generate, for example, 10×Np (1060) 15-mer non-correlation-binding sequences (Step S603 of FIG. 27). Here, the 10×Np (1060) 3-mer random sequences are selected at random from a set of triplets constructed by excluding the known transcription-start-site neighborhood sequences (that is, one pattern as true data) for the known −35 boxes and the known −10 boxes and the symbolically unavailable ones from a combination of four symbols A, T, G, and C, that is, $4^3$ (=64) patterns. In addition, as shown in FIG. 30, since the 15-mer non-correlation-binding sequence can be obtained by replacing only the portion of the known 3-mer transcription-start-site neighborhood sequence of the correlation-binding sequence with the 3-mer random sequence, the remaining portions of the 6-mer −35 boxes and the 6-mer −10 boxes may be the same as those of the correlation-binding sequence.

Next, as shown in FIG. 30, the correlation-binding sequence numerical conversion means converts to numerals the 10×Np (1060) correlation-binding sequences and the 10×Np (1060) non-correlation-binding sequences according to the sequence positions in the boxes and the types of symbols A, T, G, and C by using the correlation-decision symbol-frequency table $T_{BBS}$ (see FIG. 29) stored in the correlation-decision symbol-frequency table storage means 71 (see FIG. 1) and generates matrix $B_{BBS}$ and matrix $C_{BBS}$ (Step S604 of FIG. 27).

Subsequently, as shown in FIG. 30, the correlation-decision training data matrix-generating means 24E transposes the $B_{BBS}$ and $C_{BBS}$ obtained by the correlation-binding sequence numerical conversion means 24D into $B_{BBS}^T$ and $C_{BBS}^T$, respectively, and binds the $B_{BBS}^T$ and $C_{BBS}^T$ to generate the correlation-decision training data matrix $X_{BBS}$ (Step S605 of FIG. 27).

In addition, when the correlation-decision training data matrix $X_{BBS}$ is generated, as shown with dotted lines in FIG. 30, $D_{BBS}^T$ constructed with, for example, 10×Np (1060) 15-mer random sequences (sequences different from the known −35 boxes or the known −10 boxes) may be bound to the $B_{BBS}^T$ and the $C_{BBS}^T$.

Subsequently, the correlation-decision analyzing means 24F performs pre-processes such a mean-value-to-zero normalization process and a whitening process on the correlation-decision training data matrix $X_{BBS}$ (see FIG. 30) generated by the correlation-decision training data matrix-generating means 24E and sets the obtained result to a new $X_{BBS}$ (similarly to FIG. 9). As shown in FIG. 31, the correlation-decision analyzing means 24F performs an independent component analysis (ICA) by using the pre-processed correlation-decision training data matrix $X_{BBS}$ so as to obtain a correlation-decision separation matrix $W_{BBS}$ and a correlation-decision separation data matrix $Y_{BBS}$. The correlation-decision analyzing means 24F stores the obtained $W_{BBS}$ and $Y_{BBS}$ in the correlation-decision separation matrix storage means 72 (see FIG. 1) and the correlation-decision separation data matrix storage means 73 (see FIG. 31), respectively (Step S606 of FIG. 27). The independent component analysis (ICA) is a process for obtaining the correlation-decision separation matrix $W_{BBS}$ in which the column vectors $Y_{BBS}$ (j) constituting the $Y_{BBS}$ are independent of each other. In addition, similarly to an independent component analysis (ICA) (Step S506 of FIG. 16) for obtaining the aforementioned promoter-associated separation matrix $W_{BBS}$ and promoter-associated separation data matrix $Y_{BBS}$, any kind of independent component analysis may be used. In addition, similarly to the case of obtaining the aforementioned promoter-associated separation matrix $W_{prom}$ and promoter-associated separation data matrix $Y_{prom}$, a principal component analysis (PCA) may be performed as a correlation-decision analysis process and dimension reduction may be performed. In addition, a nonlinear independent component analysis (ICA) or a nonlinear principal component analysis (PCA) may be performed.

In addition, as a result of the independent component analysis (ICA) or the principal component analysis (PCA), since the plus/minus of a value of the correlation-decision element (each element of the first row) of the correlation-decision separation data matrix $Y_{BBS}$ (or an n-dimension reduced $Y_{n,BBS}$; hereinafter, the same) may be inverted, a process for checking whether the value of the correlation-decision element of the correlation-decision separation data matrix $Y_{BBS}$ is plus or minus is performed. The process of checking may be performed mechanically or manually. Next, in a case where the value of the correlation-decision element of the column vector of the $Y_{BBS}$ corresponding to the column vector of the portion of the $B_{BBS}^T$ that is true data in the correlation-decision training data matrix $X_{BBS}$ is a plus value (for example, a value in the vicinity of 1), if the value of the correlation-decision element (each element of the first row) of the correlation-decision separation data matrix $Y_{BBS,test}$ (see FIG. 37) obtained in the test step becomes a plus value (for example, a value in the vicinity of 1), it may be decided that there is a correlation. If the value thereof becomes a minus value (for example, a value in the vicinity of −1), it may be decided that there is no correlation. On the other hand, in a case where the value of the correlation-decision element of the column vector of the $Y_{BBS}$ corresponding to the column vector of the portion of the $B_{BBS}{}^T$ that is true data in the correlation-decision training data matrix $X_{BBS}$ is a minus value (for example, a value in the vicinity of −1), if the value of the correlation-decision element (each element of the first row) of the correlation-decision separation data matrix $Y_{BBS,test}$ (see FIG. 37) obtained in the test step becomes a minus value (for example, a value in the vicinity of −1), it may be decided that there is a correlation. If the value thereof becomes a plus value (for example, a value in the vicinity of 1), it may be decided that there is no correlation. Therefore, information required for the correlation decision is set to the promoter candidate segment selection means 31G. The process of setting may be performed mechanically or manually.

The processes of the training steps are completed (Step S7 of FIG. 3). Next, the processes of the test step are performed.

<Test Step>

Referring to FIG. 32, firstly, a computer constituting the promoter recognition system 10 is powered on to drive programs and start a promoter recognition process (Step S11), and test segments is extracted from to-be-decided DNA sequence or DNA segment (Step S12). If test segments previously extracted from the to-be-decided DNA sequence or DNA segment are prepared, the cutting process may not be performed.

A length of the cut test segment is designed to be larger than the length of the longest promoter in multiple types of the known similar promoters. As shown in FIG. 36, the test segments are extracted from the DNA sequence or the DNA segment so that the test segments are overlapped by at least the length of the longest promoter and sequentially shifted. In addition, since a new similar promoter (a newly to-be-found promoter) may be longer than the longest promoter, a newly longest promoter longer than the former longest promoter is defined, and the length of the cut test segment is preferably designed to be slightly longer than the newly-defined longest promoter. Similarly, it is preferable that the overlapped length for the cutting is a length of the newly-defined longest promoter. If a plurality of the promoters exist among the cut test segments, there is difficulty in deciding one promoter that can be most probably recognized as the promoter in the one test segment. Therefore, it is preferable that the length of the test segment is designed to be smaller than two times the length of a known shortest promoter or smaller than two times the length of a newly-defined shortest promoter. For example, in case of a known *Escherichia coli* promoter disclosed in Non-Patent Document 1, since the length of a known promoter is in a range of 31 mer to 45 mer, the length of a test segment is equal to or more than 45 mer and less than 62 (31×2) mer, that is, in a range of 45 mer to 61 mer. In addition, in terms of correlation decision, all the 3 mer of the transcription-start-site neighborhood sequence (that is, 1 transcription start site +2 mer downstream thereof) are included, so that the length of the promoter required for the process is in a range of 32 mer to 46 mer. Therefore, the length of the test segment is equal to or more than 46 mer and less than 64 (32×2) mer, that is, in a range of 46 mer to 63 mer. In addition, by taking into consideration the newly-defined longest promoter, a lower bound of the length of the test segment is increased and, by taking into consideration the newly-defined shortest promoter, an upper bound of the length of the test segment is decreased. For description of the embodiment, the length of the test segment is designed to be 50 mer.

Next, a promoter candidate segment is selected from the test segments (50 mer) (Step S13). At this time, as shown by the two-dotted dashed lines, the transcription start sites are set to be shifted by 1 mer and a plurality of the promoter candidate segments may be selected from one test segment. Detailed description thereof is as follows.

Firstly, as shown in FIG. 33, the putative −10 box data-generating means 31B selects a transcription start site from the test segment (Step S1301). At this time, only one transcription start site may be selected from one test segment, for example, by selecting the A or G firstly appearing from the lower stream (the right side of FIG. 36). However, in terms of improvement of the recognition accuracy, it is preferable that a plurality of transcription start sites are selected from one test segment by repeatedly performing the below-described process Steps S1302 and S1312. Now, this case is described.

In addition, when the transcription start site is selected in the Step S1301 and the later-described Step S1312, the putative −10 box data generating means 31B decides whether or not the transcription-start-site neighborhood sequence is an unavailable sequence. If the transcription-start-site neighborhood sequence is an unavailable sequence, a process for excluding the transcription start site may be performed. For the process, all the available ones of the transcription-start-site neighborhood sequences may be stored in a memory (not shown).

Next, as shown in FIG. 36, the putative −10 box data-generating means 31B selects a plurality (9) of the −10 box putative sequences having the same length (6 mer) as that of the −10 box and having nucleotide positions shifted by 1 mer with respect to the selected transcription start site so that an interval (an interval corresponding to the spacer 10) between the transcription start site and each of the −10 box putative sequences is in a range of 3 mer to 11 mer (Step S1302 of FIG. 33).

Subsequently, as shown in FIG. 36, the putative −10 box data-generating means 31B converts to numerals a plurality (9) of the −10 box putative sequences according to the sequence positions and types of the symbols A, T, G, and C by using the −10 box symbol-frequency table $T_{-10}$ stored in the −10 box symbol-frequency table storage means 51 (see FIG. 1) to generate a plurality (9) of putative −10 box data (Step S1303 of FIG. 33).

Subsequently, similarly to FIG. 21, the putative −10 box data-associated separation data-generating means 31D performs a matrix calculation of multiplying the −10 box-associated separation matrix $W_{-10}$ stored in the −10 box-associated separation matrix storage means 52 (see FIG. 1) with the putative −10 box data matrix $Z_{-10}$ in which a plurality (9) of the putative −10 box data generated by the putative −10 box data-generating means 31B are bound, that is, $Y_{-10can} = W_{-10}Z_{-10}$, and generates a putative −10 box data-associated separation data matrix $Y_{-10can}$ in which a plurality (9) of the putative −10 box data-associated separation data are bound (Step S1304 of FIG. 33).

As shown in FIG. 21, the −10 box-corresponding sequences selection means 31F obtains, among a plurality (9) of the putative −10 box data-associated separation data (that is, the column vector $Y_{-10can}$ (j) (j=1 to 9) constituting the putative −10 box data-associated separation data matrix $Y_{-10can}$) generated by the putative −10 box data-associated separation data-generating means 31D, the putative −10 box data-associated separation data of which summation q(j) of the inner products of the putative −10 box data-associated separation data $Y_{-10can}(j)$ with the column vectors $Y_{-10}(k)$ of true data-corresponding portions of the −10 box-associated separation data matrix $Y_{-10}$ is maximized. The −10 box-corresponding sequences selection means 31F selects a −10 box putative sequence (similarly to FIG. 20, any one of a plurality (j=1 to 9) of the −10 box putative sequences) corresponding to the obtained putative −10 box data-associated separation data as a −10 box-corresponding sequence (Step S1305 of FIG. 33).

Namely, the calculation $q(j)=\Sigma<Y_{-10can}(j), Y_{-10}(k)>$ is performed. Here, j=1 to 9, and k=1 to 58. Σ denotes a summation over k=1 to 58, and < ..., ... > denotes an inner product. Next, $J_{-10}=\arg\{\max q(j)\}$ (j=1 to 9) is obtained, and the obtained $j_{-10}$ (any one of j=1 to 9) is designated as the start site (the lowest-stream site) of the −10 box-corresponding sequences included in the promoter candidate segment. In addition, the $J_{-10}=1$ (j=1) is the start site of the −10 box-corresponding sequence of which the interval (an interval corresponding to the spacer 10) between the transcription start site and the −10 box-corresponding sequence is 3 mer, and the $J_{-10}=9$ (j=9) is the start site of the −10 box-corresponding sequence of which the interval between the transcription start site and the −10 box-corresponding sequence is 11 mer (similarly to FIG. 20).

Subsequently, similarly to FIG. 22, the putative −35 box data-generating means 31A selects, among the test segment, a plurality (7) of the −35 box putative sequences having the same length (6 mer) as that of the −35 box and having nucleotide positions shifted by 1 mer with respect to the position of the −10 box-corresponding sequence selected by the −10 box-corresponding sequences selection means 31F so that an interval (an interval corresponding to the spacer 35) between the −10 box-corresponding sequence and each of the −35 box putative sequences in a range of 15 mer to 21 mer (Step S1306 of FIG. 33).

Next, as shown in FIG. 22, the putative −35 box data-generating means 31A converts to numerals a plurality (7) of the −35 box putative sequence according to the sequence positions and types of the symbols A, T, G, and C by using the −35 box symbol-frequency table $T_{-35}$ stored in the −35 box symbol-frequency table storage means 41 (see FIG. 1) to generate a plurality (7) of putative −35 box data (Step S1307 of FIG. 33).

Subsequently, similarly to FIG. 23, the putative extracted data-generating means for −35 boxes 31C performs a matrix calculation of multiplying the −35 box-associated separation matrix $W_{-35}$ stored in the −35 box-associated separation matrix storage means 42 (see FIG. 1) with the putative −35 box data matrix $Z_{-35}$ in which a plurality (7) of the putative −35 box data generated by the putative −35 box data-generating means 31A are bound, that is, $Y_{-35can}=W_{-35}Z_{-35}$, and generates a putative −35 box data-associated separation data matrix $Y_{-35can}$ in which a plurality (7) of the putative −35 box data-associated separation data are bound (Step S1308 of FIG. 34).

As shown in FIG. 23, the −35 box-corresponding sequences selection means 31E obtains, among a plurality (7) of the putative −35 box data-associated separation data (that is, the column vector $Y_{-35can}(j)$ (j=1 to 7; for instance) constituting the putative −35 box data-associated separation data matrix $Y_{-35can}$) generated by the putative extracted data-generating means for −35 boxes 31C, the putative −35 box data-associated separation data of which the summation q(j) of the inner products of the putative −35 box data-associated separation data $Y_{-35can}(j)$ with the column vectors $Y_{-35}(k)$ of the true data-corresponding portions of the −35 box-associated separation data matrix $Y_{-35}$ is maximized. The −35 box-corresponding sequences selection means 31E selects a −35 box putative sequence (similarly to FIG. 22, any one of a plurality (j=1 to 7) of the −35 box putative sequences) corresponding to the obtained putative −35 box data-associated separation data as a −35 box-corresponding sequence (Step S1309 of FIG. 34).

Namely, the calculation $q(j)=\Sigma<Y_{-35can}(j), Y_{-35}(k)>$ is performed. Here, j=1 to 7, and k=1 to 72. Σ denotes summation over k=1 to 72, and < ..., ... > denotes inner product. Next, $J_{-35}=\arg\{\max q(j)\}$ (j=1 to 7) is obtained, and the obtained $j_{-35}$ (any one of j=1 to 7) is designated as the start site (the lowest-stream site) of the −35 box-corresponding sequences included in the promoter candidate segment. In addition, the $J_{-35}=1$ (j=1) is the start site of the −35 box-corresponding sequence of which the interval (an interval corresponding to the spacer 35) between the −10 box-corresponding sequence and the −35 box-corresponding sequence is 15 mer, and the $J_{-35}=7$ (j=7) is the start site of the −35 box-corresponding sequence of which the interval between the −10 box-corresponding sequence and the −35 box-corresponding sequence is 21 mer (similarly to FIG. 22).

Next, as shown in FIG. 37, the promoter candidate segment selection means 31G selects a promoter candidate segment based on the −35 box-corresponding sequence selected by the −35 box-corresponding sequences selection means 31E and the −10 box-corresponding sequence selected by the −10 box-corresponding sequences selection means 31F, and the transcription start sites corresponding thereto (Step S1310 of FIG. 34). The promoter candidate segment selection means 31G decides whether or not there is a correlation of the −35 box-corresponding sequences and the −10 box-corresponding sequences to the transcription-start-site neighborhood sequences including the transcription start sites corresponding thereto, and if there is no correlation, does not perform a process for deciding a promoter candidate segment based on the −35 box-corresponding sequences, the −10 box-corresponding sequences, and the transcription start sites in the transcription-start-site neighborhood sequences. Namely, the sequences selected from the −35 box-corresponding sequences, the −10 box-corresponding sequences, the transcription start sites in the transcription-start-site neighborhood sequences are not used as a promoter candidate segment. Details thereof are as follows.

In FIG. 35, as shown in FIG. 37, the promoter candidate segment selection means 31G binds the −35 box-corresponding sequences, the −10 box-corresponding sequences, and the transcription-start-site neighborhood sequences including the transcription start sites corresponding thereto to generate correlation-decision sequences (Step S13101 of FIG. 35).

Next, as shown in FIG. 37, the promoter candidate segment selection means 31G converts to numerals the correlation-decision sequences according to the sequence positions and types of symbols A, T, G, and C by using the correlation-decision symbol-frequency table $T_{BBS}$ stored in the correlation-decision symbol-frequency table storage means 71 (see FIG. 1) to generate correlation-decision data (Step S13102 of FIG. 35).

Subsequently, as shown in FIG. 37, the promoter candidate segment selection means 31G performs a matrix calculation of multiplying the correlation-decision separation matrix $W_{BBS}$ stored in the correlation-decision separation matrix storage means 72 (see FIG. 1) with the correlation-decision data or a correlation-decision data matrix $X_{BBS,test}$ in which a plurality of the correlation-decision data are bound, that is, $Y_{BBS,test}=W_{BBS}X_{BBS,test}$ so that a correlation-decision separation process for obtaining correlation-decision separation data or a correlation-decision separation data matrix $Y_{BBS,test}$ in which a plurality of the correlation-decision separation data are bound is performed (Step S13103 of FIG. 35).

Next, the promoter candidate segment selection means 31G decides whether or not there is a correlation by deciding at which side of a predetermined correlation-decision threshold (for example, zero) exists a value of a correlation-decision element (for example, each element of the first row and, in case of a vector, a first element) selected according to a position of a matrix of feature elements (for example, elements of the first column) included in a predicted correlation-decision basis matrix $W_{ins}^{-1}$ among the correlation-decision separation data or the elements of the correlation-decision separation data matrix $Y_{BBS,test}$ obtained by the correlation-decision separation process. Only if there is decided to be a correlation, the promoter candidate segment selection means 31G decides the promoter candidate segment based on the −35 box-corresponding sequences, the −10 box-corresponding sequences, and the transcription start site of the transcription-start-site neighborhood sequences that have a correlation therein (Step S13104 of FIG. 35).

Next, it is determined whether or not the transcription start site can be shifted by 1 mer in the processing test segment (Step S1311 of FIG. 34). If the transcription start state is determined to be able to be shifted, the putative −10 box data generating means 31B sets the transcription start site to be shifted by 1 mer (Step S1312 of FIG. 34) and returns to the process of Step S1302 of FIG. 33. Next, until the transcription start site cannot be shifted, the processes of Steps S1302 of FIG. 33 to S1312 of FIG. 34 are repeatedly performed. On the other hand, in Step S1311 of FIG. 34, if the transcription start state is determined not able to be shifted, all the decision processes for a plurality of the promoter candidate segments in one test segment are terminated.

Next, in FIG. 32, the alignment processing means 31H performs an alignment process for equalizing the lengths of a plurality of the promoter candidate segments selected by the promoter candidate segment selection means 31G to a constant length (in this case, sequence length: 65 mer) by inserting the gaps "−" according to a predetermined rule (Step S14 of FIG. 32).

As shown in FIG. 38, the alignment process is performed according to the following rule. Memories for storing aligned promoter candidate segments (sequence length: 65 mer) are set to M(1) to M(65) from the upstream. Firstly, 14 mer upstream (the left side of the figure) of the −35 box-corresponding sequence are stored in the M(1) to M(14). If the nucleotides (mer) is less than 14 mer, gaps "−" corresponding to the insufficient portions are stored sequentially from M(1), and after that, the remaining nucleotides are stored.

Next, 6 mer of the −35 box-corresponding sequence are stored in the M(15) to M(20), and 5 mer downstream of the −35 box-corresponding sequence are stored in the M(21) to M(25). The 5 mer are a portion of the spacer 35.

Subsequently, since the sequence length of the after-alignment spacer 35 is equalized by 21 mer, gaps "−" corresponding to the number of before-21-alignment spacer 35 are stored in the M(26) to M(41), and after that, the remaining spacer 35 excluding the aforementioned 5 mer is stored.

Next, 6 mer of the −10 box-corresponding sequence are stored in the M(42) to M(47), and 3 mer downstream of the −10 box-corresponding sequence are stored in the M(48) to M(50). The 3 mer are a portion of the spacer 10.

Subsequently, since the sequence length of the after-alignment spacer 10 is equalized by 11 mer, gaps "−" corresponding to the number of before-11-alignment spacer 10 are stored in the M(51) to M(58), and after that, the remaining spacer 10 excluding the aforementioned 3 mer is stored.

Next, the transcription start site is stored in the M (59), and 6 mer at the lower stream of the transcription start site are stored in the M (60) to M (65). If the nucleotide length (mer) is less than 6 mer, gaps "−" corresponding to the insufficient portions are stored in the last memories.

The above-described alignment rule is the same as that of the aforementioned Non-Patent Document 1. However, the present invention is not limited to the alignment rule. In summary, a rule is defined, and sequences corresponding to partial patterns such as −35 boxes and −10 boxes may be arrayed at the same positions or substantially the same positions. Therefore, the sequence length of the after-alignment sequences is not limited to 65. For example, the sequence length may be 70, 75, 80, or the like.

Next, as shown in FIG. 38, the promoter candidate segment numerical conversion means 31J converts to numerals the promoter candidate segments aligned by the alignment processing means 31H according to the sequence positions and types of symbols of A, T, G, C, and gap "−" by using the promoter symbol-frequency table $T_{prom}$ (see FIG. 19) stored in the promoter symbol-frequency table storage means 61 (see FIG. 1) and generates the test data (Step S15 of FIG. 32).

Subsequently, the separation processing means 32 performs a pre-process step by using the average value (the average value obtained in the mean-value-to-zero normalization process) and the $V=D^{-1/2}G^T$ (the matrix V obtained by the whitening process) which are calculated in the aforementioned promoter training (Step S506 of FIG. 16) and stored in a memory (not shown). Namely, a matrix calculation for multiplying the test data (column vector) generated by the test data-generating means 31 or the column vector $X_{test}(j)$ of the test data matrix $X_{test}$ in which a plurality of the test data are bound with the V is performed, the obtained $VX_{test}(j)$ is set to a new $X_{test}(j)$, and the pre-processed test data (column vector) or the test data matrix $X_{test}$ is generated. Next, as shown in FIG. 38, the separation processing means 32 performs a matrix calculation of multiplying the promoter-associated separation matrix $W_{prom}$ stored in the promoter-associated separation matrix storage means 62 (see FIG. 1) with the pre-processed test data (column vector) or the test data matrix $X_{test}$ in which a plurality of the test data are bound, that is, $Y_{test}=W_{prom}X_{test}$, so that a separation process of obtaining separation data or a separation data matrix $Y_{test}$ in which a plurality of the separation data are bound is performed (Step S16 of FIG. 32).

In a case where a plurality of the promoter candidate segments are selected from one test segment (see FIG. 36), the separation processing means 32 performs the separation process on each of the test data obtained from each of the promoter candidate segments, and obtains a plurality of the separation data or a separation data matrix $Y_{test}$ in which a plurality of the separation data are bound, for one test segment.

The decision means 33 decides whether or not one of multiple types of known promoters or a new promoter similar to the known promoters is included in a test segment by deciding at which side of a predetermined threshold (for example, zero) exists a value of a feature decision element (for example, as shown in FIG. 38, each element of the first row and, in case of a vector, a first element) selected according to a position in a matrix of feature elements (for example, elements of the first column) included in a predicted basis matrix $W_{prom}^{-1}$ among the separation data or the elements of the separation data matrix $Y_{test}$ (in which a plurality of separation data are bound) obtained by the separation processing means 32 (Step S17 of FIG. 32). For example, if a value of each element in the first row of the separation data matrix $Y_{test}$, that is, the first element of each column vector $Y_{test}(j)$ of the separation data matrix $Y_{test}$ is a plus value (practically, for example, a value in the vicinity of 1), the promoter candidate segment corresponding to the column vector $Y_{test}(j)$ is decided to be a promoter. On the other hand, if the value is a minus value (practically, for example, a value in the vicinity of −1), the promoter candidate segment is decided not to be a promoter. In addition, as described above, as a result of the independent component analysis (ICA) or the principal component analysis (PCA), the plus/minus may be inverted, and in this case, the opposite decision is made.

In a case where a plurality of promoter candidate segments are selected from one test segment (see FIG. 36), the decision means 33 decides at which side of a predetermined threshold (for example, zero) exists a value of a feature decision element (for example, each element of the first row and, in case of a vector, a first element) selected according to a position in a matrix of feature elements (for example, elements of the first column) included in a predicted basis matrix $W_{prom}^{-1}$ among a plurality of the separation data or the elements of the separation data matrix $Y_{test}$ in which a plurality of the separation data are bound, for one test segment obtained by the separation processing means 32, obtains a value of the feature decision element having the largest absolute value of differences to the threshold among the values of the feature decision elements having the value (for example, a plus value) indicating the promoter, and recognizes the promoter candidate segment corresponding to the test data designated with the value of the obtained feature decision element as one of the multiple types of known promoters or the new promoter similar to the known promoters. For example, when the values of the first elements of the column vectors $Y_{test}(j)$ of the separation data matrix $Y_{test}$ are 0.93, −1.07, 1.03, 0.96 . . . , a promoter candidate segment corresponding to test data designated with the largest value of 1.03 in the values of 1.03 and 0.96 that are the plus values indicating a promoter is recognized as a promoter.

The process of the test step is completed (Step S18 FIG. 32). In addition, as a result of the processes of the test step, when a new promoter is found, it is preferable that the training means 20 performs the training processes again by using the promoter as training data.

According to the first embodiment, the following effects can be obtained. Namely, the promoter recognition system 10 converts to numerals the nucleotide symbols A, T, G, and C and gaps "−" inserted by alignment process of the to-be-decided DNA sequence by using the symbol frequencies obtained according to the sequence positions and the types of the symbols and stored in the promoter symbol-frequency table $T_{prom}$ and decides whether or not the promoter exists in the DNA sequence by using the promoter-associated separation matrix $W_{prom}$ (the dimension-reduced $W_{n,prom}$; hereinafter, the same) obtained by performing the independent component analysis (ICA) or the principal component analysis (PCA), so that it is possible to further improve recognition accuracy for the promoter in comparison with a promoter analysis using a computer according to a conventional neural network method or expectation-maximization algorithm (EM algorithm). In addition, this method has an advantage in terms of processing time and cost in comparison with such a promoter analysis method using a biological experiment in a test tube or an X-ray analysis.

In addition, the partial-pattern symbol-frequency table $T_{-35}$ or $T_{-10}$ for each of the −35 boxes or −10 boxes that are the partial patterns included in the promoter is generated, the numerical conversion of the sequences is performed by using the table, and the sequences corresponding to the −35 boxes or the −10 boxes are found by using the partial-pattern separation matrix $W_{-35}$ (or a dimension-reduced $W_{n,-10}$; hereinafter, the same) or $W_{-10}$ (or dimension-reduced $W_{n,-10}$; hereinafter, the same) obtained by performing the independent component analysis (ICA) or the principal component analysis (PCA), so that there is a variation in positions of the −35 boxes or the −10 boxes in the promoter. Accordingly, even in such a situation that there is a variation in a whole length of the promoter, it is possible to recognize the promoter with a high accuracy.

In addition, as shown in FIGS. 21 and 23, since the summation q(j) of inner products is used to find the sequences corresponding to the −35 boxes or the −10 boxes, the more accurate −35 box-corresponding sequences or −10 box-corresponding sequences can be found, so that it is possible to recognize the promoter with a high accuracy.

In addition, in the test step, a plurality of the promoter candidate segments can be selected so as to be shifted by 1 mer in one test segment (see FIG. 36), and a process for deciding one sequence which is recognized as a promoter among a plurality of the promoter candidate segments is performed, so that it is possible to recognize the promoter with a higher accuracy under the assumption that the test segment is set to be at a suitable length.

In addition, in the test step, in order to decide the promoter candidate segment, the correlation-decision process for deciding a correlation between the transcription-start-site neighborhood sequences and the −35 box-corresponding sequences and −10 box-corresponding sequences is performed. If there is no correlation there, sequences decided based on the transcription start site among the −35 box-corresponding sequences, the −10 box-corresponding sequences, the transcription-start-site neighborhood sequence may be excluded from the promoter candidate segments. Therefore, it is possible to further improve the recognition accuracy for the promoter. In addition, if there is decided to be no correlation there, since the sequences are decided based on the transcription start site among the −35 box-corresponding sequences, the −10 box-corresponding sequences, the transcription-start-site neighborhood sequence are not employed as the promoter candidate segment, the test data for the sequences need not be generated, and the separation process of the separation processing means 32 and the decision process of the decision means 33 need not to be performed. Therefore, it is possible to reduce a processing time.

In addition, the correlation-decision process is performed by using the correlation-decision separation matrix $W_{BBS}$ obtained in a previous training step by the independent component analysis (ICA) or the principal component analysis (PCA), so that it is possible to improve the accuracy of the correlation decision.

<Experiment for Effects>

In order to examine the effects of the present invention, the following experiment is carried out. Methods and conditions of the experiment are based on those of the first embodiment.

Figure 39:
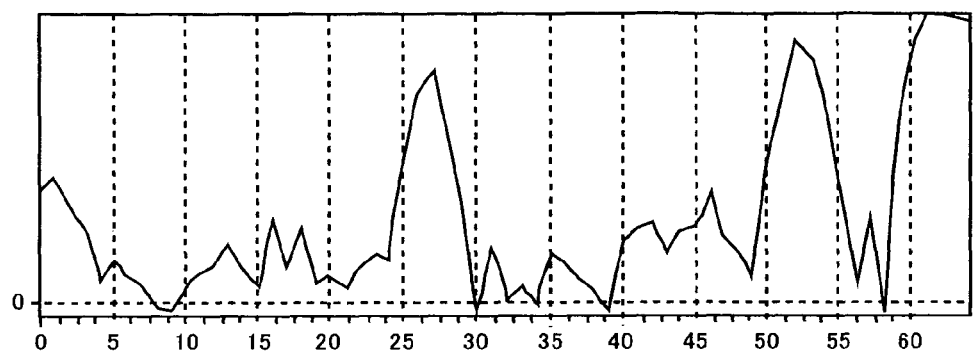
FIG. 39 is a graph illustrating values of elements of a first column of an inverse matrix $W_{prom}^{-1}$ of a promoter-associated separation matrix $W_{prom}$ in an experiment for effects (an experiment according to the first embodiment) according to the present invention.
Figure 40:
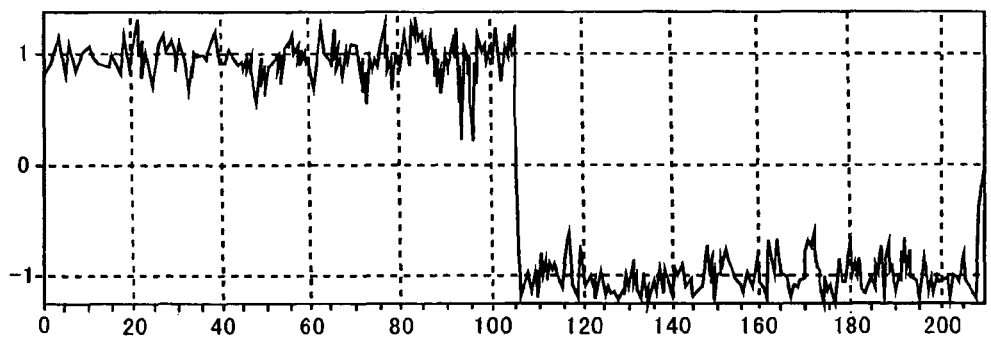
FIG. 40 is a graph illustrating the values of elements of a first row of an promoter-associated separation data matrix $Y_{prom}$ in the experiment for effects (the experiment according to the first embodiment) according to the present invention.
Figure 41:
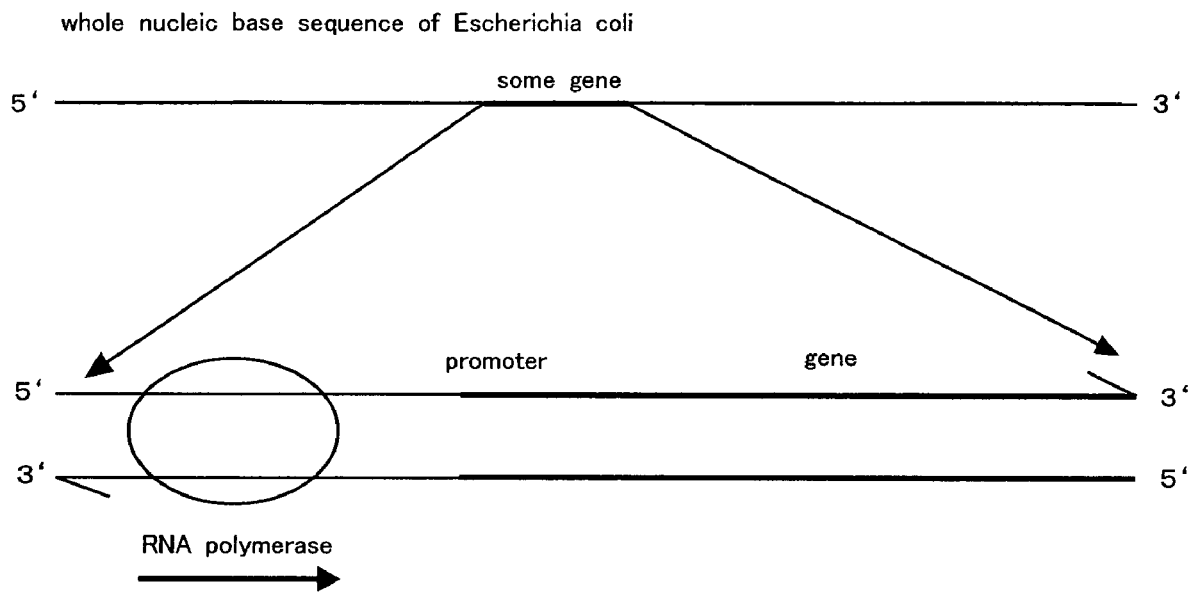
FIG. 41 is a view illustrating a state in which an RNA polymerase searches for an *Escherichia coli* promoter in an *Escherichia coli* nucleic base sequence.

Firstly, as described in the first embodiment, in the training step, the training is performed by using the 106 known *Escherichia coli* promoters disclosed in the aforementioned Non-Patent Document 1. FIG. 39 illustrates the values of the elements of the first column of the inverse matrix 65×65 $W_{prom}^{-1}$ of the 65×65 promoter-associated separation matrix $W_{prom}$ (see FIG. 26) obtained as a result of the training. The numerals of the horizontal axis correspond to row numbers (however, not 1 to 65 but 0 to 64). In the vertical axis, since only the inequality between values needs to be distinctly shown, the numerals are not shown. FIG. 40 illustrates the values of the elements of the first row of the 65×212 promoter-associated separation data matrix $Y_{prom}$ (see FIG. 26) obtained as a result of the training result. The numerals of the horizontal axis correspond to column numbers (however, not 1 to 212, but 0 to 211).

Referring to FIG. 39, it can be seen that bases unique to the promoter obtained by using the independent component analysis (ICA) are shown in the first column of the matrix predicting the inverse matrix $W_{prom}^{-1}$ of the promoter-associated separation matrix $W_{prom}$, that is, the promoter-associated basis matrix $A_{prom}$. The bases that represent the characteristics of the promoter most dominantly are shown in the first column of the $W_{prom}^{-1}$, but the bases that are shown in the other columns do not more dominantly represent the characteristic of the promoter than the aforementioned bases. Therefore, it can be seen that the elements of the first column of the $W_{prom}^{-1}$ correspond to the feature elements representing the features of the feature patterns according to the present invention. This can be understood as follows.

In general, a matrix constructed by collecting data (column vectors) from unknown independent information sources is denoted by S, a matrix constructed with mixed data (column vectors) observed in an overlapped state thereof is denoted by X, and a mixed matrix functioning as a filter for outputting X from input S, that is, a basis matrix A constructed with basis vectors is denoted by A. These matrixes have a relation of X=AS. On the other hand, when the matrix X constructed with the observed mixed data (column vectors) is given, an separation matrix for recovering before-mixture data, that is, original data is denoted by W, and a matrix constructed with separation data (column vector) obtained by separation is denoted by Y. These matrixes have a relation of Y=WX. The independent component analysis (ICA) is a process of obtaining the separation matrix W in which the elements are of Y (column vectors of the Y). The separation matrix W corresponds to a matrix obtained by predicting an inverse matrix of the basis matrix A. The inverse matrix $W^{-1}$ of the separation matrix W corresponds to a matrix obtained by predicting the basis matrix A. Therefore, the multiple types of known promoters are treated as a sequence having a noise in the natural features of the promoter. The promoter-associated training data matrix generated from the multiple types of known promoter is treated as observed mixed data (column vectors) $X_{prom}$. In this state, the independent component analysis (ICA) is performed, so that the $W_{prom}^{-1}$, that is, a matrix obtained by predicting the promoter-associated basis matrix $A_{prom}$ represents bases unique to the promoter. The bases are the first column of the $W_{prom}^{-1}$ shown in FIG. 39. Since $Y_{prom}=W_{prom}X_{prom}$ (see FIG. 26) $W_{prom}^{-1}Y_{prom}=X_{prom}$. In the matrix calculation, the elements of the first column of the $W_{prom}^{-1}$ are multiplied with the elements of the first row of the $Y_{prom}$. If the value of the elements of the first row of the $Y_{prom}$ become large, the contribution thereof to the first column of the $W_{prom}^{-1}$ becomes large. Therefore, it can be understood that the values of the element of the first row of the $Y_{prom}$ are the values of the feature decision elements according to the present invention.

Referring to FIG. 40, in the elements of the first row of the $Y_{prom}$, the values of the true data-corresponding portions $B_{prom}^{T}$ (see FIG. 25) in the promoter-associated training data matrix $X_{prom}$ are in the vicinity of 1, and the values of false data corresponding portions $C_{prom}^{T}$ (see FIG. 25) in the $X_{prom}$ are in the vicinity of −1. These results support the aforementioned description. In the test step, the values of the elements of the first row of the $Y_{test}$ (see FIG. 38) correspond to the values of the feature decision elements according to the present invention. It can be seen that the promoter can be decided based on the plus/minus of these values. In FIG. 40, the values in the vertical axis are in the vicinity of +1 or −1, but not limited to these values. When there is a difference between the portions corresponding to the promoter and the portions corresponding to the non-promoter in the elements of the first row of the $Y_{prom}$, a threshold can be defined based on the difference. The promoter can be decided based on the values of the elements of the first row of the $Y_{test}$ (see FIG. 38). Therefore, the threshold is not necessarily defined to be zero. In addition, as a result of the decision, when performing a soft decision for outputting the existence of the promoter, the values of the horizontal axis may be partitioned into several sections (For example, partitioning by 1, 0.6, 0.2, −0.2, −0.6, and −1). A section of 1 or more may be set to "a probability of the existence of a promoter is very high". A section of 0.6 to 1 may be set to "the probability of the existence of a promoter is high". A section of 0.2 to 0.6 may be set to "there is a probability of the existence of a promoter". A section of −0.2 to 0.2 may be set to "the existence of a promoter is obscure". In this manner, the different sections represent different outputs of the results of decisions.

Next, in the test step, 126 known *Escherichia coli* promoters disclosed in Non-Patent Document 1 are used as test data. The 126 *Escherichia coli* promoters are different from the 106 known *Escherichia coli* promoters used in the training step. According to Non-Patent Document 1, the gaps are already inserted into the 126 promoters. Therefore, the gaps are removed from the promoters, so that gap-less promoters having a reduced sequence length of 40 to 50 mer are obtained as test data (test segments).

In addition, 1000 random sequences having a sequence length of 50 mer are generated and prepared as the test data (test segments). The symbol frequencies of A and T are set to 0.3, and the symbol frequencies of G and C are set to 0.2. Therefore, a total of 1126 unaligned test data (test segments) are prepared.

Subsequently, with respect to the 1126 test data, the −10 box-corresponding sequences and the −35 box-corresponding sequences are selected by using the $W_{-10}$ and the $W_{-35}$. After that, an alignment process according to the method shown in FIG. 38 is performed to equalize the sequence lengths to 65 mer. In this case, the transcription start site is set to A or G that firstly appears from the lower stream. With respect to one test data (a test segment), only one transcription start site is selected (namely, in the experiment for effects, the slide setting for the transcription start site shown in FIG. 36 are not performed). In addition, the correlation decision of the −10 box-corresponding sequences and the −35 box-corresponding sequences to the transcription-start-site neighborhood sequence is not performed.

Next, the 1126 aligned promoter candidate segments is converted to numerals by using the promoter symbol-frequency table $T_{prom}$ to generate 1126 test data. After that, as shown in FIG. 38, a matrix calculation process for multiplying the promoter-associated separation matrix $W_{prom}$ with the test data matrix $X_{test}$ in which the 1126 test data are bound is performed to generate a 65×1126 promoter-associated separation data matrix $Y_{test}$.

Next, the threshold is set to zero, and plus/minus of the elements (feature decision elements) of the first row of the promoter-associated separation data matrix $Y_{test}$ is decided (namely, a hard decision is performed). As a result, among the 1126 test data, almost the values of the feature decision elements of the portions corresponding to the 126 known promoters are plus values, and almost the values of the feature decision elements of the portions corresponding to the 1000 random data (or non-promoters) are minus values. Therefore, a high recognition rate of 93.7% can be obtained. This shows that the effect of the present invention is very large. The recognition rate can be further improved from 93.7% by performing the slide setting process for the transcription start site and the correlation decision process.

Second Embodiment

Figure 42:
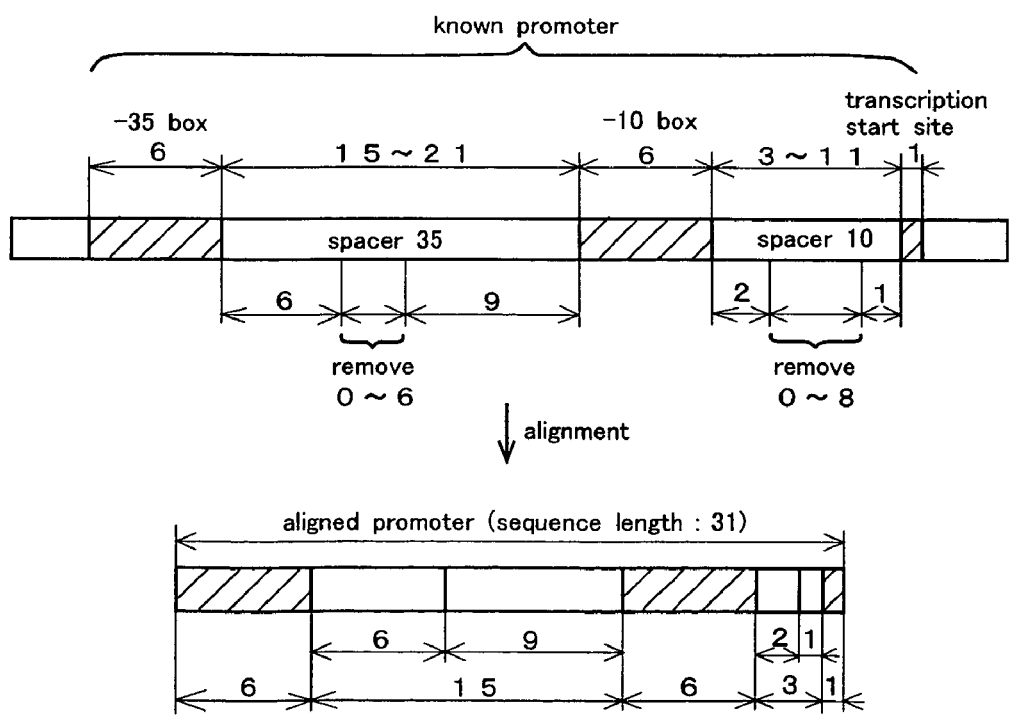
FIG. 42 is a view for explaining an alignment method according to a second embodiment of the present invention.
Figure 44:
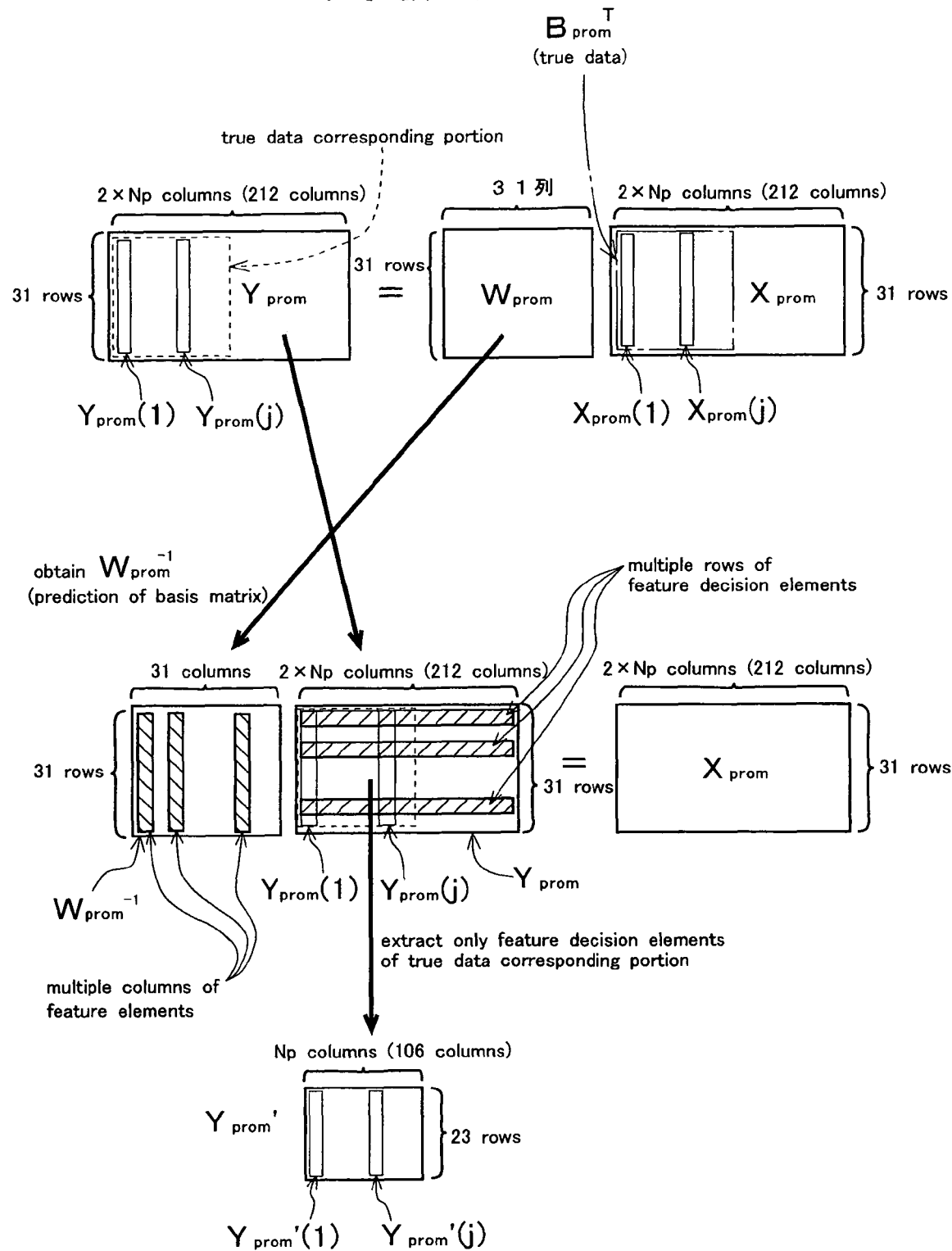
FIG. 44 is a view illustrating a relationship between a method of extracting feature elements in a basis matrix according to the second embodiment and feature decision elements of true data-corresponding portions among the promoter-associated separation data matrix $Y_{prom}$ used in a decision process of a test step.
Figure 47:
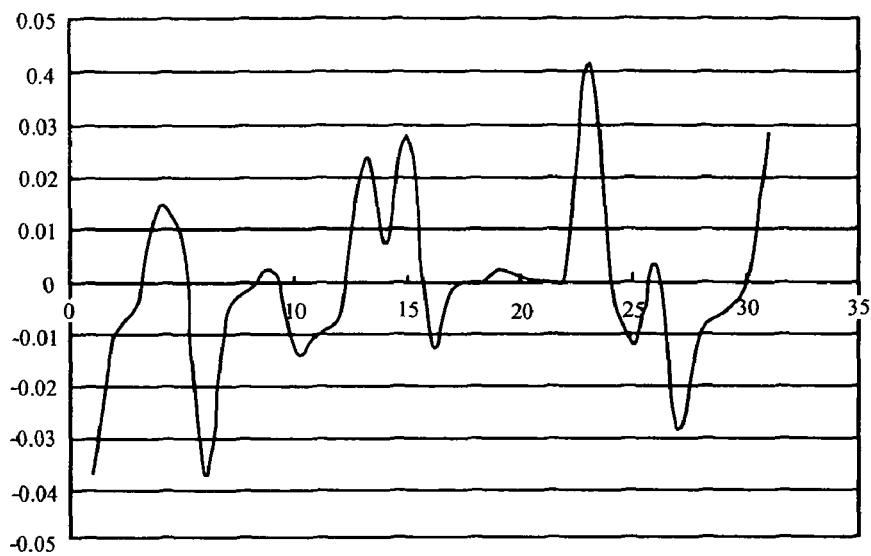
FIG. 47 is a graph illustrating values of elements of a 27-th column of the inverse matrix $W_{prom}^{-1}$ of the promoter-associated separation matrix $W_{prom}$ obtained in the process of the training step according to the second embodiment.
Figure 48:
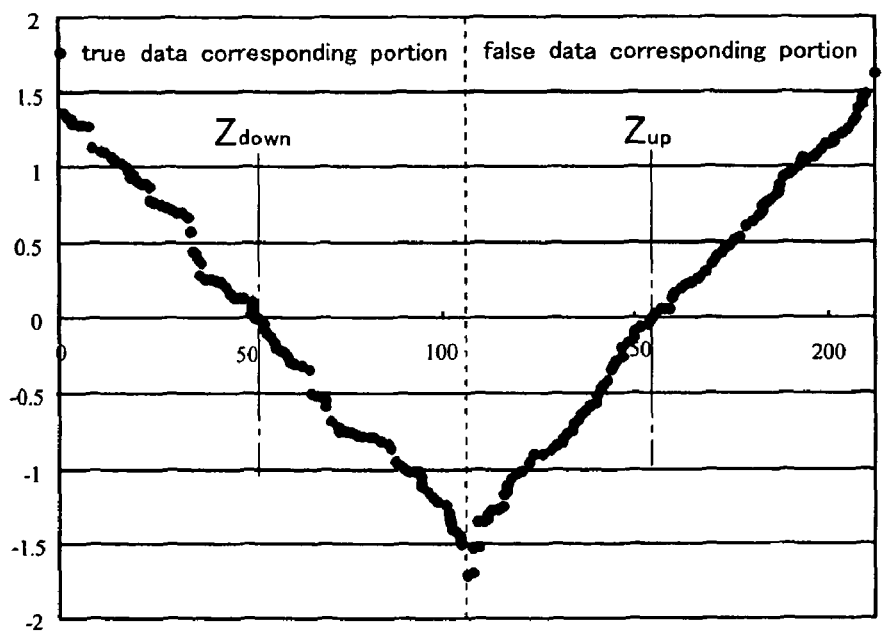
FIG. 48 is a graph illustrating values of elements of a 27-th row of the promoter-associated separation data matrix $Y_{prom}$ obtained in the process of the training step according to the second embodiment.
Figure 49:
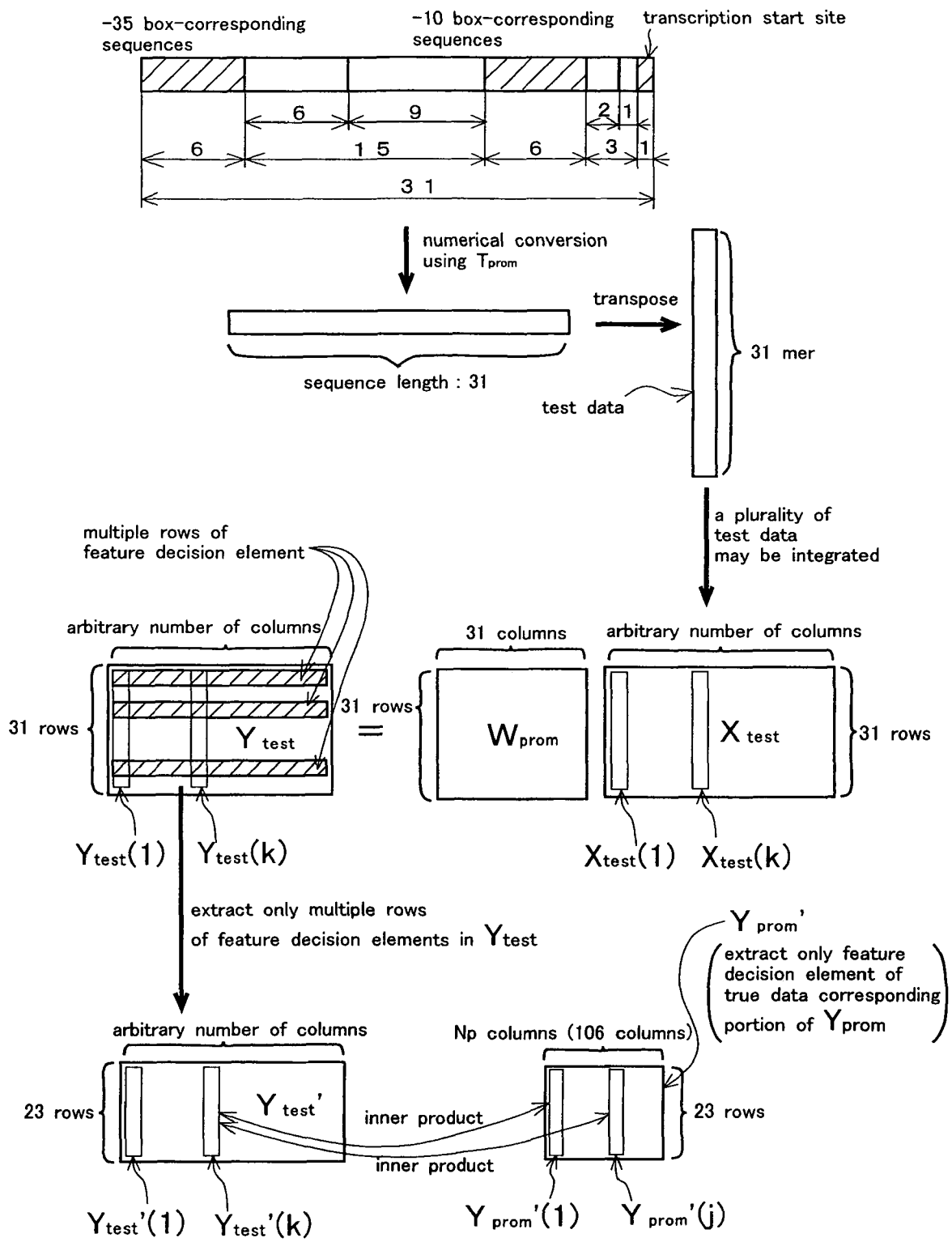
FIG. 49 is a view for explaining the process of the training step according to the second embodiment.

FIG. 42 is a view for explaining an alignment method according to a second embodiment of the present invention. FIG. 43 is a view illustrating a promoter symbol-frequency table $T_{prom}$ according to the second embodiment of the present invention. FIG. 44 is a view illustrating a relationship between a method of extracting feature elements in a basis matrix according to the second embodiment and feature decision elements of true data corresponding portions among the promoter-associated separation data matrix $Y_{prom}$ used in a decision process of a test step. FIGS. 45 and 46 illustrate values of elements of a first column of a basis matrix $W_{prom}^{-1}$ predicted from an inverse matrix of a promoter-associated separation matrix $W_{prom}$ and values of a first row of a promoter-associated separation data matrix $Y_{prom}$ obtained in a process of a training step according to the second embodiment, respectively, as employed examples. FIGS. 47 and 48 illustrate values of elements of a 27-th column of the $W_{prom}^{-1}$ and values of elements of a 27-th row of the $Y_{prom}$, respectively, as unemployed examples. FIG. 49 is a view for explaining the process of the training step according to the second embodiment.

In the second embodiment, in the alignment process, unlike the first embodiment where the gaps are inserted, a portion of the sequences constituting the spacer 35 and the spacer 10 is removed. In addition, in the decision process, unlike the first embodiment where only one (one row) feature decision element is used, a plurality (multiple rows) of the feature decision elements are used. However, other processes or constructions of the system according to the second embodiment are substantially the same as those of the first embodiment. Therefore, description of the same processes and constructions is omitted. The later description is made mainly on the different processes and constructions.

<Training Step>

A whole flow of the training steps is similar to that of the first embodiment shown in FIG. 3. Np known promoters (similarly to the first embodiment, for example, 106 *Escherichia coli* promoters) are prepared for training. The –35 box training, the –10 box training, the promoter training, and the correlation training are performed.

(–35 Box Training and –10 Box Training)

These processes are the same as those of the first embodiment. In the aforementioned random box-generating process in Step S304 of FIG. 4 and Step S404 of FIG. 11 according to the first embodiment, the random boxes are generated without non-uniformity in the symbol frequencies of A, T, G, and C so that each of the symbol frequencies of A, T, G, and C becomes 0.25, but the present invention is not limited thereto. For example, each of the symbol frequencies of A and T may be 0.3, and each of the symbol frequencies of G and C may be 0.2.

(Promoter Training)

Unlike the first embodiment, an alignment process using gap insertion is not performed. Therefore, the symbol frequency of the gaps is not included in the promoter symbol-frequency table $T_{prom}$. Since an alignment process is performed by removing a portion of the sequences constituting the spacer 35 and the spacer 10, the dimension of the promoter-associated separation matrix $W_{prom}$ or the promoter-associated separation data matrix $Y_{prom}$ is lower than that of the first embodiment. In the test step according to the first embodiment, the decision process is performed not by using the promoter-associated separation data matrix $Y_{prom}$ obtained in the training step but by using the feature decision elements of the one row (the first row) of the $Y_{test}$ obtained in the test step. However, in the second embodiment, the decision process is performed by using the feature decision elements of plural rows of the $Y_{test}$ obtained in the test step and the $Y_{prom}$ obtained in the training step. Now, detailed description thereof is made.

In the first embodiment, the promoter alignment processing means 23A performs the alignment process for equalizing the lengths of the multiple types of known promoters to a constant length (for example, sequence length: 65 mer) by inserting the gaps. However, in the second embodiment, as shown in FIG. 42, the promoter alignment processing means performs the alignment process for equalizing the lengths of the multiple types of known promoters to a constant length (for example, sequence length: 31 mer) by removing a portion of the sequences constituting the spacer 35 and the spacer 10.

As shown in FIG. 42, in the known promoter, the positions of the –35 box and the –10 box are known. Therefore, among the nucleic base sequences constituting the spacer 35, 6 mer in the vicinity of the –35 box (6 mer connected to the lower stream of the –35 box) and 9 mer in the vicinity of the –10 box (9 mer connected to the upstream of the –10 box) are used, and the sequences there are removed. Accordingly, since the sequence length of the spacer 35 of the 106 known *Escherichia coli* promoters is in a range of 15 mer to 21 mer, the sequence length of the sequences removed from the spacer 35 is in a range of 0 to 6 mer. Namely, in order to avoid insertion of gaps and reduce the number of removed sequences as small as possible, the sequence length is designed to be equalized to 15 mer, that is, the shortest sequence length of the spacer 35. Although the 6 mer in the vicinity of the –35 box and the 9 mer in the vicinity of the –10 box are used, the present invention is not limited thereto. For example, the 7 mer in the vicinity of the –35 box and the 8 mer in the vicinity of the –10 box may be used if a sum of sequence lengths is 15 mer. In addition, if the insertion of gaps can be avoided, the sequence length may be equalized to 14 mer or less.

Among the nucleic base sequences constituting the spacer 10, 2 mer in the vicinity of the –10 box (2 mer connected to the lower stream of the –10) and 1 mer in the vicinity of the transcription start site (1 mer connected to the upstream of the transcription start site) are used, and the sequences there are removed. Accordingly, since the sequence length of the spacer 10 of the 106 known *Escherichia coli* promoters is in a range of 3 mer to 11 mer, the sequence length of the sequences removed from the spacer 10 is in a range of 0 to 8 mer. Namely, in order to avoid the insertion of gaps and reduce the number of removed sequences as small as possible, the sequence length is designed to be equalized to 3 mer, that is, the shortest sequence length of the spacer 10. Although the 2 mer in the vicinity of the –10 box and the 1 mer in the vicinity of the transcription start site are used, the present invention is not limited thereto. For example, the 1 mer in the vicinity of the –10 box and the 2 mer in the vicinity of the transcription start site may be used if a sum of sequence lengths is 3 mer. In addition, if the insertion of gaps can be avoided, the sequence length may be equalized to 2 mer or less.

In the first embodiment, since the gaps are included in the multiple types of the known promoters of which the sequence lengths are equalized to a constant length (for example, sequence length: 65 mer) by the promoter alignment processing means 23A, the promoter symbol-frequency table generating means 23B adds the gaps to the symbols A, T, G, and C and obtains the symbol frequencies of the symbols including the gaps. However, in the second embodiment, since the gaps are not included in the multiple types of the known promoters of which the sequence lengths are equalized to a constant length (for example, sequence length: 31 mer), the promoter symbol-frequency table generating means obtains the symbol frequencies of the symbols A, T, G, and C excluding the gaps. Accordingly, in the first embodiment, the promoter symbol-frequency table $T_{prom}$ stored in the promoter symbol-frequency table storage means 61 (see FIG. 1) includes the symbol frequency of the gaps (see FIG. 19). However, in the second embodiment, as shown in FIG. 43, the promoter symbol-frequency table $T_{prom}$ stored in the promoter symbol-frequency table storage means does not include the symbol frequency of the gaps, so that it is possible to reduce an amount of the stored data. In addition, since the sequence length can be decreased from 65 mer to 31 mer, it is also possible to reduce an amount of the stored data.

In the first embodiment, the non-promoter-generating means 23C automatically generates a plurality of the non-promoter-generating sequences and selects, among a plurality of the non-promoter-generating sequences, the partial pattern-corresponding sequences (the −10 box-corresponding sequences and the −35 box-corresponding sequences) included in the non-promoter that is a non-feature pattern by using the partial-pattern separation matrix (the −10 box-associated separation matrix $W_{-10}$ and the −35 box-associated separation matrix $W_{-35}$) and the column vectors of the true data-corresponding portions of the partial-pattern separation data matrix (the −10 box-associated separation data matrix $Y_{-10}$ of FIG. 21 and the −35 box-associated separation data matrix $Y_{-35}$ of FIG. 23) (Steps S50305 and S50306 of FIG. 17 and Steps S50309 and S50310 of FIG. 18). In addition, the non-promoter-generating means 23C selects the non-promoter based on the partial pattern-corresponding sequences (the −10 box-corresponding sequences and the −35 box-corresponding sequences) in the selected regions (Step S50311 of FIG. 18). However, in the second embodiment, the non-promoter-generating means generates by not performing the decision process for the partial pattern-corresponding sequences (the −10 box-corresponding sequences and the −35 box-corresponding sequences) using the partial-pattern separation matrix (the −10 box-associated separation matrix $W_{-10}$ and the −35 box-associated separation matrix $W_{-35}$) or the partial-pattern separation data matrix (the −10 box-associated separation data matrix $Y_{-10}$ and the −35 box-associated separation data matrix $Y_{-35}$).

Firstly, in the second embodiment, each of the symbol frequencies of A and T is set to 0.3, and each of the symbol frequencies of G and C is set to 0.2. The 65-mer random sequences are generated, and homology scores are calculated. Based on the inequality of the calculated homology scores, sequences close to the promoter (sequences of which the homology score suitably exceeds a predetermined threshold) are excluded, so that the same number of random sequences as the number (for example, 106) of known promoters are prepared. Details of homology scores are disclosed in the aforementioned Non-Patent Document 4.

After an extended −35 box (extended −35 region) and an extended −10 box (extended −10 region) are defined, the homology scores can be obtained through Procedures 1 to 3. The extended −35 box is a sequence having a sequence length of 16 mer including the 6 mer of the −35 box, the 9 mer connected to the upstream of the −35 box, and the 1 mer connected to the lower stream of the −35 box. The extended −10 box is a sequence having a sequence length of 14 mer including the 6 mer of the −10 box, the 5 mer connected to the upstream of the −10 box, and the 3 mer connected to the lower stream of the −10 box.

In Procedure 1, similarly to the first embodiment, with respect to, for example, the 106 known promoters of which the sequence lengths are equalized to 65 mer by inserting the gaps, the symbol frequencies of the symbols A, T, G, and C at each of the sequence positions of the extended −35 box and the extended −10 box are obtained. The homology scores are obtained by dividing the symbol frequencies with a standard deviation (for example, $(101/4)^{1/2}$). In the standard deviation, the numerator "101" in the square root is changed from "106" since the 5 promoters having the gaps are excluded from the extended −35 box and the extended −10 box. The denominator "4" in the square root denotes four types of the symbols, that is, A, T, G, and C.

In Procedure 2, with respect to the sequence lengths of the spacers 35 of, for example, the 101 known promoters, excluding the 5 promoters having the gaps from the extended −35 box and the extended −10 box, the symbol frequencies at each of the sequence lengths of 15 mer to 21 mer are obtained (namely, the symbol frequencies of the spacers 35 having the sequence length of 15 mer, or 16, . . . , 21 mer are obtained). The homology scores are obtained by dividing the symbol frequencies with a standard deviation (for example, $(101/7)^{1/2}$). In the standard deviation, the denominator "7" in the square root denotes seven types of sequence lengths, that is, 15 mer to 21 mer.

In Procedure 3, the homology scores for each of the same number of the prepared random sequences as the number (106) of the known promoters are obtained by the Equation: (Homology Score)=100×{[(Sum of Base Pair Scores)+(Spacing Score)−(Baseline Score)]/[(Maximum Scores)−(Baseline Score)]}

Here, the sum of the base pair scores is obtained by converting to numerals the nucleotides of extended −35 boxes and extended −10 boxes in the random sequences to the scores obtained in Procedure 1 (that is, a score obtained by dividing each of the symbol frequencies of A, T, G, and C by a standard deviation) and summing these numerals.

The spacing score is obtained by converting to a numeral the sequence length of the spacer 35 in the random sequences based on the scores obtained in Procedure 2 (that is, a score obtained by dividing each of the symbol frequencies of each sequence length of the 15 to 21 nucleotides by a standard deviation).

The maximum score is obtained by summing the highest score (maximum score) in the scores of the sequence positions in the extended −35 box, the highest score (maximum score) in the scores of the sequence positions in the extended −10 box, and the sequence length of the spacer 35.

The baseline score is obtained by summing an average value of scores at each sequence position in the extended-35 box, an average value of scores at each sequence position in the extended −10 box, and the scores of the sequence of the spacer 35.

In Procedure 3, the positions of portions corresponding to the −35 box, the −10 box, and the transcription start site in the random sequence having 65 mer are selected by defining the 7-th mer shifted from the end of the lower stream as the transcription start site, disposing the 11-mer spacer 10, the 6-mer −10 box, the 21-mer spacer 35, and the 6-mer −35 box sequentially toward the upstream from the transcription start site, and the remaining 14 mer from the end of the upstream. Namely, the positions are selected to be the same as the portions of portions corresponding to the −35 box, the −10 box, and the transcription start site in the non-promoter (see FIG. 24) of which sequence lengths are equalized to a constant length (sequence length: 65 mer) by inserting the gaps according to the first embodiment. However, like the first embodiment, the positions may be selected by using the partial-pattern separation matrix (the −10 box-associated separation matrix $W_{-10}$ and the −35 box-associated separation matrix $W_{-35}$) or the partial-pattern separation data matrix (the −10 box-associated separation data matrix $Y_{-10}$ and the −35 box-associated separation data matrix $Y_{-35}$). The calculation of the homology scores is not limited to the sequence length of 65 mer. Accordingly, the sequence lengths of the prepared random sequences are not limited to the sequence length of 65 mer. In addition, in the calculation of the homology scores, the process of excluding the sequence close to the promoter may be omitted.

Next, the sequence lengths of the 106 random sequences having a sequence length of 65 mer obtained by excluding the sequences close to the promoter by performing the above-described calculation of homology scores are equalized to the sequence length of 31 mer based on the rule shown in FIG. 42 by the non-promoter alignment processing means according to the second embodiment. Therefore, in the second embodiment, the alignment process using the gap insertion in the non-promoter alignment processing means 23D according to the first embodiment is not performed.

In the first embodiment, the promoter-associated numerical conversion means 23E converts to numerals, for example, the 106 promoters and the 106 non-promoters of which the sequence lengths are equalized to a constant length (sequence length: 65 mer) by using the promoter symbol-frequency table $T_{prom}$ (see FIG. 25). In the second embodiment, the promoter-associated numerical conversion means also performs the same process. However, unlike the first embodiment shown in FIG. 19, as shown in FIG. 43, the promoter symbol-frequency table $T_{prom}$, in which there is no symbol frequency of the gaps and in which the sequence positions are in a range of 1 mer to 31 mer, is used.

In the first embodiment, the promoter-associated training data matrix-generating means 23F transposes the $B_{prom}$ and the $C_{prom}$ (see FIG. 25) obtained by the promoter-associated numerical conversion means 23E into the $B_{prom}^T$ and the $C_{prom}^T$ and binds the $B_{prom}^T$ and the $C_{prom}^T$ to generate the promoter-associated training data matrix $X_{prom}$ (see FIG. 25). In the second embodiment, the promoter-associated training data matrix generating means also performs the same process. In the first embodiment, as shown in FIG. 25, the $B_{prom}^T$ and the $C_{prom}^T$ are 65×106 matrixes, and the $X_{prom}$ is a 65×212 matrix. However, in the second embodiment, the $B_{prom}^T$ and the $C_{prom}^T$ are 31×106 matrixes, and the $X_{prom}$ is a 31×212 matrix (see FIG. 44).

In the first embodiment, promoter-associated analyzing means 23G performs pre-processes such as a mean-value-to-zero normalization process and a whitening process on the promoter-associated training data matrix $X_{prom}$ (see FIG. 25) (similarly to FIG. 9) and performs the independent component analysis (ICA) by using the pre-processed promoter-associated training data matrix $X_{prom}$ so as to obtain a promoter-associated separation matrix $W_{prom}$ and a promoter-associated separation data matrix $Y_{prom}$ (see FIG. 26). In the second embodiment, the promoter-associated analyzing means also performs the same processes. In the first embodiment, as shown in FIG. 26, the $W_{prom}$ is a 65×65 matrix, and the $Y_{prom}$ is a 65×212 matrix. However, in the second embodiment, as shown in FIG. 44, the $W_{prom}$ is a 31×31 matrix, and the $Y_{prom}$ is a 31×212 matrix.

In the first embodiment, although the $Y_{prom}$ is not used for the following processes in the test step, the $Y_{prom}$ is obtained and stored in the promoter-associated separation data matrix storage means 63 (see FIG. 26) so as to be used to decide whether the values of the feature decision elements (each element of the first row) of the separation data matrix $Y_{test}$ (see FIG. 38) obtained in the test step are plus or minus values. However, in the second embodiment, since the $Y_{prom}$ is used for the following decision process in the test step, the $Y_{prom}$ needs to be stored in the promoter-associated separation data matrix storage means. As described later, since the feature decision elements of true data-corresponding portions (portions corresponding to the $B_{prom}^T$) among the $Y_{prom}$ are used for the following decision process in the test step, only the decision elements of the true data-corresponding portions among the $Y_{prom}$ may be stored. In addition, in a case where the decision process is performed by using centroid vectors from the column vectors constructed with the values of the decision elements of true data corresponding portions among the $Y_{prom}$, the centroid vectors may be obtained and stored in advance.

(Selection of Feature Elements from Basis Matrix)

In the first embodiment, a basis representing the feature of the promoter exists in one column of the basis matrix. When only the one column becomes feature elements (for example, as shown in FIG. 39, the first column of the $W_{prom}^{-1}$ becomes the feature elements), a unique basis which can represent the feature of the promoter most dominantly is selected as the feature element. However, in the second embodiment, as shown in FIG. 44, bases representing the feature of the promoter exist in a plurality of columns of the basis matrix, and a plurality of the columns become the feature elements. In order to select the columns (bases) which become the feature elements, the inverse matrix $W_{prom}^{-1}$ of the promoter-associated separation matrix $W_{prom}$ is obtained, and the basis matrix is predicted. The values of the elements of the columns (bases) of the predicted basis matrix $W_{prom}^{-1}$ are shown as a graph, so that the column (basis) representing the feature of the promoter can be selected by using an examination with the naked eye. Although the selection process of the feature element may be performed by using an examination of the graph of the columns (bases) of the $W_{prom}^{-1}$ with the naked eye, the values of the elements of the rows of the promoter-associated separation data matrix $Y_{prom}$ may be analyzed in order to reduce an artificial determination as follows.

If the column (basis) representing the feature of the promoter is designed to be shown in one column of the $W_{prom}^{-1}$, in the values of the elements of the rows of the promoter-associated separation data matrix $Y_{prom}$, there is a difference between the portions corresponding to the $B_{prom}^T$ in which the promoter is bound (the true data-corresponding portions) and the portions corresponding to the $C_{prom}^T$ in which the non-promoter is bound (the false data-corresponding portions) (see FIG. 40). Therefore, by using the difference, the values of the elements of the rows of the promoter-associated separation data matrix $Y_{prom}$ are divided into the true data-corresponding portions and the false data-corresponding portions, and after that, the analysis is performed.

In the above analysis, the sequence order of the promoter in the $B_{prom}^T$ constituting the $X_{prom}$ and the sequence order of the non-promoter in the $C_{prom}^T$ constituting the $X_{prom}$ are not important. Therefore, the sequence order of the columns in the true data-corresponding portions in the promoter-associated separation data matrix $Y_{prom}$ (the portions corresponding to the $B_{prom}^T$) and the sequence order of the columns in the false data-corresponding portions (the portions corresponding to the $C_{prom}^T$) are not also important. Accordingly, in the rows of the $Y_{prom}$, the values of the elements of the rows are arrayed again according to the inequality thereof to generate a graph. Here, in the true data-corresponding portions of the $Y_{prom}$, the values are arrayed in the ascending order in a direction from the left side to the right side. In the false data corresponding portions of the $Y_{prom}$, the values may be arrayed in the descending order in a direction from the left side to the right side. In addition, when the graph for the rows of the $Y_{prom}$ is generated, if the graph of the column (basis) of the $W_{prom}^{-1}$ is a graph of the column of which the peak value (highest value irrespective of signs of plus and minus) is a plus value, the values of the elements constituting the rows of the corresponding $Y_{prom}$ are used to generate a graph. On the other hand, if the graph of the columns (bases) of the $W_{prom}^{-1}$ is a graph of the column of which the peak value is a minus value, the values obtained by multiplying the values of the elements constituting the rows of the corresponding $Y_{prom}$ with −1 are used to generate a graph.

For example, as shown in FIG. 45, in the graph of the first column of the $W_{prom}^{-1}$, a peak portion where the −10 box is considered to react can be examined with the naked eye. Since there is a portion where the −10 box reacts, the first column may be selected as the feature element in an artificial manner. On the other hand, as shown in FIG. 46, in the graph of the first row of the $Y_{prom}$ corresponding to the first column of the $W_{prom}^{-1}$, a large number of plus values exist in the true data-corresponding portion (the 106-th column), and a large number of minus values exists in the false data-corresponding portion (the 106-th column). In addition, there is a conspicuous difference in signs between the true data-corresponding portion and the false data-corresponding portion. Therefore, this state may be automatically decided by using a predetermined threshold, so that it can be decided that the first column of the $W_{prom}^{-1}$ is a feature element. In order words, it can be decided that the first row of the $Y_{prom}$ is a feature decision element.

As shown in FIG. 47, in the graph of the 27-th column of the $W_{prom}^{-1}$, a peak portion where any one of the −35 box, the −10 box, and the transcription start site is considered to react cannot be examined with the naked eye. Therefore, the 27-th column may not be selected as the feature element in the artificial manner. On the other hand, as shown in FIG. 48, in the graph of the 27-th row of the $Y_{prom}$ corresponding to the 27-th column of the $W_{prom}^{-1}$, there is no conspicuous difference in signs between the true data-corresponding portion (the 106-th column) and the false data-corresponding portion (the 106-th column). Therefore, this state may be automatically decided by using a predetermined threshold, so that it can be decided that the 27-th column of the $W_{prom}^{-1}$ is not a feature element. In order words, it can be decided that the 27-th row of the $Y_{prom}$ is a feature decision element. Other columns of the $W_{prom}^{-1}$ and other rows of the $Y_{prom}$ may be decided in the above-described manner.

The threshold used to decide whether or not the columns of the $W_{prom}^{-1}$ are the feature elements, that is, whether or not the rows of the $Y_{prom}$ are the feature decision elements, can be set by scrutinizing the zero-crossing in the graphs of the rows of the $Y_{prom}$ as follows.

In the true data-corresponding portions (Np=106 columns), the positions at which the values of the elements are changed from plus to minus are denoted by $Z_{down}$. In the false data-corresponding portions (Np=106 columns), the positions at which the values of the elements are changed from minus to plus are denoted by $Z_{up}$. If $Z_{down} > (1+\theta_{down}) \times Np/2$ and $Z_{up} > \{(1+\theta_{up}) \times Np/2\} + Np$, the corresponding row of the $Y_{prom}$ is selected as the feature decision element. It is decided that the corresponding column (basis) of the $W_{prom}^{-1}$ is the feature elements. In this case, the decision is made by using both of the true data-corresponding portions and the false data-corresponding portions. In order to select the basis representing the feature of the promoter, the $Z_{down}$ is set to be larger than the central position (Np/2) of the true data-corresponding portions if possible, and the $Z_{up}$ is set to be larger than the central position (Np/2+Np) of the false data-corresponding portion. Therefore, if the $\theta_{down}$ or the $\theta_p$ indicating the separation from the central position is set to a large value, the more strict selection condition is used, so that only the good bases can be selected. For example, if $\theta_{down}=\theta_{up}=0.1$, for the central position (Np/2=53) of the true data corresponding portions, $(1+\theta_{down}) \times Np/2=58$, so that the selection condition is $Z_{down}>58$. For the central position (Np/2+Np=159) of the false date corresponding portions, $\{(1+\theta_{up}) \times Np/2\}+Np=164$, so that the selection condition is $Z_{up}>164$.

As described above, even in a case where the selection conditions for both of the true data-corresponding portions and the false data-corresponding portion cannot be satisfied, if any one condition is satisfied, the bases may be selected. In this case, since the decision is made by using one of the selection conditions, the more strict selection condition needs to be set in comparison with the case where the decision is made by using both of the selection conditions. For example, as described above, although the conditions $Z_{down}>(1+\theta_{down}) \times Np/2$ and $Z_{up}>(1+\theta_{up}) \times$ or if $Z_{up}>\{(1+\theta_{up}^*) \times Np/2\}+Np$, the corresponding row of the $Y_{prom}$ may be selected as the feature decision element, and it may be decided that the corresponding column (bases) of the $W_{prom}^{-1}$ is the feature element. In this case, the value of the $\theta_{down}^*$ or the $\theta_{up}^*$ may be set to larger than the value of the $\theta_{down}$ or the $\theta_{up}$. For example, if $\theta_{down}^*=\theta_{up}^*=0.15$, for the central position (Np/2=53) of the true data-corresponding portions, $(1+\theta_{down}^*) \times Np/2=61$, so that the strict selection condition $Z_{down}>61$ is used. For the central position (Np/2+Np=159) of the false data-corresponding portion, $\{(1+\theta_{up}^*) \times Np/2\}+Np=167$, so that the strict selection condition $Z_{up}>167$ is used.

In such a manner, the value of the $\theta_{down}$ or the $\theta_{up}$ or the value of the $\theta_{down}^*$ or the $\theta_{up}^*$ is set. Next, it is decided whether or not the rows of the $Y_{prom}$ are the feature decision elements. Namely, it is decided whether or not the columns (bases) of the $W_{prom}^{-1}$ are the feature elements. Next, as shown in FIG. 44, only the feature decision elements of the true data-corresponding portions among the $Y_{prom}$ are extracted. The obtained feature decision elements are stored as $Y_{prom}'$ in the promoter-associated separation data matrix storage means. For example, if a total of 23 rows among the 31 rows of the $Y_{prom}$ are decided to be the feature decision elements, the $Y_{prom}'$ becomes a 23×Np (106) matrix. The $Y_{prom}'$ is used for the following decision process in the test step. In addition, the centroid vectors from the column vectors $Y_{prom}'(j)$ (j=1 to 106) constituting the $Y_{prom}'$ may be obtained and stored. The basis reduction by using $\theta_{down}$ and $\theta_{up}$ can be replaced by the PCA.

(Correlation Training)

In the second embodiment, correlation training similar to that of the first embodiment may be performed.

<Test Step>

In the first embodiment, in the process of the test step, the processing means 31A to 31G of the test data generating means 31 performs the decision process for the promoter candidate segments by selecting the partial pattern-corresponding sequences (the −10 box-corresponding sequences and the −35 box-corresponding sequences) by using the partial-pattern separation matrix (the −10 box-associated separation matrix $W_{-10}$ and the −35 box-associated separation matrix $W_{-35}$) or the partial-pattern separation data matrix (the −10 box-associated separation data matrix $Y_{-10}$ and the −35 box-associated separation data matrix $Y_{-35}$). In the second embodiment, the same processes are performed in the test step.

In the first embodiment, in the decision process for the promoter candidate segment, it is decided whether or not there is a correlation between the −10 box-corresponding sequences, the −35 box-corresponding sequences, and the transcription-start-site neighborhood sequence. If there is decided to be no correlation, the process for not employing the promoter candidate segment is performed (see step S1310 of FIG. 34). In the correlation-decision process, the correlation decision is performed by using the correlation-decision elements of only one row (see step S13104 of FIG. 35 and FIG. 37). In the second embodiment, the same correlation-decision process may be performed. Alternatively, the correlation decision may be performed by using correlation-decision elements of a plurality of the rows. In a case where the correlation decision is performed by using the correlation-decision elements of a plurality of the rows, for example, similarly to the later-described process of deciding the promoter, a process is performed to calculate a value indicating a similarity measure between the column vector constructed with the values of the correlation-decision elements of a plurality of the rows (in case of one correlation-decision data, one column vector) and the column vector constructed with the values of the correlation-decision elements of the true data corresponding portions (the portions corresponding to the $B_{BBS}{}^T$ of FIG. 30) of the correlation-decision separation data matrix $Y_{BBS}$ which is obtained together with the correlation-decision separation matrix $W_{BBS}$ (see FIG. 31) in the training step. For example, a value indicating the similarity measure to the set of the column vectors, more specifically, the inner product to the centroid vectors from the column vectors or equivalent values thereof is calculated. Next, by deciding at which side of a predetermined threshold exists by using the calculated similarity measure, it can be decided whether or not there is a correlation or how much the correlation is.

In the processes of the test step according to the first embodiment, the alignment processing means 31H of the test data-generating means 31 performs the alignment process of equalizing the sequence lengths of the promoter candidate segments selected from the test segment to a constant length (sequence length: 65 mer) by inserting the gaps. However, unlike the first embodiment, in the processes of the test step according to the second embodiment, the alignment process is performed to equalize the sequence lengths to a constant length (sequence length: 31 mer) by removing a portion of the sequences of the spacer 35 and a portion of the sequences of the spacer 10 according to the rule shown in FIG. 42.

In the first embodiment, the promoter candidate segment numerical conversion means 31J converts to numerals the aligned promoter candidate segment by using the promoter symbol-frequency table $T_{prom}$ (see FIG. 38). In the second embodiment, the promoter candidate segment numerical conversion means also performs the same process (see FIG. 49). However, unlike the first embodiment shown in FIG. 19, as shown in FIG. 43, the promoter symbol-frequency table $T_{prom}$ in which there is no symbol frequency of the gaps and in which sequence positions are in a range of 1 mer to 31 mer is used.

Next, in the first embodiment, the separation processing means 32 performs the pre-process on the test data (column vectors) generated by the test data-generating means 31 or the test data matrix $X_{test}$ in which a plurality of the test data are bound and, after that, performs the separation process by performing the matrix calculation of multiplying the promoter-associated separation matrix $W_{prom}$ with the pre-processed test data (column vectors) or the test data matrix $X_{test}$ in which a plurality of the test data are bound to obtain the separation data of the separation data matrix $Y_{test}$ in which a plurality of the separation data are bound (see FIG. 38). In the second embodiment, the separation processing means also performs the same processes (see FIG. 49). However, unlike the first embodiment where the promoter-associated separation matrix $W_{prom}$ is a 65×65 matrix, in the second embodiment, promoter-associated separation matrix $W_{prom}$ is a 31×31 matrix.

In the first embodiment, in the decision process of the decision means 33, it is decided whether or not the promoter exists in the test segment by deciding at which side of a predetermined threshold (for example, zero) exists only the feature decision elements of the first row (for example, the elements of the first row, in the case of a vector, the first element thereof) selected according to the positions in the matrix of the feature elements of the first column (for example, the elements of the first column) included in the predicted basis matrix $W_{prom}{}^{-1}$ among the elements constituting the separation data or the separation data matrix $Y_{test}$ obtained by the separation processing means (see step S17 of FIG. 32 and FIG. 38). However, in the second embodiment, as shown in FIG. 49, it is decided whether or not the promoter exists in the test segment by using the feature decision elements of a plurality of the rows selected according to the positions in the matrix of the feature elements of a plurality of the columns included in the predicted basis matrix $W_{prom}{}^{-1}$ among the elements constituting the $Y_{test}$ (see FIG. 44). In the first embodiment or the second embodiment, instead of the hard decision of deciding the existence of the promoter, the soft decision of deciding the degree of existence of the promoter may be performed.

More specifically, in the second embodiment, as shown in FIG. 49, the decision means extracts only the feature decision elements of a plurality of the rows among the elements constituting the $Y_{test}$ having 31 rows (in the case of a vector, 31 elements) to generate a $Y_{test}'$ having, for example, 23 rows (in the case of a vector, 23 elements). The decision means obtains a value indicating the similarity measure of the column vectors $Y_{test}'$ (k) (k=1, 2, 3, . . . . However, in the case of one test data, one column vector) to the column vectors $Y_{prom}'$ (j) (j=1 to 106) of the $Y_{prom}'$ (see FIG. 44) generated by extracting only the feature decision elements of the true data-corresponding portions of the $Y_{prom}$. Here, the value indicating the similarity measure may denote a value obtained by calculating inner products of an arbitrary one column vector $Y_{test}'$ (k) of the $Y_{prom}'$ to the column vectors $Y_{prom}'$ (j) (j=1 to 106) of the $Y_{prom}'$ (see FIG. 44) and by taking an average of the values of the Np (106) inner products. Alternatively, if the centroid vector from the column vectors $Y_{prom}'$ (j) (j=1 to 106) of the $Y_{prom}'$ (see FIG. 44) is obtained and stored in advance, the equivalent value can be obtained by calculating the value of the inner product of an arbitrary one of the column vectors $Y_{test}'$ (k) of the $Y_{test}'$ to the centroid vector. The value indicating the similarity measure is not limited to the average of the values of the inner products to the column vectors $Y_{prom}'$ (j) (j=1 to 106) of the $Y_{prom}'$ or the value of the inner product of the centroid vector from the column vectors $Y_{prom}'$ (j) (j=1 to 106) of the $Y_{prom}'$ but other values may be used. If a value indicating the similarity measure to the set of the column vectors $Y_{prom}'$ (j) (j=1 to 106) of the $Y_{prom}'$ is used, it is possible to avoid a biased decision of deciding whether to be close to a specific known promoter. By deciding at which side of a predetermined threshold (for example, zero) the value indicating the obtained similarity measure exists, it is possible to decide whether or not the promoter candidate segment which is in a pre-numerical conversion state of the test data $X_{test}(k)$ corresponding to the $Y_{test}(k)$ as a basis of the $Y_{test}'(k)$ used to calculate the value indicating the similarity measure is a promoter. As a result, it is possible to decide whether or not the promoter exists in the test segment. For example, if the value indicating the similarity measure is a plus, it may be decided that the promoter exists. If the value is a minus, it may be decided that the promoter does not exist. In the case of the soft decision, by deciding a degree of the obtained value indicating the similarity measure, a degree of the existence of the promoter in the test segment can be decided.

According to the second embodiment, the same effects of the first embodiment can be obtained. In addition, since the decision process is performed by using the feature decision elements of a plurality of the rows as well as the feature decision elements of one row, it is possible to improve the decision scheme. In addition, since the alignment process is performed by removing a portion of the sequences of the spacer 35 or a portion of the sequences of the spacer 10 instead of the insertion of gaps, it is possible to reduce the dimension of the matrixes such as a promoter-associated separation matrix $W_{prom}$, so that it is possible to reduce a calculation amount and to improve a processing speed.

<Experiment For Effects>

In order to examine the effects of the present invention, the following experiment is carried out. Methods and conditions of the experiment are based on those of the second embodiment.

Firstly, as described in the second embodiment, in the training step, the training is performed by using the 106 known *Escherichia coli* promoters disclosed in the aforementioned Non-Patent Document 1. FIG. 45 illustrates the values of the elements of the first column of the inverse matrix 31×31 $W_{prom}^{-1}$ of the 31×31 promoter-associated separation matrix $W_{prom}$ (see FIG. 44) obtained as a result of the training. FIG. 47 illustrates the values of the elements of the 27-th column thereof. The numerals of the horizontal axis correspond to row numbers. FIG. 46 illustrates the values of the elements of the first row of the 31×212 promoter-associated separation data matrix $Y_{prom}$ (see FIG. 44) obtained together with the $W_{prom}$ as a result of the training result. FIG. 48 illustrates the values of the elements of the 27-th row thereof. The numerals of the horizontal axis correspond to row numbers.

The first column of the $W_{prom}^{-1}$ of FIG. 45 and the first row of the $Y_{prom}$ of FIG. 46 are selected as the feature elements and the feature decision elements, respectively. On the other hand, the 27-column of the $W_{prom}^{-1}$ of FIG. 47 and the 27-th row of the $Y_{prom}$ of FIG. 48 are not selected as the feature elements and the feature decision elements. In this manner, a total of 23 columns (23 bases) among the 31 columns (31 bases) constituting the $W_{prom}^{-1}$ are selected as the feature elements. Accordingly, a total of 23 rows among the 31 rows of the $Y_{prom}$ are selected as the feature decision elements. Alternatively, as a more strict selection condition, less than 23 rows may be selected as the feature decision elements.

Next, in the test step, 126 known *Escherichia coli* promoters disclosed in Non-Patent Document 1 are used as test data. The 126 *Escherichia coli* promoters are different from the 106 known *Escherichia coli* promoters used in the training step. In the 126 promoters, according to Non-Patent Document 1, the gaps are already inserted into the 126 promoters. Therefore, the gaps are removed from the promoters, so that gap-less promoters having a reduced sequence length of 40 mer to 50 mer are obtained as test data (test segments).

In addition, 5000 random sequences having a sequence length of 65 mer are generated and prepared as the test data (test segments). The symbol frequencies of A and T are set to 0.3, and the symbol frequencies of G and C are set to 0.2. Therefore, a total of 5126 unaligned test data (test segments) are prepared. In this case, the sequence length of 65 mer in the random sequence is used in order to exclude the sequences which are close to the promoter by performing the aforementioned homology score calculation. Therefore, in a case where the homology score calculation is not performed, the sequence length may be designed to be the same sequence length of the test segment used in an actual test step where the decision is performed on the sequences which are not known to be the promoter. For example, 5000 random sequences having the sequence length 50 may be generated and prepared.

Subsequently, with respect to the 5126 test data, the −10 box-corresponding sequences and the −35 box-corresponding sequences are selected by using the $W_{-10}$ and the $W_{-35}$. After that, an alignment process according to the method shown in FIG. 42 is performed to equalize the sequence lengths to 31 mer. In this case, the transcription start site is set to the 7-th mer from the lower stream. With respect to one test data (a test segment), only one transcription start site is selected (namely, in the experiment for effects, the slide setting for the transcription start site shown in FIG. 36 are not performed). In addition, the correlation decision process of the −10 box-corresponding sequences and the −35 box-corresponding sequences to the transcription-start-site neighborhood sequence is not performed.

Next, the 5126 aligned promoter candidate segments are converted to numerals by using the promoter symbol-frequency table $T_{prom}$ to generate 5126 test data. After that, as shown in FIG. 49, a matrix calculation process for multiplying the promoter-associated separation matrix $W_{prom}$ with the test data matrix $X_{test}$ in which the 5126 test data are bound is performed to generate a 31×5126 promoter-associated separation data matrix $Y_{test}$.

The feature decision elements of a plurality of the rows (in this case, a total of 23 rows) decided in advance by generating graphs for the $W_{prom}^{-1}$ and the $Y_{prom}$ and analyzing the graphs in the training step are extracted from the promoter-associated separation data matrix $Y_{test}$ to generate a 23×5126 matrix $Y_{test}'$. Next, the values of inner products of an arbitrary one of column vectors $Y_{test}'(k)$ (k=1 to 5126) of the $Y_{test}'$ to the column vectors $Y_{prom}'(j)$ (j=1 to 106) of the $Y_{prom}'$ (see FIG. 44), and the average of the values of the Np (106) inner products is obtained. The calculation of the value indicating the similarity measure is performed on all the column vectors $Y_{test}'(k)$ (k=1 to 5126) of the 5126 columns constituting the $Y_{test}'$. Alternatively, if the centroid vector from the column vectors $Y_{prom}'(j)$ (j=1 to 106) of the $Y_{prom}'$ (see FIG. 44) is obtained in advance, the equivalent value can be obtained by calculating the value of the inner product of an arbitrary one of the column vectors $Y_{test}'(k)$ (k=1 to 5126) of the $Y_{test}'$ to the centroid vector.

Next, by setting a threshold to zero, plus or minus of the values indicating the similarity measure obtained for each of the column vectors $Y_{test}'(k)$ (k=1 to 5126) is decided (namely, the hard decision is performed). As a result, a high recognition rate of 95.04% is obtained. Accordingly, it can be understood that good effects can be obtained according to the present invention. In addition, if the slide setting process for the translation start site or the correlation-decision process is performed, the recognition rate over 95.04% can be obtained.

MODIFICATIONS

The present invention is not limited to the aforementioned embodiments, but modifications may be made within the scope where the object of the present invention can be achieved.

In the aforementioned embodiments, the transcription start site as the specific site is disposed at the lower stream of the −35 box and the −10 box that are the partial patterns. However, the positional relation between the specific site and each of the partial patterns is not limited thereto. In the present invention, the specific site may be disposed at the lower stream of all the partial patterns, at the upstream of the all the partial patterns, or between the partial patterns.

In the aforementioned embodiments, the correlation of the two boxes, that is, the −35 box and the −10 box to the transcription-start-site neighborhood sequence is decided. However, the correlation of the all the partial patterns to the specific-site neighborhood sequence needs to be decided, but the correlation of a portion of the partial patterns to the specific-site neighborhood sequence may be decided.

In the aforementioned embodiments, the correlation of each of the partial patterns to the specific-site neighborhood sequence is decided. However, when a recognition process for non-hierarchical feature patterns is performed, the correlation of the non-hierarchical feature patterns to the specific-site neighborhood sequence may be decided.

In the aforementioned embodiments, the correlation decision is performed by using the independent component analysis (ICA) or the principal component analysis (PCA). However, the present invention is not limited thereto. For example, the correlation decision may be performed by using the neural network method or the like. In the neural network method, for example, in the training step, when the known partial pattern and the known specific-site neighborhood sequence which are correlated to each other are input, a coefficient may be designated so that the value (for example, 1) indicating that there is a correlation is output. On the other hand, when the non-correlated sequences (random sequences or the like) are input, a coefficient may be designated so that the value (for example, 0) indicating that there is no correlation is output. Next, in the test step, when the partial pattern-corresponding sequences and the specific-site neighborhood sequence included in the feature pattern putative sequences are input, it may be decided whether the output is the value (for example, 1) indicating that there is a correlation or the value (for example, 0) indicating that there is no correlation.

In the aforementioned embodiments, by setting (assuming) the transcription start site, the −35 box-corresponding sequences and the −10 box-corresponding sequences are selected. After that, it is decided whether or not there is a correlation of the −35 box-corresponding sequences and the −10 box-corresponding sequences to the transcription-start-site neighborhood sequence. However, instead of such an one-time process, a multiple-times repeating process may be used. For example, by setting (assuming) the transcription start sites, the −35 box-corresponding sequences and the −10 box-corresponding sequences are selected. After that, the transcription start site where there is a high degree of correlation of the −35 box-corresponding sequences and the −10 box-corresponding sequences to the transcription-start-site neighborhood sequence is searched. The −35 box-corresponding sequences and the −10 box-corresponding sequences may be decided based on the transcription start site in the multiple-times repeating process.

In the aforementioned embodiments, as shown by the two-dotted dashed lines in FIG. 36, a plurality of the promoter candidate segments are decided from one test segment. However, when each of the promoter candidate segments is decided, calculation processes are performed again on a plurality (9) of the −10 box putative sequences or a plurality (7) of the −35 box putative sequence. In order to avoid redundant calculation, the once-calculated result may be suitably preserved to be used again. In addition, the calculation processes which can be summarized and executed at one time may be integrally performed. For example, a calculation process on the −10 box putative sequence (j=5) performed at the time of deciding the promoter candidate segment with respect to the transcription start site set at a position and a calculation process on the −10 box putative sequence (j=4) performed at the time of deciding the promoter candidate segment with respect to the transcription start site set at a position shifted by 1 mer at the upstream thereof may have an overlapped portion of the processes. Therefore, a portion of the result of the former calculation process (for example, overlapped data among the $Y_{-10can}$ (j) of FIG. 21 may be preserved to be used for the latter calculation process. In addition, the data of $Y_{-10can}$ Y (j) of FIG. 21 are not obtained from the partitioned nine-10 box putative sequences. The data of the $Y_{-10can}$ (j) corresponding to a plurality of the −10 box putative sequences are obtained and summarized at one time. Nine data are extracted from the summarized data (the nine data is extracted by shift one-by-one) to be used for a process of calculating a summation q(j) of the inner products.

In the aforementioned embodiments, the promoter recognition system 10 is a system for recognizing the promoter that is a hierarchical feature pattern and has a variation in whole length of the feature pattern. However, the feature pattern recognition system according to the present invention may be employed as a system for recognizing the promoter that is a non-hierarchical feature pattern and has a constant value as the whole length of the feature pattern. In a case where there is a variation in the length of the feature pattern (in a case where there are multiple types of lengths), the promoter recognition system according to the present invention may be employed as a system for recognizing a non-hierarchical feature pattern or a system for recognizing hierarchical feature pattern with the same process as that of the non-hierarchical case.

For example, in a case where there is a variation in the length of the feature pattern, when the process for recognizing the non-hierarchical feature pattern or the process for recognizing the hierarchical feature pattern with the same process as that of the non-hierarchical case is performed, an alignment process for equalizing the lengths of the putative sequences to a constant length by inserting the gaps may be performed by using "BLAST" that is a conventional standard tool for executing the conventional algorithm that is called "Clustral W". In this case, the putative sequences are selected among the to-be-decided sequence or one test segment extracted from a segment that is a portion of the sequence by shifting by one discrete symbol and changing the length at each position. The alignment process for equalizing the lengths of a plurality of the putative sequences by inserting the gaps is performed. The test data for each of the putative sequences of which lengths are equalized are generated. The separation process of the separation processing means and the decision process of the decision means are performed on a plurality of the test data obtained from one test segment. Next, a process for deciding one sequence which is recognized as the feature pattern from a plurality of the putative sequences decided from the one test segment (that is, a process for recognizing the most-probable putative sequence as the feature pattern) or a process for deciding no sequence (that is, a process for deciding that there is not feature pattern in the test segment) may be performed. For example, in case of a feature pattern of which sequence length varies in a range of 25 mer to 30 mer (preferably, including an assumptive lengths of newly-to-be-found feature patterns), the putative sequence s having a length of 25 mer to 30 mer are selected with respect to a reference position (the right end of the feature pattern) among test segment. Next, similarly, the putative sequences having a length of 25 mer to 30 mer are selected with respect to a position shifted by 1 mer at the upstream (the right end of the feature pattern). As a result, a plurality of the putative sequences can be decided among the one test segment.

INDUSTRIAL APPLICABILITY

A feature pattern recognition system, method, and program according to the present invention can be suitably used to recognize, for example, a promoter or an enhancer in a DNA sequence, a motif in an amino acid sequence, a pattern in a mixed sequence of the DNA sequence and the amino acid sequence, or the like.

DESCRIPTION OF THE REFERENCE NUMERALS

10: promoter recognition system as a feature pattern recognition system
31: test data generating means
31A: putative −35 box data generating means as partial pattern putative data generating means
31B: putative −10 box data generating means as partial pattern putative data generating means
31C: putative extracted data generating means for −35 boxes as partial pattern putative data-associated separation data generating means
31D: putative −10 box data-associated separation data generating means as partial pattern putative data-associated separation data generating means
31E: −35 box-corresponding sequences selection means as partial pattern-corresponding sequences selection means
31F: −10 box-corresponding sequences selection means as partial pattern-corresponding sequences selection means
31G: promoter candidate segment selection means as feature pattern putative sequence selection means
31H alignment processing means
31J: promoter candidate segment numerical conversion means as feature pattern putative sequence numerical conversion means
32: separation processing means
33: decision means
41: −35 box symbol-frequency table storage means as partial-pattern symbol-frequency table storage means
42: −35 box-associated separation matrix storage means as partial-pattern separation matrix storage means
43: −35 box-associated separation data matrix storage means as partial-pattern separation data matrix storage means
51: −10 box symbol-frequency table storage means as partial-pattern symbol-frequency table storage means
52: −10 box-associated separation matrix storage means as partial-pattern separation matrix storage means
53: −10 box-associated separation data matrix storage means as partial-pattern separation data matrix storage means
61: promoter symbol-frequency table storage means as whole-pattern symbol-frequency table storage means
62: promoter-associated separation matrix storage means as whole-pattern separation matrix storage means
70 correlation training result storage means
71 correlation-decision symbol-frequency table storage means
72 correlation-decision separation matrix storage means
A, T, G, C: discrete symbol
$T_{-35}$: −35 box symbol-frequency table as a partial-pattern symbol-frequency table
$T_{-10}$: −10 box symbol-frequency table as a partial-pattern symbol-frequency table
$T_{prom}$: promoter symbol-frequency table as a whole-pattern symbol-frequency table
$T_{BBS}$: correlation-decision symbol-frequency table
$W_{-35}$: −35 box-associated separation matrix as a partial-pattern separation matrix
$W_{-10}$: −10 box-associated separation matrix as a partial-pattern separation matrix
$W_{prom}$: promoter-associated separation matrix as a whole-pattern separation matrix
$W_{BBS}$ correlation-decision separation matrix
$X_{-35}$: −35 box-associated training data matrix as a partial-pattern training data matrix
$X_{-10}$: −10 box-associated training data matrix as a partial-pattern training data matrix
$X_{prom}$: promoter-associated training data matrix as a whole-pattern training data matrix)
$X_{BBS}$: correlation-decision training data matrix
$X_{BBS,test}$: correlation-decision data matrix
$X_{test}$: test data matrix
$Y_{-35}$: −35 box-associated separation data matrix as a partial-pattern separation data matrix
$Y_{-10}$: −10 box-associated separation data matrix as a partial-pattern separation data matrix
$Y_{-35can}$: putative −35 box data-associated separation data matrix as a partial pattern putative data-associated separation data matrix
$Y_{-10can}$: putative −10 box data-associated separation data matrix as a partial pattern putative data-associated separation data matrix
$Y_{prom}$: promoter-associated separation data matrix as a whole-pattern separation data matrix
$Y_{BBS,test}$: correlation-decision separation data matrix
$Z_{-35}$: putative −35 box data matrix as a partial pattern putative data matrix
$Z_{-10}$: putative −10 box data matrix as a partial pattern putative data matrix

The invention claimed is:

1. A method by computer of determining whether or not one of multiple known feature patterns that are similar to each other or a new feature pattern that is similar to the known feature pattern is included in a biological sequence represented by a finite number of discrete symbols, comprising the steps of:
providing a sample of a biological material;
analyzing the biological material to determine a biological sequence contained therein;
inputting the biological sequence into a computer;
assigning a discrete symbol for each component making up the biological sequence;
providing the multiple types of the known feature patterns;
providing multiple types of non-feature patterns that are different from the known feature patterns;
assigning a discrete symbol for each component making up the biological sequences of the multiple known feature patterns and multiple non-feature patterns;
generating a symbol frequency for each of the discrete symbols at each of the positions in the feature patterns using the multiple types of known feature patterns;
generating a symbol-frequency table by corresponding the symbol frequencies to the positions and types of the discrete symbols in the feature patterns;

converting to numerals the multiple types of known feature patterns and the multiple types of non-feature patterns that are different from the known feature patterns according to the positions and types of the discrete symbols by using the symbol-frequency table;

binding the numerals to generate a training data matrix and performing an independent component analysis or a principal component analysis by using the training data matrix to generate a separation matrix, as a matrix for performing inverse transformation of a basis matrix including feature elements representing the feature patterns;

generating test data by converting to numerals the biological sequence according to the positions and types of discrete symbols by using the symbol-frequency table;

obtaining separation data or a separation data matrix in which a plurality of the separation data are bound by performing a matrix calculation of multiplying the separation matrix with the test data or a test data matrix in which a plurality of the test data are bound; and deciding whether or not one of the multiple types of the known feature patterns or the new feature pattern similar to the known feature patterns is included in the biological sequence or deciding a degree of existence thereof by using values of feature decision elements assigned according to internal-matrix positions of the feature elements included in the basis matrix among elements constituting the separation data or the separation data matrix.

2. The feature pattern recognition method according to claim 1, wherein the feature patterns are hierarchical feature patterns that includes a plurality of partial patterns located at different regions therein, and region positions of the partial patterns in the feature patterns and a whole length of the feature patterns include multiple types of region positions and multiple types of lengths according to a difference of the types of the feature patterns;

a whole-pattern symbol-frequency table is generated by equalizing whole pattern lengths of the multiple types of the known feature patterns to a constant length by inserting gaps or removing discrete symbols of regions other than the partial patterns, obtaining the symbol frequency for each type of the discrete symbols including the gaps at each of the sequence positions in the feature patterns by using the multiple types of the known feature patterns of which whole pattern lengths are equalized, and corresponding the symbol frequencies to the sequence positions in the feature patterns and the types of the discrete symbols including the gaps, a whole-pattern separation matrix is obtained by performing the independent component analysis or the principal component analysis by using a whole-pattern training data matrix generated from the multiple types of the known feature patterns of which whole pattern lengths are equalized and the multiple types of non-feature patterns of which lengths are equalized to the lengths of the multiple types of the known feature patterns;

the feature pattern recognition method further comprising:

storing a partial-pattern symbol-frequency table obtained for each partial pattern in each region;

storing a partial-pattern separation matrix obtained for each partial pattern in each region; and storing elements of at least true data-corresponding portions of a partial-pattern separation data matrix that is obtained together with the partial-pattern separation matrix in a training step for each partial pattern in each region;

wherein a partial-pattern symbol-frequency table is generated by obtaining, for each partial pattern in each region included in the known feature patterns, the symbol frequencies for each of the types of the discrete symbols at each sequence position in the partial patterns by using the multiple types of the known partial patterns and corresponding the symbol frequencies to the sequence positions in the partial patterns and the types of the discrete symbols;

for each partial pattern in each region included in the known feature patterns, a partial-pattern separation matrix is generated as a matrix for performing inverse transformation of a partial-pattern basis matrix including feature elements representing the partial patterns generated by converting to numerals the multiple types of known partial patterns and multiple types of non-partial patterns that are different from the known partial patterns according to the sequence positions and the types of the discrete symbols by using the partial-pattern symbol-frequency table, binding the numerals to generate a partial-pattern training data matrix, and performing an independent component analysis or a principal component analysis by using the partial-pattern training data matrix;

elements of at least true data-corresponding portions of a partial-pattern separation data matrix are obtained as a result of multiplication of the partial-pattern separation matrix with the partial-pattern training data matrix when the partial-pattern separation matrix is obtained by performing the independent component analysis or the principal component analysis, and when the test data is generated, the feature pattern recognition method further comprises:

generating a plurality of partial pattern putative data by selecting, for each partial pattern in each region, a plurality of partial pattern putative sequences of which lengths are the same as that of the partial pattern and of which positions are shifted from each other among the to-be-decided sequence, the segment thereof, or the test segment extracted from the sequence or the segment, and converting to numerals a plurality of the partial pattern putative sequences according to the sequence positions and the types of the discrete symbols by using the partial-pattern symbol-frequency table;

generating a plurality of partial pattern putative data-associated separation data or a partial pattern putative data-associated separation data matrix in which a plurality of the partial pattern putative data-associated separation data are bound by performing a matrix calculation of multiplying the partial-pattern separation matrix with each of the partial pattern putative data generated or a partial pattern putative data matrix in which a plurality of the partial pattern putative data are bound;

obtaining partial pattern putative data-associated separation data that are closest to column vectors of true data-corresponding portions of the partial-pattern separation data matrix among a plurality of the partial pattern putative data-associated separation data generated and selecting the partial pattern putative sequences corresponding to the obtained partial pattern putative data-associated separation data as partial pattern-corresponding sequences included in feature pattern putative sequences that are candidates of the feature pattern;

selecting the feature pattern putative sequence based on the partial pattern-corresponding sequences of the regions selected;

performing an alignment process for equalizing lengths of the feature pattern putative sequences selected to a constant length by inserting gaps or removing the discrete symbols of regions other than the partial patterns while each of the partial pattern-corresponding sequences of each region selected is maintained to be in a one-body state; and generating the test data by converting to numerals the feature pattern putative sequences of which lengths are equalized according to the sequence positions and the types of the discrete symbols including the gaps by using the whole-pattern symbol-frequency table.

3. The feature pattern recognition method according to claim 2, wherein, when the multiple types of the non-feature patterns of which whole pattern lengths are equalized to constitute the whole-pattern training data matrix used to obtain the whole-pattern separation matrix are generated, the feature pattern recognition method further comprises:

generating a plurality of partial pattern putative data by selecting, for each partial pattern in each region, a plurality of partial pattern putative sequences of which lengths are the same as that of the partial pattern and of which positions are shifted from each other among non-feature patterns-generating sequences prepared to generate the non-feature patterns, and converting to numerals a plurality of the partial pattern putative sequences according to the sequence positions and the types of the discrete symbols by using the partial-pattern symbol-frequency table;

generating a plurality of partial pattern putative data-associated separation data or a partial pattern putative data-associated separation data matrix in which a plurality of the partial pattern putative data-associated separation data are bound by performing a matrix calculation of multiplying the partial-pattern separation matrix with each of the partial pattern putative data or a partial pattern putative data matrix in which a plurality of the partial pattern putative data are bound;

obtaining partial pattern putative data-associated separation data that are closest to column vectors of true data-corresponding portions of the partial-pattern separation data matrix among the generated plurality of the partial pattern putative data-associated separation data and selecting the partial pattern putative sequences corresponding to the obtained partial pattern putative data-associated separation data as partial pattern-corresponding sequences included in the non-feature patterns;

selecting the non-feature patterns based on the selected partial pattern-corresponding sequences of the regions; and performing an alignment process for equalizing lengths of the selected non-feature patterns to a constant length by inserting gaps or removing the discrete symbols of regions other than the partial patterns while each of the partial pattern-corresponding sequences of each region is maintained to be in a one-body state.

4. The feature pattern recognition method according to claim 3, wherein, when the multiple types of the non-feature patterns are generated, the feature pattern recognition method comprises obtaining the partial pattern putative data-associated separation data in which a similarity measure of the partial pattern putative data-associated separation data to a set of the column vectors of true data-corresponding portions of the partial-pattern separation data matrix is maximized, when obtaining the partial pattern putative data-associated separation data that are closest to column vectors of true data-corresponding portions of the partial-pattern separation data matrix among a plurality of the partial pattern putative data-associated separation data.

5. The feature pattern recognition method according to claim 4, wherein the similarity measure consists of a summation of inner products of the partial pattern putative data-associated separation data to the column vectors of the true data corresponding portions of the partial-pattern separation data matrix.

6. The feature pattern recognition method according to claim 2, wherein the partial pattern putative data-associated separation data is obtained in which a similarity measure of the partial pattern putative data-associated separation data to a set of the column vectors of true data-corresponding portions of the partial-pattern separation data matrix is maximized, when obtaining the partial pattern putative data-associated separation data that are closest to column vectors of true data-corresponding portions of the partial-pattern separation data matrix among a plurality of the partial pattern putative data-associated separation data generated.

7. The feature pattern recognition method according to claim 6, wherein the similarity measure consists of a summation of inner products of the partial pattern putative data-associated separation data to the column vectors of the true data-corresponding portions of the partial-pattern separation data matrix.

8. The feature pattern recognition method according to claim 1, comprising deciding at which side of a predetermined threshold exist values of the feature decision element of the separation data or the separation data matrix or deciding magnitudes of the values thereof, thereby deciding whether or not one of the multiple types of the known feature patterns or the new feature pattern similar to the known feature patterns is included in the biological sequence or deciding a degree of existence thereof.

9. The feature pattern recognition method according to claim 1, wherein multiple columns of the feature elements appear in the basis matrix;

multiple rows of elements constituting the separation data or the separation data matrix are used as the feature decision elements; and it is decided whether or not one of the multiple types of the known feature patterns or the new feature pattern similar to the known feature patterns is included in the biological sequence or decided a degree of existence thereof by using values of the feature decision elements of the multiple rows of the separation data or the separation data matrix.

10. The feature pattern recognition method according to claim 9, wherein a value is calculated indicating a similarity measure of a column vector constructed with the values of the feature decision elements of the multiple rows of the separation data or the separation data matrix to column vectors constructed with values of feature decision elements of true data-corresponding portions of a separation data matrix that is obtained together with the separation matrix in the training step and decides at which side of a predetermined threshold exists the calculated value indicating the similarity measure or decides a magnitude of the value thereof, thereby deciding whether or not one of the multiple types of the known feature patterns or the new feature pattern similar to the known feature patterns is included in the biological sequence or deciding a degree of existence thereof.

11. The feature pattern recognition method according to claim 10, wherein;
   as the value indicating the similarity measure, a value is calculated indicating a similarity measure of a column vector constructed with the values of the feature decision elements of the multiple rows of the separation data or the separation data matrix to a set of column vectors constructed with values of feature decision elements of true data-corresponding portions of a separation data matrix that is obtained together with the separation matrix in the training step.

12. The feature pattern recognition method according to claim 11, wherein, as the value indicating the similarity measure, a value is calculated of an inner product of a column vector constructed with the values of the feature decision elements of the multiple rows of the separation data or the separation data matrix to a centroid vector from the column vectors constructed with the values of feature decision elements of true data-corresponding portions of a separation data matrix that is obtained together with the separation matrix in the training step or an equivalent value thereof.

13. The feature pattern recognition method according to claim 2,
   wherein a plurality of test data is generated for an arbitrary one test segment by selecting the feature pattern putative sequences while shifting by one discrete symbol among the biological sequence, an alignment process performed for equalizing lengths of the selected feature pattern putative sequences to a constant length by inserting gaps or removing discrete symbols of regions other than the partial patterns, and the feature pattern putative sequences converted to numerals of which lengths are equalized according to the sequence positions and the types of the discrete symbols including the gaps by using the whole-pattern symbol-frequency table,
   obtaining, for each test segment, a plurality of separation data or a separation data matrix in which a plurality of the separation data are bound by performing a matrix calculation of multiplying the whole-pattern separation matrix with a plurality of the test data or a test data matrix in which a plurality of the test data are bound, and
   deciding at which side of a predetermined threshold exists a value of each of the feature decision elements assigned according to internal-matrix positions of the feature elements included in the basis matrix among elements constituting a plurality of the separation data or the separation data matrix for the arbitrary one test segment, obtaining a value of the feature decision element of which absolute value of a difference from the threshold is largest or of which degree of feature pattern closeness is highest among the values of feature decision elements which are decided to represent the feature pattern or a degree of the feature pattern closeness, and recognizing that the feature pattern putative sequence corresponding to the test data assigned with the obtained value of the feature decision element is one of multiple types of the known feature patterns or a new feature pattern that similar to the known feature patterns.

14. The feature pattern recognition method according to claim 2, comprising
   generating a plurality of test data for arbitrary one test segment by selecting the feature pattern putative sequences while shifting by one discrete symbol among the to-be-decided sequence, the segment thereof, or the test segment extracted from the sequence or the segment, performing an alignment process for equalizing lengths of the selected feature pattern putative sequences to a constant length by inserting gaps or removing discrete symbols of regions other than the partial patterns, and converting to numerals the feature pattern putative sequences of which lengths are equalized according to the sequence positions and the types of the discrete symbols including the gaps by using the whole-pattern symbol-frequency table,
   obtaining, for each test segment, a plurality of separation data or a separation data matrix in which a plurality of the separation data are bound by performing a matrix calculation of multiplying the whole-pattern separation matrix with a plurality of the test data or a test data matrix in which a plurality of the test data are bound, and
   calculating a value indicating a similarity measure of each column vectors constructed with the values of the feature decision elements of multiple rows assigned according to internal-matrix positions of the feature elements of multiple columns included in the basis matrix among elements constituting a plurality of the separation data or the separation data matrix for the arbitrary one test segment to column vectors constructed with values of feature decision elements of true data-corresponding portions of a separation data matrix that is obtained together with the whole-pattern separation matrix in the training step, deciding at which side of a predetermined threshold exists a value indicating the similarity measure or deciding a magnitude of the value thereof, obtaining a value indicating the similarity measure of which absolute value of a difference from the threshold is largest or of which degree of feature pattern closeness is highest among the values of the similarity measure which are decided to represent the feature pattern or a degree of the feature pattern closeness, and recognizing that the feature pattern putative sequence corresponding to the test data assigned with the obtained value indicating the similarity measure is one of multiple types of the known feature patterns or a new feature pattern that is similar to the known feature patterns.

15. The feature pattern recognition method according to claim 2, further comprising,
   when the partial patterns of each region included in the hierarchical feature patterns have a correlation with specific-site neighborhood sequences including a specific site of the sequence,
   storing information including a correlation training result obtained by training in advance as information used to decide the correlation of the partial pattern of each region with the specific-site neighborhood sequences,
   wherein a plurality of the partial pattern putative sequences is selected for each of the partial patterns of each region based on a relative positional relation to the specific site or a relative positional relation to partial pattern putative sequences of other regions defined according to the relative positional relation to the specific site, and
   wherein an existence of correlation or a degree of the correlation is decided between selected partial pattern-corresponding sequences of each region and the specific-site neighborhood sequences by using the information including a stored correlation training result and, if there is no correlation or if the degree of the correlation is low, does not perform a decision process for the feature pattern putative sequence based on the partial pattern-corresponding sequences of each region and the specific site in the specific-site neighborhood sequences.

16. The feature pattern recognition method according to claim 15, further comprising storing a correlation-decision symbol-frequency table generated by binding the known partial patterns of at least one region among a plurality of regions included in the known feature patterns with known specific-site neighborhood sequences to generate multiple types of correlation-binding sequences, obtaining a symbol frequency for each type of the discrete symbols at each sequence position in the correlation-binding sequences by using multiple types of correlation-binding sequences, and corresponding the symbol frequencies to the sequence positions and the types of the discrete symbols in the correlation-binding sequences; and storing a correlation-decision separation matrix, as a matrix for performing inverse transformation of a correlation-decision basis matrix including feature elements representing correlation-binding sequences, generated by converting to numerals correlation-binding sequences generated by binding the known partial patterns of at least one region among a plurality of the regions with the known specific-site neighborhood sequences and non-correlation-binding sequences generated by binding the known partial patterns of at least one region among a plurality of the regions with non-specific-site neighborhood sequences different from the known specific-site neighborhood sequences according to the sequence positions and the types of the discrete symbols by using the correlation-decision symbol-frequency table, binding the numerals to generate a correlation-decision training data matrix, and performing an independent component analysis or a principal component analysis by using the correlation-decision training data matrix; and when deciding the existence of a correlation or a degree of the correlation between the partial pattern-corresponding sequences of each region and the specific-site neighborhood sequences, generating correlation-decision sequences by binding the partial pattern-corresponding sequences of at least one region among a plurality of the regions with the specific-site neighborhood sequences, converting to numerals the correlation-decision sequences according to the sequence positions and the types of the discrete symbols by using the correlation-decision symbol-frequency table to generate correlation-decision data, performing a correlation-decision separation process for obtaining correlation-decision separation data or a correlation-decision separation data matrix in which a plurality of the correlation-decision separation data are bound by performing a matrix calculation of multiplying the correlation-decision separation matrix with the correlation-decision data or a correlation-decision data matrix in which a plurality of the correlation-decision data are bound, and deciding the existence of the correlation or a degree of the correlation by using a value of the correlation-decision element assigned according to internal-matrix positions of the feature elements included in the correlation-decision basis matrix among the correlation-decision separation data obtained in the correlation-decision separation process or the elements constituting the correlation-decision separation data matrix.

17. The feature pattern recognition method according to claim 16, further comprises deciding the existence of correlation or a degree of the correlation by deciding at which side of a predetermined correlation-decision threshold exists a value of the correlation-decision element.

18. The feature pattern recognition method according to claim 1, wherein the biological sequence is a DNA sequence, the discrete symbols are A, T, G, and C representing nucleotides constituting the DNA sequence or substitute symbols thereof, and the feature pattern is a promoter in the DNA sequence.

19. The feature pattern recognition method according to claim 2, wherein the biological sequence is a DNA sequence, the discrete symbols are A, T, G, and C representing nucleotides constituting the DNA sequence or substitute symbols thereof, the feature pattern is a promoter in the DNA sequence, and the partial patterns are a −35 box and a −10 box included in the promoter.

20. The feature pattern recognition method according to claim 15, wherein the biological sequence is a DNA sequence, the discrete symbols are A, T, G, and C representing nucleotides constituting the DNA sequence or substitute symbols thereof, the feature pattern is a promoter in the DNA sequence, the partial patterns are a −35 box and a −10 box included in the promoter, the specific site is a transcription start site of the DNA sequence, and the specific-site neighborhood sequences is a transcription-start-site neighborhood sequence.

21. The feature pattern recognition method according to claim 1, wherein the biological sequence is an amino acid sequence constituting a protein, the discrete symbols are symbols representing the amino acids constituting the amino acid sequence, and the feature pattern is a motif of the amino acid sequence.

22. The feature pattern recognition method according to claim 1,
wherein the lengths of the feature pattern include multiple types of lengths according to differences of the types of the feature patterns, and further comprises the steps of:
storing a symbol-frequency table generated by equalizing the lengths of the multiple types of the known feature patterns to a constant length by inserting gaps, by obtaining the symbol frequency for each type of the discrete symbols including the gaps at each of the sequence positions in the feature patterns by using the multiple types of the known feature patterns of which lengths are equalized, and corresponding the symbol frequencies to the sequence positions in the feature patterns and the types of the discrete symbols including the gaps,
storing a separation matrix obtained by performing the independent component analysis or the principal component analysis by using a training data matrix generated from the multiple types of the known feature patterns of which lengths are equalized and the multiple types of non-feature patterns of which lengths are equalized to the lengths of the multiple types of the known feature patterns, and
generating the test data by selecting putative sequences that become candidates of the feature patterns among the biological sequence, performing an alignment process for equalizing lengths of the selected putative sequences to a constant length by inserting gaps, and converting to numerals the putative sequences of which lengths are equalized according to the sequence positions and the types of the discrete symbols including the gaps by using the symbol-frequency table.

23. The feature pattern recognition method according to claim 22, further comprising the steps of:
generating a plurality of test data for an arbitrary one test segment by selecting the putative sequences while shifting by one discrete symbol and changing a length at each position among the biological sequence, performing an alignment process for equalizing lengths of a plurality of the selected putative sequences to a constant length by inserting gaps, and converting to numerals the putative sequences of which lengths are equalized according to the sequence positions and the types of the discrete symbols including the gaps by using the symbol-frequency table, obtaining, for each test segment, a plurality of separation data or a separation data matrix in which a plurality of the separation data are bound by performing a matrix calculation of multiplying the separation matrix with a plurality of the test data, and deciding at which side of a predetermined threshold exists a value of each of the feature decision elements assigned according to internal-matrix positions of the feature elements included in the basis matrix among elements constituting a plurality of the separation data or the separation data matrix for the arbitrary one test segment, obtaining a value of the feature decision element of which an absolute value of a difference from the threshold is largest or of which a degree of feature pattern closeness is highest among the values of feature decision elements which are decided to represent the feature pattern or a degree of the feature pattern closeness, and recognizing that the feature pattern putative sequence corresponding to the test data assigned with the obtained value of the feature decision element is one of multiple types of the known feature patterns or a new feature pattern that is similar to the known feature patterns.

24. The feature pattern recognition method according to claim 22, comprising generating a plurality of test data for an arbitrary one test segment by selecting the putative sequences while shifting by one discrete symbol and changing a length at each position among the biological sequence, performing an alignment process for equalizing lengths of a plurality of the selected putative sequences to a constant length by inserting gaps, and converting to numerals the putative sequences of which lengths are equalized according to the sequence positions and the types of the discrete symbols including the gaps by using the symbol-frequency table, obtaining, for each test segment, a plurality of separation data or a separation data matrix in which a plurality of the separation data are bound by performing a matrix calculation of multiplying the separation matrix with a plurality of the test data or a test data matrix in which a plurality of the test data are bound, and calculating a value indicating a similarity measure of each of column vectors constructed with the values of the feature decision elements of multiple rows assigned according to internal-matrix positions of the feature elements of multiple columns included in the basis matrix among elements constituting a plurality of the separation data or the separation data matrix for the arbitrary one test segment to column vectors constructed with values of feature decision elements of true data-corresponding portions of a separation data matrix that is obtained together with the separation matrix in the training step, deciding at which side of a predetermined threshold exists a value indicating the similarity measure or decides a magnitude of the value thereof, obtaining a value indicating the similarity measure of which absolute value of a difference from the threshold is largest or of which degree of feature pattern closeness is highest among the values of the similarity measure which are decided to represent the feature pattern or a degree of the feature pattern closeness, and recognizing that the feature pattern putative sequence corresponding to the test data assigned with the obtained value indicating the similarity measure is one of multiple types of the known feature patterns or a new feature pattern that similar to the known feature patterns.

* * * * *